US007988971B2

(12) United States Patent
Dimitrov et al.

(10) Patent No.: US 7,988,971 B2
(45) Date of Patent: Aug. 2, 2011

(54) HUMAN MONOCLONAL ANTIBODIES AGAINST HENDRA AND NIPAH VIRUSES

(75) Inventors: Dimiter S. Dimitrov, Rockville, MD (US); Zhu Zhongyu, Frederick, MD (US); Christopher C. Broder, Silver Spring, MD (US)

(73) Assignees: The United States of America as represented by the Department of Health and Human Services, Washington, DC (US); Henry M. Jackson Foundation for the Advancement of Military Medicine, Inc., Rockville, MD (US)

( * ) Notice: Subject to any disclaimer, the term of this patent is extended or adjusted under 35 U.S.C. 154(b) by 478 days.

(21) Appl. No.: 11/886,307

(22) PCT Filed: Nov. 4, 2005

(86) PCT No.: PCT/US2005/040050

§ 371 (c)(1), (2), (4) Date: Jan. 16, 2009

(87) PCT Pub. No.: WO2006/137931

PCT Pub. Date: Dec. 28, 2006

(65) Prior Publication Data

US 2009/0214428 A1 Aug. 27, 2009

Related U.S. Application Data

(60) Provisional application No. 60/661,766, filed on Mar. 14, 2005, provisional application No. 60/678,547, filed on May 5, 2005, provisional application No. 60/718,902, filed on Sep. 20, 2005.

(51) Int. Cl.

| | |
|---|---|
| ***A61K 39/42*** | (2006.01) |
| ***A61K 39/395*** | (2006.01) |
| ***A61K 39/12*** | (2006.01) |
| ***A61K 39/155*** | (2006.01) |
| ***C07K 16/00*** | (2006.01) |
| *A61K 39/275* | (2006.01) |

(52) U.S. Cl. ............... 424/147.1; 424/130.1; 424/141.1; 424/159.1; 424/204.1; 424/211.1; 530/387.1; 530/388.1; 530/388.2; 530/388.3

(58) Field of Classification Search ........................ None
See application file for complete search history.

(56) References Cited

FOREIGN PATENT DOCUMENTS

| | | | |
|---|---|---|---|
| WO | WO94/09136 | * | 4/1994 |
| WO | WO 03/057824 | | 7/2003 |
| WO | WO 2005/028673 | | 3/2005 |

OTHER PUBLICATIONS

Vajdos et al., Comprehensive Functional Maps of the Antigen binding Site of an Anti-ErbB2 Antibody Obtained with Shotgun Scanning Mutagenesis, 2002, Journal of Molecular Biology, vol. 320, pp. 415-428.*
Zhu et al., Exceptionally Potent Cross-Reactive Neutralization of Nipah and Hendra Viruses by a Human Monoclonal Antibody, 2008, Journal of Infectious Diseases, vol. 197, pp. 846-853.*
Bonaparte et al. (2005), Ephrin-B2 Ligand is a Functional Receptor for Hendra virus and Nipah Virus. PNAS 102:10652-10657.
Bossart et al. (2002). Membrane Fusion Tropism and Heterotypic Functional Activities of the Nipah Virus and Hendra Virus Envelope Glycoproteins. J. Virol. 6:11186-11198.
Bossart et al. (2001). Functional Expression and Membrane Fusion Tropism of the Envelope Glycoproteins of Hendra Virus. Virology 290: 121-135.
Bossart et al. (2003). Nipah and Hendra Virus Fusion, Entry and its Inhibition. J. Clin. Virol. 28(S1)S40:L2-L3.
Butler, D. (2004). Fatal Fruit Bat Virus Sparks Epidemic in Southern Asia. Nature 429:7.
Chew et al. (2000). Risk Factors for Nipah Virus Infection Among Abattoir Workers in Singapore. J. Infect. Dis. 181:1760-1763.
Chua et al. (2000). High Mortality in Nipah Encephalitis Is Associated with Presence of Virus in Cerebrospinal Fluid. Ann. Neurol. 48:802-805.
Crameri et al. (2002). A Rapid Immune Plaque Assay for the Detection of Hendra and Nipah Viruses and Anti-Virus Antibodies. J. Virol. Methods 99:41-51.
Dimitrov, D. (2004). Virus Entry: Molecular Mechanism and Biomedical Applications. Nature Reviews Microbiology 2: 109-122.
Eaton, B. T. (2001). Introduction to Current Focus on Hendra and Nipah Viruses. Microbes Infect. 3:277-278.
Enserink, M. (2004). Nipah Virus (or a Cousin) Strikes Again. Science 303:1121.
Field et al. (2001). The Natural History of Hendra and Nipah Viruses. Microbes Infect. 3:307-314.
Goh et al. (2000). Clinical Features of Nipah Virus Encephalitis Among Pig Farmers in Malaysia. N. Engl. J. Med. 342:1229-1235.
Guillaume et al. (2004). Nipah virus: Vaccination and passive protection studies in a hamster model. J. Virol. 78: 834-840.
Harcourt et al. (2000). Molecular Characterization of Nipah Virus, a Newly Emergent Paramyxovirus. Virology 271: 334-349.
Hooper et al. (2001). Comparative Pathology of the Disease Caused by Hendra and Nipah Viruses. Microbes Infect. 3:315-322.
Hsu et al. (2004). Nipah Virus Encephalitis Reemergence, Bangladesh. Emerg. Infect. Dis. 10:2082-2087.
Lamb et al. (2001). Paramyxoviridae: The Viruses and their Replication, in *Fields Virology*, eds. Knippe, D. M. & Howley, P. M., Lippincott Williams & Wilkins, Philadelphia, pp. 1305-1340.

(Continued)

*Primary Examiner* — Zachariah Lucas
*Assistant Examiner* — Benjamin P Blumel
(74) *Attorney, Agent, or Firm* — Morgan, Lewis & Bockius LLP

(57) ABSTRACT

The present invention relates to monoclonal antibodies that bind or neutralize Hendra or Nipah virus. The invention provides such antibodies, fragments of such antibodies retaining Hendra or Nipah virus-binding ability, fully human antibodies retaining Hendra or Nipah virus-binding ability, and pharmaceutical compositions including such antibodies. The invention further provides for isolated nucleic acids encoding the antibodies of the invention and host cells transformed therewith. Additionally, the invention provides for prophylactic, therapeutic, and diagnostic methods employing the antibodies and nucleic acids of the invention.

16 Claims, 16 Drawing Sheets

OTHER PUBLICATIONS

Lee et al. (1999). The Neurological Manifestations of Nipah Virus Encephalitis, a Novel Paramyxovirus. Ann. Neurol. 46:428-432.
Lim et al. (2000). Nipah Viral Encephalitis or Japanese Encephalitis? MR Findings in New Zoonotic Disease. Am. J. Neuroradiol. 21:455-461.
Mourland et al. (2002). Novel Broadly Cross-reactive HIV-1 Neutralizing Human Monoclonal Fab Selected for Binding to gp120-CD4-CCR-5 Complexes. Proc. Natl. Acad. Sci. USA 99: 6913-6918.
Murray et al. (1995). A Morbillivirus That Caused Fatal Disease in Horses and Humans. Science 268: 94-97.
Tamin et al. (2002). Functional Properties of the Fusion and Attachment Glycoproteins of Nipah Virus. Virology 296: 190-200.
Unknown Author (2004). Nipah Encephalitis Outbreak Over Wide Area of Western Bangladesh, 2004. Health and Science Bulletin (ICDDR,B) 2:5-9.
Unknown Author (2004). Nipah Virus Outbreak(s) in Bangladesh, Jan.-Apr. 2004. Wkly Epidimal Rece. 79: 168-171.
Ward, J. W. ed. (1999). Update: Outbreak of Nipah Virus—Malaysia and Singapore, 1999. Morb. Morta.I Wkly. Rep. 48:335-337.
Yu et al. (1998). The Attachment Protein of Hendra Virus Has High Structural Similarity but Limited Primary Sequence Homology Compared with Viruses in the Genus Paramyxovirus. Virology 251:227-233.
Zhang et al. (2004). Improved Breadth and Potency of HIV-1-Neutralizing Human Single-Chain Antibody by Random Mutagenesis and Sequential Antigen Panning. J. Mol. Biol. 335: 209-219.

* cited by examiner

For all the VH and VL sequences, the CDR1-3s were underlined and the FR1-4s were the fragments divided by the three CDRs. The following example can be applied to all the sequences.

Example:

FR1 FR2 FR3 FR4
xxxxxxxxxxxxxxxxxxxxxxxxxxxxxxxxxxxxxxxxxxxxxxxxxxxxxxxxxxxxxxxxxxxxxxxxxxxxxxxxxxxxxxxxxxxx
CDR1 CDR2 CDR3 m101-m107 Sequences:

m101 VH3 (SEQ ID NO: 1)
QVQLVQSGAEVKKPGASVKVSCKASGGTFSSYAISWVRQAPGQ
GLEWMGGIIPIFGTANYAQKFQGRVTITADESTSTAYME
LSSLRSGDTAVYYCARDPGGYSYGPYYYYYGMDVWGQ
GTTVTVSS m101 Vk1 (SEQ ID NO: 9)
DIQMTQSPSSVSASVGDRVTITCRASQGIGPWLAWYQQKPGKAP
KFLIYRASTLQSGVPSRFSGSGSGTDFTLTISSLQPEDFAT
YYCQQAHSFPFTFGPGTKVDIKRTVA m102 VH1 (SEQ ID NO: 17)
EVQLVQSGAEVKKPGSSVKVSCKSSGGTFSNYAINW
VRQAPGQGLEWMGGIIPILGIANYAQKFQGR
VTITTDESTSTAYMELSSLRSEDTAVYYCARG
WGREQLAPHPSQYYYYYYGMDVWGQGTTVT
VSS m102 Vk3 (SEQ ID NO: 25)
EIVLTQSPGTLSLSPGERATLSCRASQSITNGRLAWY
QQKPGQAPRLLIYGVSSRASGIPERFSGSGSGT
DFTLTISRLEPEDFAVYYCQQYGSSVLFGPGT
KVDIKRTVA m103 VH3 (SEQ ID NO: 33)
EVQLVESGGGLIQPGGSLRLSCAASGFTVSSNYMSW
VRQAPGKGLEWVSVIYSGGSTYYADSVKGRF
TISRDNSKNTLYLQMNSLRAEDTAVYYCARD
SRYHDAFDIWGQGTMVTVSS

Fig. 8 m103 Vk2 (SEQ ID NO: 41)
D V V M T Q S P L S L P V T P G E P A S I S C R S S Q S L L H S N G Y N Y
L D W Y L Q K P G Q S P Q L L I Y L G S N R A S G V P D R F S G
S G S G T D F T L K I S R V E A E D V G V Y Y C M Q A L Q T L
Y T F G Q G T K L E I K R T V A m104 VH1 (SEQ ID NO: 49)
Q V Q L Q Q S G A E V K K P G S S V K V S C K A S G G T F S S Y A I S W
V R Q A P G Q G L E W M G G I I P I F G T A N Y A Q K F Q G R
V T I T A D E S T S T A Y M E L S S L R S E D T A V Y Y C A R E
S S W L D A F D I W G Q G T M V T V S S m104 Vk2 (SEQ ID NO: 57)
D V V M T Q S P L S L S V T A G E P A S I S C R S S Q S L L H S N G H I Y
L D W Y L Q K P G Q S P Q L L I Y M A S N R A S G V P D R F S
G S G S G T D F T L R I N R V E T E D V G I Y Y C M Q S L H T T
R T F G Q G T K V E I K R T V A m105 VH3 (SEQ ID NO: 65)
Q V Q L V Q S G G G V V Q P G R S L R L S C A A S G F T F S S Y A M H
W V R Q A P G K G L E W V A V I S Y D G S N K Y Y A D S V K
G R F T I S R D N S K N T L Y L Q M N S L R A E D T A V Y Y C
A R V G G I T G T A D A F D I W G Q G T M V T V S S m105 Vk1 (SEQ ID NO: 73)
D V V M T Q S P L S L P V T L G Q P A S I S C R S S Q S L V Y S D G N T
Y L N W F Q Q R P G Q S P R R L I Y K V S N R D S G V P D R F S
G S G S G T D F T L K I S R V E A E D V G V Y Y C M Q G T H W
P F T F G P G T K V D I K R T V A m106 VH1 (SEQ ID NO: 81)
Q V Q L Q Q S G A E V K K P G S S V K V S C K A S G G T F S S Y A I S W
V R Q A P G Q G L E W M G G I I P I F G T A N Y A Q K F Q G R
V T I T A D K S T S T A Y M E L S S L R S E D T A V Y Y C A R D
Q L A G Y Y Y D S S G Y H Y Y Y Y G M D V W G Q G T T V T V
S S m106 Vk1 (SEQ ID NO: 89)
D I Q M T Q S P S S L S A S V G D R V T I T C R A S Q S I S S Y L N W Y Q
Q K P G K A P K L L I Y A A S S L Q S G V P S R F S G S G S G T
D F T L T I S S L Q P E D F A T Y Y C Q Q S Y S T P I T F G Q G T
R L E I K R T V A

Fig. 8 (continued[5])

m107VH1 (SEQ ID NO: 97)
E V Q L V Q S G A E V K K P G A S V K V S C K A S G Y T F T G Y Y M H
W V R Q A P G Q G L E W M G I I N P S G G S T S Y A Q K F Q G
R V T M T R D T S T S T V Y M E L S S L R S E D T A V Y Y C A R
D H V H G P D A F D I W G Q G T M V T V S S m107 VL1 (SEQ ID NO: 105)
S Y E L T Q P P S A S G T P G Q R V T I S C S G S S S N I G S N T V N W Y
Q Q L P G T A P K L L I Y R N N Q R P S G V P D R F S G S K S G
T S A S L A I S G L Q S E D E A D Y Y C A A W D D S L H V V F
G G G T K L T V L G Q P K A m108-117 mabs VH +VL protein sequences:

M108
VH (SEQ ID NO: 113)
E V Q L V E S G G G L V K P G G S L R L S C A A S G F T F S D
Y Y M S W I R Q A P G K G L E W V S Y I S S S G S T I Y Y A D S
V K G R F T I S R D N A K N S L Y L Q M N S L R A E D T A V Y
Y C A R V G G A F D I W G Q G T M V T V S S

VL (SEQ ID NO: 121)
N F M L T Q P H S V S G S P G K T V T I S C T R S S G S I A S N Y V Q W Y R Q S
P G S A P T T V I Y E G Y Q R P S G V P D R F S G S I D S S S N S A S L T I S G L
E T E D E A D Y Y C Q S Y D A T N H Q V V F G G G T K L T V L

M109
VH (SEQ ID NO: 129)
Q M Q L Q Q W G A G L L K P S E T L S L T C A V Y G G S F S G
Y Y W S W I R Q P P G K G L E W I G E I N H S G S T N Y N P S
L K S R V T I S V D T S K N Q F S L K L S S V T A A D T A V Y Y
C A R G W F R D W Y F D L W G R G T L V T V S S

VL (SEQ ID NO: 137)
D I Q M T Q S P S S L S A S V G D R V T I T C R A S Q D I R N D L G W Y Q Q R P G
K A P K L L I Y A A S S L Q S G V P S R F S G S G S G T D F T L T I S S L Q P E D
S A T Y F C L Q D Y Q Y P W T F G Q G T K V E I K R

Fig. 8 (continued²)

M110

VH (SEQ ID NO: 145)

E V Q L V Q S G G G L V Q P G R S L R L S C A A S G F T F D D
Y A M H W V R Q A P G K G L E W V S A I S G S G G S T Y Y A
D S V K G R F T I S R D N S K N T L Y L Q M N S L R A E D T A
V Y Y C A S E G L P E T D D A F D I W G Q G T M V T V S S

VL (SEQ ID NO: 153)

D V V M T Q S P L S L P V T P G E P A S I S C R S S Q S L L Y S D G Y N Y L D W
Y L Q K P G Q S P Q L L I Y L G S R R A S G V P D R F S G S G S G T D F T L K I
N T V E A E D V G V Y Y C M Q G V E I P F T F G P G T K V E I K R

M111

VH (SEQ ID NO: 161)

Q V Q L V Q S G A E V K K P G A T V K I S C K V S G Y T F T D
Y Y M H W V Q Q A P G K G L E W M G L V D P E D G E T I Y A
E K F Q G R V T I T A D T S T D T A Y M E L S S L R S E D T A V
Y Y C A T E G A D Y W G Q G T L V T V S S

VL (SEQ ID NO: 169)

D V V M T Q S P L S L P V A L G Q P A S I S C R S S Q S L V H S D G N T Y L N
W F Q Q R P G Q S P R R L L Y K V S N R E S G V P D R F S G S G S G S D F T L K
I S R V E A E D V G I Y Y C M Q G T H W P P I T F G Q G T R L E I K R

M112

VH (SEQ ID NO: 177)

Q V Q L V Q S G A E V K K P G A T V K I S C K V S G Y T F T D
Y Y M H W V Q Q A P G K G L E W M G L V D P E D G E T I Y A
Q K F Q G R V T I T A D T S T N T A Y M E L S S L R S E D T A V
Y Y C A T D G A D Y W D Q G T L G T V S T

VL (SEQ ID NO: 185)

Q S V L T Q P P S V S G A P G Q T V T I S C T G S S S N I G G D S D V H W Y Q Q
L P G S A P K L L I Y G N R N R P S G V P D R F S G S R S G T S A S L A V I G V
Q A D D E A D Y Y C Q C Y D S S L N G Y V F G P G T K V I V L

M113

VH (SEQ ID NO: 193)

VL (SEQ ID NO: 201)
DIQMTQSPSSLSASVGDRVTITCRASQDIGNFLVWFQQKP
GKAPKSLIYAASRLQSGVPSRFSGSGSGTDFTLTISSLQPE
DFATYYCQHYKSYPLTFGGGTKVEIKR

M114
VH (SEQ ID NO: 209)
Q V Q L V Q S G A E V K K P G S S V K V S C K A S G G T F S S
Y A I S W V R Q A P G Q G L E W M G G I I P I F G T A N Y A Q
K F Q G R V TI T A D E S T S T A Y M E L S S L R S E D T A V Y
Y C A R A G P V G A T T G T F D Y W G Q G T L V T V S S

VL (SEQ ID NO: 217)
DIVMTQSPGTLSLSPGERATLSCRASQSVSSSYLAWYQQ
KPGQAPRLLIYGASSRATGIPDRFSGSGSGTDFTLTISRLE
PEDFAVYYCQQYGSSFTFGPGTKVDIKR

M115
VH (SEQ ID NO: 225)
Q V Q L Q Q S G A E V K K P G S S V K V S C K A S G G T F R S
Y A I S W V R Q A P G Q G L E W M G G I I P I F G T A N Y A Q
K F Q G R V TI T A D E S T S T A Y M E L S S L R S E D T A V Y
Y C A R G S Q S Y D H Y Y Y Y G M D V W G Q G T T V T V S S

VL (SEQ ID NO: 233)
QSALTQPASVSGSPGQSITISCTGTSSDVGGYNYVSWYQQ
HPGKAPKLMIFDVSNRPSGVSNRLSGSKSGNTASLTISGL
QAEDEADYYCSSYTSNTVVFGGGTKLTVL

M116
VH (SEQ ID NO: 241)
E V Q L V Q S G A E V K K P G S S V K V S C K A S G G A F S S
Y A I S W V R Q A P G Q G L E W M G G I I P I F G T A N Y A Q
K F Q G R V TI T A D E S T S T A Y M E L S S L R S E D T A V Y
Y C A R D S A G L G A W G Q G T L V A V S S

VL (SEQ ID NO: 249)
DIQMTQSPSSLSASVGDRVTITCRASQGISSALAWYQQKP
GKAPKLLIYDASSLESGVPSRFSGSGSGTDFTLTISSLQPE
DFATYYCQQFNSYPLTFGQGTRLEIKR

Fig. 8 (continued)

M117
VH (SEQ ID NO: 257)
Q I T L K E S G P T L V K P T Q T L T L T C T F S G F S L S T S G
V G V G W I R Q P P G K A L E W L A L I Y W D D D K R Y S P S
L K S R L T I T K D T S K N Q V V L T M T N M D P V D T A T Y
Y C A H R E S G P E F F Q H W G Q G T L V T V S S

VL (SEQ ID NO: 265)
D V V M T Q S P L S L P V T L G Q P A S I S C N S S Q S L V Y S N G I T Y L N W
F H Q R P G Q S P R R L I Y Q V S N W D S E V P D R F S G S G S A T D F T L K I
S R V E A D D V G I Y Y C M Q G T H W P P T F G Q G T R L E I K R

9 m102 mutants Sequences:

M102.2
VH (SEQ ID NO: 273)
E V Q V I Q S G A D V K K P G S S V K V S C K S S G G T F S K Y A I N W V R Q
A P G Q G L E W M G G I I P I L G I A N Y A Q K F Q G R V T I T T D E S T S T A
Y M E L S S L R S E D T A V Y Y C A R G W G R E Q L A P H P S Q Y Y Y Y Y Y
G M D V W G Q G T T V T V S S

VL (SEQ ID NO: 281)
E I V M T Q S P G T L S L S P G E R A T L S C R A S Q S V A S R Y L A W Y Q H
K P G L A P R L L I Y G A S T R A T G I P D R F S G S G S G T D F T L T I S R L E
P E D F A V Y Y C Q Q Y G R T P S V T F G G G T K V E I K R

M102.3
VH (SEQ ID NO: 289)
E V Q V I Q S G A D V K K P G S S V K V S C K S S G G T F S K Y A I N W V R Q
A P G Q G L E W M G G I I P I L G I A N Y A Q K F Q G R V T I T T D E S T S T A
Y M E L S S L R S E D T A V Y Y C A R G W G R E Q L A P H P S Q Y Y Y Y Y Y
G M D V W G Q G T T V T V S S

VL (SEQ ID NO: 297)
E I V M T Q S P G T P S L S P G E R A T L S C R A S Q S I R S T Y L A W Y Q Q K
P G Q A P R L L I Y G A S S R A T G I P D R F S G S G S G T D F T L T I S R L E P
E D F A V Y Y C Q Q Y G R S P S F G Q G T K V E I K R

VH (SEQ ID NO: 305)

EVQVIQSGADVKKPGSSVKVSCKSSGGTFSKYAINWVRQ
APGQGLEWMGGIIPILGIANYAQKFQGRVTITTDESTSTA
YMELSSLRSEDTAVYYCARGWGREQLAPHPSQYYYYYY
GMDVWGQGTTVTVSS

VL (SEQ ID NO: 313)

EIVMTQSPGTLSLAPGERATLSCWASQSVRNNYLAWYQQ
KPGQAPRLVIYNGSTRATGIPDRFSGSGSGTDFTLTISRLD
PEDFAVYYCQQYGNSRRVTFGGGTKVEIKR

M102.5

VH (SEQ ID NO: 321)

EVQVIQSGADVKKPGSSVKVSCKSSGGTFSKYAINWVRQ
APGQGLEWMGGIIPILGIANYAQKFQGRVTITTDESTSTA
YMELSSLRSEDTAVYYCARGWGREQLAPHPSQYYYYYY
GMDVWGQGTTVTVSS

VL (SEQ ID NO: 329)

EIVLTQSPGTLSLSPGERATLSCRASQSVSSSYLAWYQQK
PGQAPRLLIYGTSTRATGIPDRFSGSGSGTDFTLTISRLEP
EDFAVYYCQRYGSSPAFGQGTKVEIKR

M102.11

VH (SEQ ID NO: 337)

EVQVIQSGADVKKPGSSVKVSCKSSGGTFSKYAINWVRQ
APGQGLEWMGGIIPILGIANYAQKFQGRVTITTDESTSTA
YMELSSLRSEDTAVYYCARGWGREQLAPHPSQYYYYYY
GMDVWGQGTTVTVSS

VL (SEQ ID NO: 345)

DIQMTQSPATLSASIGDRVTITCRASQSISKWLAWYQQKP
GKAPKLLIYKASTLESGVPSRFSGSGSGTDFTLTISSLQPD
DFATYYCQQYINYATFGQGTKVEIKR

M102.12

VH (SEQ ID NO: 353)

EVQVIQSGADVKKPGSSVKVSCKSSGGTFSKYAINWVRQ
APGQGLEWMGGIIPILGIANYAQKFQGRVTITTDESTSTA
YMELSSLRSEDTAVYYCARGWGREQLAPHPSQYYYYYY
GMDVWGQGTTVTVSS

Fig. 8 (continued)

VL (SEQ ID NO: 361)
EIVMTQSPGTLSLAPGERATLSCWASQSVRNNYLAWYQQ
KPGQAPRLVIYNGSTRATGIPDRFSGSGSGTDFTLTISRLD
PEDFAVYYCQQYGNSRRVTFGGGTKVEIKR

M102.13
VH (SEQ ID NO: 369)
EVQVIQSGADVKKPGSSVKVSCKSSGGTFSKYAINWVRQ
APGQGLEWMGGIIPILGIANYAQKFQGRVTITTDESTSTA
YMELSSLRSEDTAVYYCARGWGREQLAPHPSQYYYYYY
GMDVWGQGTTVTVSS

VL (SEQ ID NO: 377)
EIVLTQSPATLSLSPGERATLSCRASQSVSSYLAWYQQKPGQ
APRLLIYDASNRATGIPARFSGSGSGTDFTLTISSLEPEDFAV
YYCQQRSNWPTFGQGTKVEIKR

M102.15
VH (SEQ ID NO: 385)
EVQVIQSGADVKKPGSSVKVSCKSSGGTFSKYAINWVRQ
APGQGLEWMGGIIPILGIANYAQKFQGRVTITTDESTSTA
YMELSSLRSEDTAVYYCARGWGREQLAPHPSQYYYYYY
GMDVWGQGTTVTVSS

VL (SEQ ID NO: 393)
EIVLTQSPGTLSLSPGERATLSCRASQSVSSSYLAWYQQKP
GQAPRLLIYGASSRATGIPDRFSGSGSGTDFTLTISRLEPEDF
AVYYCQQYGSSPTITFGQGTRLEIKR

M102.16
VH (SEQ ID NO: 401)
EVQVIQSGADVKKPGSSVKVSCKSSGGTFSKYAINWVRQ
APGQGLEWMGGIIPILGIANYAQKFQGRVTITTDESTSTA
YMELSSLRSEDTAVYYCARGWGREQLAPHPSQYYYYYY
GMDVWGQGTTVTVSS

VL (SEQ ID NO: 409)
EIVLTQSPGTLSLSPGERATLSCRASQSVSSSYLAWYQQKP
GQAPRLLIYGASSRATGIPDRFSGSGSGTDFTLTISRLEPEDF
AVYYCQQYGSSPVFGQGTKLEIKR

Fig. 8 (continued7)

```
                          SEQUENCE LISTING


<160> NUMBER OF SEQ ID NOS: 416

<210> SEQ ID NO 1
<211> LENGTH: 127
<212> TYPE: PRT
<213> ORGANISM: Homo sapiens

<400> SEQUENCE: 1

Gln Val Gln Leu Val Gln Ser Gly Ala Glu Val Lys Lys Pro Gly Ala
 1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Gly Asp Thr Ala Val Tyr Tyr Cys
                85                  90                  95

Ala Arg Asp Pro Gly Gly Tyr Ser Tyr Gly Pro Tyr Tyr Tyr Tyr Tyr
            100                 105                 110

Gly Met Asp Val Trp Gly Gln Gly Thr Thr Val Thr Val Ser Ser
        115                 120                 125


<210> SEQ ID NO 2
<211> LENGTH: 25
<212> TYPE: PRT
<213> ORGANISM: Homo sapiens

<400> SEQUENCE: 2

Gln Val Gln Leu Val Gln Ser Gly Ala Glu Val Lys Lys Pro Gly Ala
 1               5                  10                  15

Ser Val Lys Val Ser Cys Lys Ala Ser
            20                  25


<210> SEQ ID NO 3
<211> LENGTH: 8
<212> TYPE: PRT
<213> ORGANISM: Homo sapiens
```

-continued

<400> SEQUENCE: 3

Gly Gly Thr Phe Ser Ser Tyr Ala
1 5

<210> SEQ ID NO 4
<211> LENGTH: 18
<212> TYPE: PRT
<213> ORGANISM: Homo sapiens

<400> SEQUENCE: 4

Ile Ser Trp Val Arg Gln Ala Pro Gly Gln Gly Leu Glu Trp Met Gly
1 5 10 15

Gly Ile

<210> SEQ ID NO 5
<211> LENGTH: 7
<212> TYPE: PRT
<213> ORGANISM: Homo sapiens

<400> SEQUENCE: 5

Ile Pro Ile Phe Gly Thr Ala
1 5

<210> SEQ ID NO 6
<211> LENGTH: 38
<212> TYPE: PRT
<213> ORGANISM: Homo sapiens

<400> SEQUENCE: 6

Asn Tyr Ala Gln Lys Phe Gln Gly Arg Val Thr Ile Thr Ala Asp Glu
1 5 10 15

Ser Thr Ser Thr Ala Tyr Met Glu Leu Ser Ser Leu Arg Ser Gly Asp
20 25 30

Thr Ala Val Tyr Tyr Cys
35

<210> SEQ ID NO 7
<211> LENGTH: 20
<212> TYPE: PRT
<213> ORGANISM: Homo sapiens

<400> SEQUENCE: 7

Ala Arg Asp Pro Gly Gly Tyr Ser Tyr Gly Pro Tyr Tyr Tyr Tyr Tyr
1 5 10 15

Gly Met Asp Val
20

<210> SEQ ID NO 8
<211> LENGTH: 11
<212> TYPE: PRT
<213> ORGANISM: Homo sapiens

<400> SEQUENCE: 8

Trp Gly Gln Gly Thr Thr Val Thr Val Ser Ser
1 5 10

<210> SEQ ID NO 9
<211> LENGTH: 111
<212> TYPE: PRT
<213> ORGANISM: Homo sapiens

<400> SEQUENCE: 9

Asp Ile Gln Met Thr Gln Ser Pro Ser Ser Val Ser Ala Ser Val Gly

-continued

```
 1               5                   10                  15

Asp Arg Val Thr Ile Thr Cys Arg Ala Ser Gln Gly Ile Gly Pro Trp
            20                  25                  30

Leu Ala Trp Tyr Gln Gln Lys Pro Gly Lys Ala Pro Lys Phe Leu Ile
        35                  40                  45

Tyr Arg Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala His Ser Phe Pro Phe
                85                  90                  95

Thr Phe Gly Pro Gly Thr Lys Val Asp Ile Lys Arg Thr Val Ala
            100                 105                 110


<210> SEQ ID NO 10
<211> LENGTH: 26
<212> TYPE: PRT
<213> ORGANISM: Homo sapiens

<400> SEQUENCE: 10

Asp Ile Gln Met Thr Gln Ser Pro Ser Ser Val Ser Ala Ser Val Gly
 1               5                   10                  15

Asp Arg Val Thr Ile Thr Cys Arg Ala Ser
            20                  25


<210> SEQ ID NO 11
<211> LENGTH: 6
<212> TYPE: PRT
<213> ORGANISM: Homo sapiens

<400> SEQUENCE: 11

Gln Gly Ile Gly Pro Trp
 1               5


<210> SEQ ID NO 12
<211> LENGTH: 17
<212> TYPE: PRT
<213> ORGANISM: Homo sapiens

<400> SEQUENCE: 12

Leu Ala Trp Tyr Gln Gln Lys Pro Gly Lys Ala Pro Lys Phe Leu Ile
 1               5                   10                  15

Tyr


<210> SEQ ID NO 13
<211> LENGTH: 3
<212> TYPE: PRT
<213> ORGANISM: Homo sapiens

<400> SEQUENCE: 13

Arg Ala Ser
 1


<210> SEQ ID NO 14
<211> LENGTH: 36
<212> TYPE: PRT
<213> ORGANISM: Homo sapiens

<400> SEQUENCE: 14

Thr Leu Gln Ser Gly Val Pro Ser Arg Phe Ser Gly Ser Gly Ser Gly
 1               5                   10                  15
```

```
Thr Asp Phe Thr Leu Thr Ile Ser Ser Leu Gln Pro Glu Asp Phe Ala
            20                  25                  30

Thr Tyr Tyr Cys
        35


<210> SEQ ID NO 15
<211> LENGTH: 9
<212> TYPE: PRT
<213> ORGANISM: Homo sapiens

<400> SEQUENCE: 15

Gln Gln Ala His Ser Phe Pro Phe Thr
1               5


<210> SEQ ID NO 16
<211> LENGTH: 14
<212> TYPE: PRT
<213> ORGANISM: Homo sapiens

<400> SEQUENCE: 16

Phe Gly Pro Gly Thr Lys Val Asp Ile Lys Arg Thr Val Ala
1               5                   10


<210> SEQ ID NO 17
<211> LENGTH: 132
<212> TYPE: PRT
<213> ORGANISM: Homo sapiens

<400> SEQUENCE: 17

Glu Val Gln Leu Val Gln Ser Gly Ala Glu Val Lys Lys Pro Gly Ser
1               5                   10                  15

Ser Val Lys Val Ser Cys Lys Ser Ser Gly Gly Thr Phe Ser Asn Tyr
            20                  25                  30

Ala Ile Asn Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
    50                  55                  60

Gln Gly Arg Val Thr Ile Thr Thr Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Trp Gly Arg Glu Gln Leu Ala Pro His Pro Ser Gln Tyr
            100                 105                 110

Tyr Tyr Tyr Tyr Tyr Gly Met Asp Val Trp Gly Gln Gly Thr Thr Val
        115                 120                 125

Thr Val Ser Ser
    130


<210> SEQ ID NO 18
<211> LENGTH: 25
<212> TYPE: PRT
<213> ORGANISM: Homo sapiens

<400> SEQUENCE: 18

Glu Val Gln Leu Val Gln Ser Gly Ala Glu Val Lys Lys Pro Gly Ser
1               5                   10                  15

Ser Val Lys Val Ser Cys Lys Ser Ser
            20                  25


<210> SEQ ID NO 19
<211> LENGTH: 8
```

<212> TYPE: PRT
<213> ORGANISM: Homo sapiens

<400> SEQUENCE: 19

Gly Gly Thr Phe Ser Asn Tyr Ala
1 5

<210> SEQ ID NO 20
<211> LENGTH: 18
<212> TYPE: PRT
<213> ORGANISM: Homo sapiens

<400> SEQUENCE: 20

Ile Asn Trp Val Arg Gln Ala Pro Gly Gln Gly Leu Glu Trp Met Gly
1 5 10 15

Gly Ile

<210> SEQ ID NO 21
<211> LENGTH: 7
<212> TYPE: PRT
<213> ORGANISM: Homo sapiens

<400> SEQUENCE: 21

Ile Pro Ile Leu Gly Ile Ala
1 5

<210> SEQ ID NO 22
<211> LENGTH: 38
<212> TYPE: PRT
<213> ORGANISM: Homo sapiens

<400> SEQUENCE: 22

Asn Tyr Ala Gln Lys Phe Gln Gly Arg Val Thr Ile Thr Thr Asp Glu
1 5 10 15

Ser Thr Ser Thr Ala Tyr Met Glu Leu Ser Ser Leu Arg Ser Glu Asp
20 25 30

Thr Ala Val Tyr Tyr Cys
35

<210> SEQ ID NO 23
<211> LENGTH: 25
<212> TYPE: PRT
<213> ORGANISM: Homo sapiens

<400> SEQUENCE: 23

Ala Arg Gly Trp Gly Arg Glu Gln Leu Ala Pro His Pro Ser Gln Tyr
1 5 10 15

Tyr Tyr Tyr Tyr Tyr Gly Met Asp Val
20 25

<210> SEQ ID NO 24
<211> LENGTH: 11
<212> TYPE: PRT
<213> ORGANISM: Homo sapiens

<400> SEQUENCE: 24

Trp Gly Gln Gly Thr Thr Val Thr Val Ser Ser
1 5 10

<210> SEQ ID NO 25
<211> LENGTH: 111
<212> TYPE: PRT
<213> ORGANISM: Homo sapiens

<400> SEQUENCE: 25

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Ile Thr Asn Gly
20 25 30

Arg Leu Ala Trp Tyr Gln Gln Lys Pro Gly Gln Ala Pro Arg Leu Leu
35 40 45

Ile Tyr Gly Val Ser Ser Arg Ala Ser Gly Ile Pro Glu Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Ser Val
85 90 95

Leu Phe Gly Pro Gly Thr Lys Val Asp Ile Lys Arg Thr Val Ala
100 105 110

<210> SEQ ID NO 26
<211> LENGTH: 26
<212> TYPE: PRT
<213> ORGANISM: Homo sapiens

<400> SEQUENCE: 26

Glu Ile Val Leu Thr Gln Ser Pro Gly Thr Leu Ser Leu Ser Pro Gly
1 5 10 15

Glu Arg Ala Thr Leu Ser Cys Arg Ala Ser
20 25

<210> SEQ ID NO 27
<211> LENGTH: 7
<212> TYPE: PRT
<213> ORGANISM: Homo sapiens

<400> SEQUENCE: 27

Gln Ser Ile Thr Asn Gly Arg
1 5

<210> SEQ ID NO 28
<211> LENGTH: 17
<212> TYPE: PRT
<213> ORGANISM: Homo sapiens

<400> SEQUENCE: 28

Leu Ala Trp Tyr Gln Gln Lys Pro Gly Gln Ala Pro Arg Leu Leu Ile
1 5 10 15

Tyr

<210> SEQ ID NO 29
<211> LENGTH: 3
<212> TYPE: PRT
<213> ORGANISM: Homo sapiens

<400> SEQUENCE: 29

Gly Val Ser
1

<210> SEQ ID NO 30
<211> LENGTH: 36
<212> TYPE: PRT
<213> ORGANISM: Homo sapiens

<400> SEQUENCE: 30

Ser Arg Ala Ser Gly Ile Pro Glu Arg Phe Ser Gly Ser Gly Ser Gly
1 5 10 15

Thr Asp Phe Thr Leu Thr Ile Ser Arg Leu Glu Pro Glu Asp Phe Ala
20 25 30

Val Tyr Tyr Cys
35

<210> SEQ ID NO 31
<211> LENGTH: 8
<212> TYPE: PRT
<213> ORGANISM: Homo sapiens

<400> SEQUENCE: 31

Gln Gln Tyr Gly Ser Ser Val Leu
1 5

<210> SEQ ID NO 32
<211> LENGTH: 14
<212> TYPE: PRT
<213> ORGANISM: Homo sapiens

<400> SEQUENCE: 32

Phe Gly Pro Gly Thr Lys Val Asp Ile Lys Arg Thr Val Ala
1 5 10

<210> SEQ ID NO 33
<211> LENGTH: 118
<212> TYPE: PRT
<213> ORGANISM: Homo sapiens

<400> SEQUENCE: 33

Glu Val Gln Leu Val Glu Ser Gly Gly Gly Leu Ile Gln Pro Gly Gly
1 5 10 15

Ser Leu Arg Leu Ser Cys Ala Ala Ser Gly Phe Thr Val Ser Ser Asn
20 25 30

Tyr Met Ser Trp Val Arg Gln Ala Pro Gly Lys Gly Leu Glu Trp Val
35 40 45

Ser Val Ile Tyr Ser Gly Gly Ser Thr Tyr Tyr Ala Asp Ser Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Asp Ser Arg Tyr His Asp Ala Phe Asp Ile Trp Gly Gln Gly Thr
100 105 110

Met Val Thr Val Ser Ser
115

<210> SEQ ID NO 34
<211> LENGTH: 25
<212> TYPE: PRT
<213> ORGANISM: Homo sapiens

<400> SEQUENCE: 34

Glu Val Gln Leu Val Glu Ser Gly Gly Gly Leu Ile Gln Pro Gly Gly
1 5 10 15

Ser Leu Arg Leu Ser Cys Ala Ala Ser
20 25

<210> SEQ ID NO 35
<211> LENGTH: 8

-continued

<212> TYPE: PRT
<213> ORGANISM: Homo sapiens

<400> SEQUENCE: 35

Gly Phe Thr Val Ser Ser Asn Tyr
1 5

<210> SEQ ID NO 36
<211> LENGTH: 18
<212> TYPE: PRT
<213> ORGANISM: Homo sapiens

<400> SEQUENCE: 36

Met Ser Trp Val Arg Gln Ala Pro Gly Lys Gly Leu Glu Trp Val Ser
1 5 10 15

Val Ile

<210> SEQ ID NO 37
<211> LENGTH: 6
<212> TYPE: PRT
<213> ORGANISM: Homo sapiens

<400> SEQUENCE: 37

Tyr Ser Gly Gly Ser Thr
1 5

<210> SEQ ID NO 38
<211> LENGTH: 38
<212> TYPE: PRT
<213> ORGANISM: Homo sapiens

<400> SEQUENCE: 38

Tyr Tyr Ala Asp Ser Val Lys Gly Arg Phe Thr Ile Ser Arg Asp Asn
1 5 10 15

Ser Lys Asn Thr Leu Tyr Leu Gln Met Asn Ser Leu Arg Ala Glu Asp
20 25 30

Thr Ala Val Tyr Tyr Cys
35

<210> SEQ ID NO 39
<211> LENGTH: 12
<212> TYPE: PRT
<213> ORGANISM: Homo sapiens

<400> SEQUENCE: 39

Ala Arg Asp Ser Arg Tyr His Asp Ala Phe Asp Ile
1 5 10

<210> SEQ ID NO 40
<211> LENGTH: 11
<212> TYPE: PRT
<213> ORGANISM: Homo sapiens

<400> SEQUENCE: 40

Trp Gly Gln Gly Thr Met Val Thr Val Ser Ser
1 5 10

<210> SEQ ID NO 41
<211> LENGTH: 116
<212> TYPE: PRT
<213> ORGANISM: Homo sapiens

<400> SEQUENCE: 41

Asp Val Val Met Thr Gln Ser Pro Leu Ser Leu Pro Val Thr Pro Gly

-continued

```
 1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Leu Tyr Thr Phe Gly Gln Gly Thr Lys Leu Glu Ile Lys
            100                 105                 110

Arg Thr Val Ala
        115


<210> SEQ ID NO 42
<211> LENGTH: 26
<212> TYPE: PRT
<213> ORGANISM: Homo sapiens

<400> SEQUENCE: 42

Asp Val Val Met Thr Gln Ser Pro Leu Ser Leu Pro Val Thr Pro Gly
 1               5                   10                  15

Glu Pro Ala Ser Ile Ser Cys Arg Ser Ser
            20                  25


<210> SEQ ID NO 43
<211> LENGTH: 11
<212> TYPE: PRT
<213> ORGANISM: Homo sapiens

<400> SEQUENCE: 43

Gln Ser Leu Leu His Ser Asn Gly Tyr Asn Tyr
 1               5                   10


<210> SEQ ID NO 44
<211> LENGTH: 17
<212> TYPE: PRT
<213> ORGANISM: Homo sapiens

<400> SEQUENCE: 44

Leu Asp Trp Tyr Leu Gln Lys Pro Gly Gln Ser Pro Gln Leu Leu Ile
 1               5                   10                  15

Tyr


<210> SEQ ID NO 45
<211> LENGTH: 3
<212> TYPE: PRT
<213> ORGANISM: Homo sapiens

<400> SEQUENCE: 45

Leu Gly Ser
 1


<210> SEQ ID NO 46
<211> LENGTH: 36
<212> TYPE: PRT
<213> ORGANISM: Homo sapiens

<400> SEQUENCE: 46
```

```
Asn Arg Ala Ser Gly Val Pro Asp Arg Phe Ser Gly Ser Gly Ser Gly
 1               5                  10                  15

Thr Asp Phe Thr Leu Lys Ile Ser Arg Val Glu Ala Glu Asp Val Gly
            20                  25                  30

Val Tyr Tyr Cys
        35


<210> SEQ ID NO 47
<211> LENGTH: 9
<212> TYPE: PRT
<213> ORGANISM: Homo sapiens

<400> SEQUENCE: 47

Met Gln Ala Leu Gln Thr Leu Tyr Thr
 1               5


<210> SEQ ID NO 48
<211> LENGTH: 14
<212> TYPE: PRT
<213> ORGANISM: Homo sapiens

<400> SEQUENCE: 48

Phe Gly Gln Gly Thr Lys Leu Glu Ile Lys Arg Thr Val Ala
 1               5                  10


<210> SEQ ID NO 49
<211> LENGTH: 119
<212> TYPE: PRT
<213> ORGANISM: Homo sapiens

<400> SEQUENCE: 49

Gln Val Gln Leu Gln Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Ser Trp Leu Asp Ala Phe Asp Ile Trp Gly Gln Gly
            100                 105                 110

Thr Met Val Thr Val Ser Ser
        115


<210> SEQ ID NO 50
<211> LENGTH: 25
<212> TYPE: PRT
<213> ORGANISM: Homo sapiens

<400> SEQUENCE: 50

Gln Val Gln Leu Gln Gln Ser Gly Ala Glu Val Lys Lys Pro Gly Ser
 1               5                  10                  15

Ser Val Lys Val Ser Cys Lys Ala Ser
            20                  25


<210> SEQ ID NO 51
<211> LENGTH: 8
```

<212> TYPE: PRT
<213> ORGANISM: Homo sapiens

<400> SEQUENCE: 51

Gly Gly Thr Phe Ser Ser Tyr Ala
1 5

<210> SEQ ID NO 52
<211> LENGTH: 19
<212> TYPE: PRT
<213> ORGANISM: Homo sapiens

<400> SEQUENCE: 52

Ile Ser Trp Val Arg Gln Ala Pro Gly Gln Gly Leu Glu Trp Met Gly
1 5 10 15

Gly Ile Ile

<210> SEQ ID NO 53
<211> LENGTH: 6
<212> TYPE: PRT
<213> ORGANISM: Homo sapiens

<400> SEQUENCE: 53

Pro Ile Phe Gly Thr Ala
1 5

<210> SEQ ID NO 54
<211> LENGTH: 38
<212> TYPE: PRT
<213> ORGANISM: Homo sapiens

<400> SEQUENCE: 54

Asn Tyr Ala Gln Lys Phe Gln Gly Arg Val Thr Ile Thr Ala Asp Glu
1 5 10 15

Ser Thr Ser Thr Ala Tyr Met Glu Leu Ser Ser Leu Arg Ser Glu Asp
20 25 30

Thr Ala Val Tyr Tyr Cys
35

<210> SEQ ID NO 55
<211> LENGTH: 12
<212> TYPE: PRT
<213> ORGANISM: Homo sapiens

<400> SEQUENCE: 55

Ala Arg Glu Ser Ser Trp Leu Asp Ala Phe Asp Ile
1 5 10

<210> SEQ ID NO 56
<211> LENGTH: 11
<212> TYPE: PRT
<213> ORGANISM: Homo sapiens

<400> SEQUENCE: 56

Trp Gly Gln Gly Thr Met Val Thr Val Ser Ser
1 5 10

<210> SEQ ID NO 57
<211> LENGTH: 116
<212> TYPE: PRT
<213> ORGANISM: Homo sapiens

<400> SEQUENCE: 57

Asp Val Val Met Thr Gln Ser Pro Leu Ser Leu Ser Val Thr Ala Gly

-continued

```
 1               5                   10                  15

Glu Pro Ala Ser Ile Ser Cys Arg Ser Ser Gln Ser Leu Leu His Ser
            20                  25                  30

Asn Gly His Ile Tyr Leu Asp Trp Tyr Leu Gln Lys Pro Gly Gln Ser
        35                  40                  45

Pro Gln Leu Leu Ile Tyr Met Ala Ser Asn Arg Ala Ser Gly Val Pro
    50                  55                  60

Asp Arg Phe Ser Gly Ser Gly Ser Gly Thr Asp Phe Thr Leu Arg Ile
65                  70                  75                  80

Asn Arg Val Glu Thr Glu Asp Val Gly Ile Tyr Tyr Cys Met Gln Ser
                85                  90                  95

Leu His Thr Thr Arg Thr Phe Gly Gln Gly Thr Lys Val Glu Ile Lys
            100                 105                 110

Arg Thr Val Ala
        115


<210> SEQ ID NO 58
<211> LENGTH: 26
<212> TYPE: PRT
<213> ORGANISM: Homo sapiens

<400> SEQUENCE: 58

Asp Val Val Met Thr Gln Ser Pro Leu Ser Leu Ser Val Thr Ala Gly
 1               5                   10                  15

Glu Pro Ala Ser Ile Ser Cys Arg Ser Ser
            20                  25


<210> SEQ ID NO 59
<211> LENGTH: 11
<212> TYPE: PRT
<213> ORGANISM: Homo sapiens

<400> SEQUENCE: 59

Gln Ser Leu Leu His Ser Asn Gly His Ile Tyr
 1               5                   10


<210> SEQ ID NO 60
<211> LENGTH: 17
<212> TYPE: PRT
<213> ORGANISM: Homo sapiens

<400> SEQUENCE: 60

Leu Asp Trp Tyr Leu Gln Lys Pro Gly Gln Ser Pro Gln Leu Leu Ile
 1               5                   10                  15

Tyr


<210> SEQ ID NO 61
<211> LENGTH: 3
<212> TYPE: PRT
<213> ORGANISM: Homo sapiens

<400> SEQUENCE: 61

Met Ala Ser
 1


<210> SEQ ID NO 62
<211> LENGTH: 36
<212> TYPE: PRT
<213> ORGANISM: Homo sapiens

<400> SEQUENCE: 62
```

Asn Arg Ala Ser Gly Val Pro Asp Arg Phe Ser Gly Ser Gly Ser Gly
1 5 10 15

Thr Asp Phe Thr Leu Arg Ile Asn Arg Val Glu Thr Glu Asp Val Gly
20 25 30

Ile Tyr Tyr Cys
35

<210> SEQ ID NO 63
<211> LENGTH: 9
<212> TYPE: PRT
<213> ORGANISM: Homo sapiens

<400> SEQUENCE: 63

Met Gln Ser Leu His Thr Thr Arg Thr
1 5

<210> SEQ ID NO 64
<211> LENGTH: 14
<212> TYPE: PRT
<213> ORGANISM: Homo sapiens

<400> SEQUENCE: 64

Phe Gly Gln Gly Thr Lys Val Glu Ile Lys Arg Thr Val Ala
1 5 10

<210> SEQ ID NO 65
<211> LENGTH: 122
<212> TYPE: PRT
<213> ORGANISM: Homo sapiens

<400> SEQUENCE: 65

Gln Val Gln Leu Val Gln Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Ala Met His Trp Val Arg Gln Ala Pro Gly Lys Gly Leu Glu Trp Val
35 40 45

Ala Val Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Val Gly Gly Ile Thr Gly Thr Ala Asp Ala Phe Asp Ile Trp
100 105 110

Gly Gln Gly Thr Met Val Thr Val Ser Ser
115 120

<210> SEQ ID NO 66
<211> LENGTH: 24
<212> TYPE: PRT
<213> ORGANISM: Homo sapiens

<400> SEQUENCE: 66

Gln Val Gln Leu Val Gln Ser Gly Gly Gly Val Val Gln Pro Gly Arg
1 5 10 15

Ser Leu Arg Leu Ser Cys Ala Ala
20

<210> SEQ ID NO 67
<211> LENGTH: 9

<212> TYPE: PRT
<213> ORGANISM: Homo sapiens

<400> SEQUENCE: 67

Ser Gly Phe Thr Phe Ser Ser Tyr Ala
1 5

<210> SEQ ID NO 68
<211> LENGTH: 18
<212> TYPE: PRT
<213> ORGANISM: Homo sapiens

<400> SEQUENCE: 68

Met His Trp Val Arg Gln Ala Pro Gly Lys Gly Leu Glu Trp Val Ala
1 5 10 15

Val Ile

<210> SEQ ID NO 69
<211> LENGTH: 7
<212> TYPE: PRT
<213> ORGANISM: Homo sapiens

<400> SEQUENCE: 69

Ser Tyr Asp Gly Ser Asn Lys
1 5

<210> SEQ ID NO 70
<211> LENGTH: 40
<212> TYPE: PRT
<213> ORGANISM: Homo sapiens

<400> SEQUENCE: 70

Tyr Tyr Ala Asp Ser Val Lys Gly Arg Phe Thr Ile Ser Arg Asp Asn
1 5 10 15

Ser Lys Asn Thr Leu Tyr Leu Gln Met Asn Ser Leu Arg Ala Glu Asp
20 25 30

Thr Ala Val Tyr Tyr Cys Ala Arg
35 40

<210> SEQ ID NO 71
<211> LENGTH: 13
<212> TYPE: PRT
<213> ORGANISM: Homo sapiens

<400> SEQUENCE: 71

Val Gly Gly Ile Thr Gly Thr Ala Asp Ala Phe Asp Ile
1 5 10

<210> SEQ ID NO 72
<211> LENGTH: 11
<212> TYPE: PRT
<213> ORGANISM: Homo sapiens

<400> SEQUENCE: 72

Trp Gly Gln Gly Thr Met Val Thr Val Ser Ser
1 5 10

<210> SEQ ID NO 73
<211> LENGTH: 116
<212> TYPE: PRT
<213> ORGANISM: Homo sapiens

<400> SEQUENCE: 73

Asp Val Val Met Thr Gln Ser Pro Leu Ser Leu Pro Val Thr Leu Gly

```
 1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Phe Thr Phe Gly Pro Gly Thr Lys Val Asp Ile Lys
            100                 105                 110

Arg Thr Val Ala
        115


<210> SEQ ID NO 74
<211> LENGTH: 26
<212> TYPE: PRT
<213> ORGANISM: Homo sapiens

<400> SEQUENCE: 74

Asp Val Val Met Thr Gln Ser Pro Leu Ser Leu Pro Val Thr Leu Gly
 1               5                   10                  15

Gln Pro Ala Ser Ile Ser Cys Arg Ser Ser
            20                  25


<210> SEQ ID NO 75
<211> LENGTH: 11
<212> TYPE: PRT
<213> ORGANISM: Homo sapiens

<400> SEQUENCE: 75

Gln Ser Leu Val Tyr Ser Asp Gly Asn Thr Tyr
 1               5                   10


<210> SEQ ID NO 76
<211> LENGTH: 17
<212> TYPE: PRT
<213> ORGANISM: Homo sapiens

<400> SEQUENCE: 76

Leu Asn Trp Phe Gln Gln Arg Pro Gly Gln Ser Pro Arg Arg Leu Ile
 1               5                   10                  15

Tyr


<210> SEQ ID NO 77
<211> LENGTH: 3
<212> TYPE: PRT
<213> ORGANISM: Homo sapiens

<400> SEQUENCE: 77

Lys Val Ser
 1


<210> SEQ ID NO 78
<211> LENGTH: 36
<212> TYPE: PRT
<213> ORGANISM: Homo sapiens

<400> SEQUENCE: 78
```

```
Asn Arg Asp Ser Gly Val Pro Asp Arg Phe Ser Gly Ser Gly Ser Gly
 1               5                  10                  15

Thr Asp Phe Thr Leu Lys Ile Ser Arg Val Glu Ala Glu Asp Val Gly
            20                  25                  30

Val Tyr Tyr Cys
        35


<210> SEQ ID NO 79
<211> LENGTH: 9
<212> TYPE: PRT
<213> ORGANISM: Homo sapiens

<400> SEQUENCE: 79

Met Gln Gly Thr His Trp Pro Phe Thr
 1               5


<210> SEQ ID NO 80
<211> LENGTH: 14
<212> TYPE: PRT
<213> ORGANISM: Homo sapiens

<400> SEQUENCE: 80

Phe Gly Pro Gly Thr Lys Val Asp Ile Lys Arg Thr Val Ala
 1               5                  10


<210> SEQ ID NO 81
<211> LENGTH: 131
<212> TYPE: PRT
<213> ORGANISM: Homo sapiens

<400> SEQUENCE: 81

Gln Val Gln Leu Gln Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gln Leu Ala Gly Tyr Tyr Tyr Asp Ser Ser Gly Tyr His
            100                 105                 110

Tyr Tyr Tyr Tyr Gly Met Asp Val Trp Gly Gln Gly Thr Thr Val Thr
        115                 120                 125

Val Ser Ser
    130


<210> SEQ ID NO 82
<211> LENGTH: 25
<212> TYPE: PRT
<213> ORGANISM: Homo sapiens

<400> SEQUENCE: 82

Gln Val Gln Leu Gln Gln Ser Gly Ala Glu Val Lys Lys Pro Gly Ser
 1               5                  10                  15

Ser Val Lys Val Ser Cys Lys Ala Ser
            20                  25
```

<210> SEQ ID NO 83
<211> LENGTH: 8
<212> TYPE: PRT
<213> ORGANISM: Homo sapiens

<400> SEQUENCE: 83

```
Gly Gly Thr Phe Ser Ser Tyr Ala
 1               5
```

<210> SEQ ID NO 84
<211> LENGTH: 18
<212> TYPE: PRT
<213> ORGANISM: Homo sapiens

<400> SEQUENCE: 84

```
Ile Ser Trp Val Arg Gln Ala Pro Gly Gln Gly Leu Glu Trp Met Gly
 1               5                  10                  15

Gly Ile
```

<210> SEQ ID NO 85
<211> LENGTH: 7
<212> TYPE: PRT
<213> ORGANISM: Homo sapiens

<400> SEQUENCE: 85

```
Ile Pro Ile Phe Gly Thr Ala
 1               5
```

<210> SEQ ID NO 86
<211> LENGTH: 38
<212> TYPE: PRT
<213> ORGANISM: Homo sapiens

<400> SEQUENCE: 86

```
Asn Tyr Ala Gln Lys Phe Gln Gly Arg Val Thr Ile Thr Ala Asp Lys
 1               5                  10                  15

Ser Thr Ser Thr Ala Tyr Met Glu Leu Ser Ser Leu Arg Ser Glu Asp
            20                  25                  30

Thr Ala Val Tyr Tyr Cys
        35
```

<210> SEQ ID NO 87
<211> LENGTH: 24
<212> TYPE: PRT
<213> ORGANISM: Homo sapiens

<400> SEQUENCE: 87

```
Ala Arg Asp Gln Leu Ala Gly Tyr Tyr Tyr Asp Ser Ser Gly Tyr His
 1               5                  10                  15

Tyr Tyr Tyr Tyr Gly Met Asp Val
            20
```

<210> SEQ ID NO 88
<211> LENGTH: 11
<212> TYPE: PRT
<213> ORGANISM: Homo sapiens

<400> SEQUENCE: 88

```
Trp Gly Gln Gly Thr Thr Val Thr Val Ser Ser
 1               5                  10
```

<210> SEQ ID NO 89
<211> LENGTH: 111

<212> TYPE: PRT
<213> ORGANISM: Homo sapiens

<400> SEQUENCE: 89

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys Arg Thr Val Ala
            100                 105                 110
```

<210> SEQ ID NO 90
<211> LENGTH: 26
<212> TYPE: PRT
<213> ORGANISM: Homo sapiens

<400> SEQUENCE: 90

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser
            20                  25
```

<210> SEQ ID NO 91
<211> LENGTH: 6
<212> TYPE: PRT
<213> ORGANISM: Homo sapiens

<400> SEQUENCE: 91

```
Gln Ser Ile Ser Ser Tyr
 1               5
```

<210> SEQ ID NO 92
<211> LENGTH: 17
<212> TYPE: PRT
<213> ORGANISM: Homo sapiens

<400> SEQUENCE: 92

```
Leu Asn Trp Tyr Gln Gln Lys Pro Gly Lys Ala Pro Lys Leu Leu Ile
 1               5                  10                  15

Tyr
```

<210> SEQ ID NO 93
<211> LENGTH: 3
<212> TYPE: PRT
<213> ORGANISM: Homo sapiens

<400> SEQUENCE: 93

```
Ala Ala Ser
 1
```

<210> SEQ ID NO 94
<211> LENGTH: 36
<212> TYPE: PRT
<213> ORGANISM: Homo sapiens -continued

<400> SEQUENCE: 94

Ser Leu Gln Ser Gly Val Pro Ser Arg Phe Ser Gly Ser Gly Ser Gly
1 5 10 15

Thr Asp Phe Thr Leu Thr Ile Ser Ser Leu Gln Pro Glu Asp Phe Ala
20 25 30

Thr Tyr Tyr Cys
35

<210> SEQ ID NO 95
<211> LENGTH: 9
<212> TYPE: PRT
<213> ORGANISM: Homo sapiens

<400> SEQUENCE: 95

Gln Gln Ser Tyr Ser Thr Pro Ile Thr
1 5

<210> SEQ ID NO 96
<211> LENGTH: 14
<212> TYPE: PRT
<213> ORGANISM: Homo sapiens

<400> SEQUENCE: 96

Phe Gly Gln Gly Thr Arg Leu Glu Ile Lys Arg Thr Val Ala
1 5 10

<210> SEQ ID NO 97
<211> LENGTH: 120
<212> TYPE: PRT
<213> ORGANISM: Homo sapiens

<400> SEQUENCE: 97

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Ile Ile Asn Pro Ser Gly Gly Ser Thr Ser Tyr Ala Gln Lys Phe
50 55 60

Gln Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Asp His Val His Gly Pro Asp Ala Phe Asp Ile Trp Gly Gln
100 105 110

Gly Thr Met Val Thr Val Ser Ser
115 120

<210> SEQ ID NO 98
<211> LENGTH: 24
<212> TYPE: PRT
<213> ORGANISM: Homo sapiens

<400> SEQUENCE: 98

Glu Val Gln Leu Val Gln Ser Gly Ala Glu Val Lys Lys Pro Gly Ala
1 5 10 15

Ser Val Lys Val Ser Cys Lys Ala
20

<210> SEQ ID NO 99
<211> LENGTH: 9
<212> TYPE: PRT
<213> ORGANISM: Homo sapiens

<400> SEQUENCE: 99

Ser Gly Tyr Thr Phe Thr Gly Tyr Tyr
1 5

<210> SEQ ID NO 100
<211> LENGTH: 17
<212> TYPE: PRT
<213> ORGANISM: Homo sapiens

<400> SEQUENCE: 100

Met His Trp Val Arg Gln Ala Pro Gly Gln Gly Leu Glu Trp Met Gly
1 5 10 15

Ile

<210> SEQ ID NO 101
<211> LENGTH: 8
<212> TYPE: PRT
<213> ORGANISM: Homo sapiens

<400> SEQUENCE: 101

Ile Asn Pro Ser Gly Gly Ser Thr
1 5

<210> SEQ ID NO 102
<211> LENGTH: 38
<212> TYPE: PRT
<213> ORGANISM: Homo sapiens

<400> SEQUENCE: 102

Ser Tyr Ala Gln Lys Phe Gln Gly Arg Val Thr Met Thr Arg Asp Thr
1 5 10 15

Ser Thr Ser Thr Val Tyr Met Glu Leu Ser Ser Leu Arg Ser Glu Asp
20 25 30

Thr Ala Val Tyr Tyr Cys
35

<210> SEQ ID NO 103
<211> LENGTH: 13
<212> TYPE: PRT
<213> ORGANISM: Homo sapiens

<400> SEQUENCE: 103

Ala Arg Asp His Val His Gly Pro Asp Ala Phe Asp Ile
1 5 10

<210> SEQ ID NO 104
<211> LENGTH: 11
<212> TYPE: PRT
<213> ORGANISM: Homo sapiens

<400> SEQUENCE: 104

Trp Gly Gln Gly Thr Met Val Thr Val Ser Ser
1 5 10

<210> SEQ ID NO 105
<211> LENGTH: 114
<212> TYPE: PRT
<213> ORGANISM: Homo sapiens

<400> SEQUENCE: 105

Ser Tyr Glu Leu Thr Gln Pro Pro Ser Ala Ser Gly Thr Pro Gly Gln
1 5 10 15

Arg Val Thr Ile Ser Cys Ser Gly Ser Ser Ser Asn Ile Gly Ser Asn
20 25 30

Thr Val Asn Trp Tyr Gln Gln Leu Pro Gly Thr Ala Pro Lys Leu Leu
35 40 45

Ile Tyr Arg Asn Asn Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Ala Ala Trp Asp Asp Ser Leu
85 90 95

His Val Val Phe Gly Gly Gly Thr Lys Leu Thr Val Leu Gly Gln Pro
100 105 110

Lys Ala

<210> SEQ ID NO 106
<211> LENGTH: 25
<212> TYPE: PRT
<213> ORGANISM: Homo sapiens

<400> SEQUENCE: 106

Ser Tyr Glu Leu Thr Gln Pro Pro Ser Ala Ser Gly Thr Pro Gly Gln
1 5 10 15

Arg Val Thr Ile Ser Cys Ser Gly Ser
20 25

<210> SEQ ID NO 107
<211> LENGTH: 8
<212> TYPE: PRT
<213> ORGANISM: Homo sapiens

<400> SEQUENCE: 107

Ser Ser Asn Ile Gly Ser Asn Thr
1 5

<210> SEQ ID NO 108
<211> LENGTH: 17
<212> TYPE: PRT
<213> ORGANISM: Homo sapiens

<400> SEQUENCE: 108

Val Asn Trp Tyr Gln Gln Leu Pro Gly Thr Ala Pro Lys Leu Leu Ile
1 5 10 15

Tyr

<210> SEQ ID NO 109
<211> LENGTH: 3
<212> TYPE: PRT
<213> ORGANISM: Homo sapiens

<400> SEQUENCE: 109

Arg Asn Asn
1

<210> SEQ ID NO 110
<211> LENGTH: 36
<212> TYPE: PRT
<213> ORGANISM: Homo sapiens

<400> SEQUENCE: 110

```
Gln Arg Pro Ser Gly Val Pro Asp Arg Phe Ser Gly Ser Lys Ser Gly
 1               5                  10                  15

Thr Ser Ala Ser Leu Ala Ile Ser Gly Leu Gln Ser Glu Asp Glu Ala
            20                  25                  30

Asp Tyr Tyr Cys
        35
```

<210> SEQ ID NO 111
<211> LENGTH: 10
<212> TYPE: PRT
<213> ORGANISM: Homo sapiens

<400> SEQUENCE: 111

```
Ala Ala Trp Asp Asp Ser Leu His Val Val
 1               5                  10
```

<210> SEQ ID NO 112
<211> LENGTH: 15
<212> TYPE: PRT
<213> ORGANISM: Homo sapiens

<400> SEQUENCE: 112

```
Phe Gly Gly Gly Thr Lys Leu Thr Val Leu Gly Gln Pro Lys Ala
 1               5                  10                  15
```

<210> SEQ ID NO 113
<211> LENGTH: 116
<212> TYPE: PRT
<213> ORGANISM: Homo sapiens

<400> SEQUENCE: 113

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Gly Ala Phe Asp Ile Trp Gly Gln Gly Thr Met Val
            100                 105                 110

Thr Val Ser Ser
        115
```

<210> SEQ ID NO 114
<211> LENGTH: 25
<212> TYPE: PRT
<213> ORGANISM: Homo sapiens

<400> SEQUENCE: 114

```
Glu Val Gln Leu Val Glu Ser Gly Gly Gly Leu Val Lys Pro Gly Gly
 1               5                  10                  15

Ser Leu Arg Leu Ser Cys Ala Ala Ser
            20                  25
```

<210> SEQ ID NO 115
<211> LENGTH: 8
<212> TYPE: PRT
<213> ORGANISM: Homo sapiens

<400> SEQUENCE: 115

Gly Phe Thr Phe Ser Asp Tyr Tyr
1 5

<210> SEQ ID NO 116
<211> LENGTH: 17
<212> TYPE: PRT
<213> ORGANISM: Homo sapiens

<400> SEQUENCE: 116

Met Ser Trp Ile Arg Gln Ala Pro Gly Lys Gly Leu Glu Trp Val Ser
1 5 10 15

Tyr

<210> SEQ ID NO 117
<211> LENGTH: 8
<212> TYPE: PRT
<213> ORGANISM: Homo sapiens

<400> SEQUENCE: 117

Ile Ser Ser Ser Gly Ser Thr Ile
1 5

<210> SEQ ID NO 118
<211> LENGTH: 38
<212> TYPE: PRT
<213> ORGANISM: Homo sapiens

<400> SEQUENCE: 118

Tyr Tyr Ala Asp Ser Val Lys Gly Arg Phe Thr Ile Ser Arg Asp Asn
1 5 10 15

Ala Lys Asn Ser Leu Tyr Leu Gln Met Asn Ser Leu Arg Ala Glu Asp
20 25 30

Thr Ala Val Tyr Tyr Cys
35

<210> SEQ ID NO 119
<211> LENGTH: 9
<212> TYPE: PRT
<213> ORGANISM: Homo sapiens

<400> SEQUENCE: 119

Ala Arg Val Gly Gly Ala Phe Asp Ile
1 5

<210> SEQ ID NO 120
<211> LENGTH: 11
<212> TYPE: PRT
<213> ORGANISM: Homo sapiens

<400> SEQUENCE: 120

Trp Gly Gln Gly Thr Met Val Thr Val Ser Ser
1 5 10

<210> SEQ ID NO 121
<211> LENGTH: 112
<212> TYPE: PRT
<213> ORGANISM: Homo sapiens

<400> SEQUENCE: 121

```
Asn Phe Met Leu Thr Gln Pro His Ser Val Ser Gly Ser Pro Gly Lys
 1              5                   10                  15

Thr Val Thr Ile Ser Cys Thr Arg Ser Ser Gly Ser Ile Ala Ser Asn
            20                  25                  30

Tyr Val Gln Trp Tyr Arg Gln Ser Pro Gly Ser Ala Pro Thr Thr Val
        35                  40                  45

Ile Tyr Glu Gly Tyr Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Glu Thr Glu Asp Glu Ala Asp Tyr Tyr Cys Gln Ser Tyr Asp Ala
                85                  90                  95

Thr Asn His Gln Val Val Phe Gly Gly Gly Thr Lys Leu Thr Val Leu
            100                 105                 110


<210> SEQ ID NO 122
<211> LENGTH: 26
<212> TYPE: PRT
<213> ORGANISM: Homo sapiens

<400> SEQUENCE: 122

Asn Phe Met Leu Thr Gln Pro His Ser Val Ser Gly Ser Pro Gly Lys
 1              5                   10                  15

Thr Val Thr Ile Ser Cys Thr Arg Ser Ser
            20                  25


<210> SEQ ID NO 123
<211> LENGTH: 7
<212> TYPE: PRT
<213> ORGANISM: Homo sapiens

<400> SEQUENCE: 123

Gly Ser Ile Ala Ser Asn Tyr
 1              5


<210> SEQ ID NO 124
<211> LENGTH: 17
<212> TYPE: PRT
<213> ORGANISM: Homo sapiens

<400> SEQUENCE: 124

Val Gln Trp Tyr Arg Gln Ser Pro Gly Ser Ala Pro Thr Thr Val Ile
 1              5                   10                  15

Tyr


<210> SEQ ID NO 125
<211> LENGTH: 3
<212> TYPE: PRT
<213> ORGANISM: Homo sapiens

<400> SEQUENCE: 125

Glu Gly Tyr
 1


<210> SEQ ID NO 126
<211> LENGTH: 38
<212> TYPE: PRT
<213> ORGANISM: Homo sapiens

<400> SEQUENCE: 126

Gln Arg Pro Ser Gly Val Pro Asp Arg Phe Ser Gly Ser Ile Asp Ser
```

```
 1               5                   10                  15

Ser Ser Asn Ser Ala Ser Leu Thr Ile Ser Gly Leu Glu Thr Glu Asp
            20                  25                  30

Glu Ala Asp Tyr Tyr Cys
        35


<210> SEQ ID NO 127
<211> LENGTH: 11
<212> TYPE: PRT
<213> ORGANISM: Homo sapiens

<400> SEQUENCE: 127

Gln Ser Tyr Asp Ala Thr Asn His Gln Val Val
 1               5                   10


<210> SEQ ID NO 128
<211> LENGTH: 10
<212> TYPE: PRT
<213> ORGANISM: Homo sapiens

<400> SEQUENCE: 128

Phe Gly Gly Gly Thr Lys Leu Thr Val Leu
 1               5                   10


<210> SEQ ID NO 129
<211> LENGTH: 118
<212> TYPE: PRT
<213> ORGANISM: Homo sapiens

<400> SEQUENCE: 129

Gln Met Gln Leu Gln Gln Trp Gly Ala Gly Leu Leu Lys Pro Ser Glu
 1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Trp Phe Arg Asp Trp Tyr Phe Asp Leu Trp Gly Arg Gly Thr
            100                 105                 110

Leu Val Thr Val Ser Ser
        115


<210> SEQ ID NO 130
<211> LENGTH: 25
<212> TYPE: PRT
<213> ORGANISM: Homo sapiens

<400> SEQUENCE: 130

Gln Met Gln Leu Gln Gln Trp Gly Ala Gly Leu Leu Lys Pro Ser Glu
 1               5                   10                  15

Thr Leu Ser Leu Thr Cys Ala Val Tyr
            20                  25


<210> SEQ ID NO 131
<211> LENGTH: 8
<212> TYPE: PRT
```

<213> ORGANISM: Homo sapiens

<400> SEQUENCE: 131

Gly Gly Ser Phe Ser Gly Tyr Tyr
1 5

<210> SEQ ID NO 132
<211> LENGTH: 17
<212> TYPE: PRT
<213> ORGANISM: Homo sapiens

<400> SEQUENCE: 132

Trp Ser Trp Ile Arg Gln Pro Pro Gly Lys Gly Leu Glu Trp Ile Gly
1 5 10 15

Glu

<210> SEQ ID NO 133
<211> LENGTH: 7
<212> TYPE: PRT
<213> ORGANISM: Homo sapiens

<400> SEQUENCE: 133

Ile Asn His Ser Gly Ser Thr
1 5

<210> SEQ ID NO 134
<211> LENGTH: 38
<212> TYPE: PRT
<213> ORGANISM: Homo sapiens

<400> SEQUENCE: 134

Asn Tyr Asn Pro Ser Leu Lys Ser Arg Val Thr Ile Ser Val Asp Thr
1 5 10 15

Ser Lys Asn Gln Phe Ser Leu Lys Leu Ser Ser Val Thr Ala Ala Asp
20 25 30

Thr Ala Val Tyr Tyr Cys
35

<210> SEQ ID NO 135
<211> LENGTH: 12
<212> TYPE: PRT
<213> ORGANISM: Homo sapiens

<400> SEQUENCE: 135

Ala Arg Gly Trp Phe Arg Asp Trp Tyr Phe Asp Leu
1 5 10

<210> SEQ ID NO 136
<211> LENGTH: 11
<212> TYPE: PRT
<213> ORGANISM: Homo sapiens

<400> SEQUENCE: 136

Trp Gly Arg Gly Thr Leu Val Thr Val Ser Ser
1 5 10

<210> SEQ ID NO 137
<211> LENGTH: 108
<212> TYPE: PRT
<213> ORGANISM: Homo sapiens

<400> SEQUENCE: 137

Asp Ile Gln Met Thr Gln Ser Pro Ser Ser Leu Ser Ala Ser Val Gly
1 5 10 15

-continued

```
Asp Arg Val Thr Ile Thr Cys Arg Ala Ser Gln Asp Ile Arg Asn Asp
            20                  25                  30

Leu Gly Trp Tyr Gln Gln Arg Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Phe Cys Leu Gln Asp Tyr Gln Tyr Pro Trp
                85                  90                  95

Thr Phe Gly Gln Gly Thr Lys Val Glu Ile Lys Arg
            100                 105


<210> SEQ ID NO 138
<211> LENGTH: 26
<212> TYPE: PRT
<213> ORGANISM: Homo sapiens

<400> SEQUENCE: 138

Asp Ile Gln Met Thr Gln Ser Pro Ser Ser Leu Ser Ala Ser Val Gly
 1               5                  10                  15

Asp Arg Val Thr Ile Thr Cys Arg Ala Ser
            20                  25


<210> SEQ ID NO 139
<211> LENGTH: 6
<212> TYPE: PRT
<213> ORGANISM: Homo sapiens

<400> SEQUENCE: 139

Gln Asp Ile Arg Asn Asp
 1               5


<210> SEQ ID NO 140
<211> LENGTH: 17
<212> TYPE: PRT
<213> ORGANISM: Homo sapiens

<400> SEQUENCE: 140

Leu Gly Trp Tyr Gln Gln Arg Pro Gly Lys Ala Pro Lys Leu Leu Ile
 1               5                  10                  15

Tyr


<210> SEQ ID NO 141
<211> LENGTH: 3
<212> TYPE: PRT
<213> ORGANISM: Homo sapiens

<400> SEQUENCE: 141

Ala Ala Ser
 1


<210> SEQ ID NO 142
<211> LENGTH: 36
<212> TYPE: PRT
<213> ORGANISM: Homo sapiens

<400> SEQUENCE: 142

Ser Leu Gln Ser Gly Val Pro Ser Arg Phe Ser Gly Ser Gly Ser Gly
 1               5                  10                  15

Thr Asp Phe Thr Leu Thr Ile Ser Ser Leu Gln Pro Glu Asp Ser Ala
```

-continued 20 25 30

Thr Tyr Phe Cys
35

<210> SEQ ID NO 143
<211> LENGTH: 9
<212> TYPE: PRT
<213> ORGANISM: Homo sapiens

<400> SEQUENCE: 143

Leu Gln Asp Tyr Gln Tyr Pro Trp Thr
1 5

<210> SEQ ID NO 144
<211> LENGTH: 11
<212> TYPE: PRT
<213> ORGANISM: Homo sapiens

<400> SEQUENCE: 144

Phe Gly Gln Gly Thr Lys Val Glu Ile Lys Arg
1 5 10

<210> SEQ ID NO 145
<211> LENGTH: 121
<212> TYPE: PRT
<213> ORGANISM: Homo sapiens

<400> SEQUENCE: 145

Glu Val Gln Leu Val Gln Ser Gly Gly Gly Leu Val Gln Pro Gly Arg
1 5 10 15

Ser Leu Arg Leu Ser Cys Ala Ala Ser Gly Phe Thr Phe Asp Asp Tyr
20 25 30

Ala Met His Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Ser Glu Gly Leu Pro Glu Thr Asp Asp Ala Phe Asp Ile Trp Gly
100 105 110

Gln Gly Thr Met Val Thr Val Ser Ser
115 120

<210> SEQ ID NO 146
<211> LENGTH: 25
<212> TYPE: PRT
<213> ORGANISM: Homo sapiens

<400> SEQUENCE: 146

Glu Val Gln Leu Val Gln Ser Gly Gly Gly Leu Val Gln Pro Gly Arg
1 5 10 15

Ser Leu Arg Leu Ser Cys Ala Ala Ser
20 25

<210> SEQ ID NO 147
<211> LENGTH: 8
<212> TYPE: PRT
<213> ORGANISM: Homo sapiens

<400> SEQUENCE: 147

Gly Phe Thr Phe Asp Asp Tyr Ala
1 5

<210> SEQ ID NO 148
<211> LENGTH: 17
<212> TYPE: PRT
<213> ORGANISM: Homo sapiens

<400> SEQUENCE: 148

Met His Trp Val Arg Gln Ala Pro Gly Lys Gly Leu Glu Trp Val Ser
1 5 10 15

Ala

<210> SEQ ID NO 149
<211> LENGTH: 8
<212> TYPE: PRT
<213> ORGANISM: Homo sapiens

<400> SEQUENCE: 149

Ile Ser Gly Ser Gly Gly Ser Thr
1 5

<210> SEQ ID NO 150
<211> LENGTH: 38
<212> TYPE: PRT
<213> ORGANISM: Homo sapiens

<400> SEQUENCE: 150

Tyr Tyr Ala Asp Ser Val Lys Gly Arg Phe Thr Ile Ser Arg Asp Asn
1 5 10 15

Ser Lys Asn Thr Leu Tyr Leu Gln Met Asn Ser Leu Arg Ala Glu Asp
20 25 30

Thr Ala Val Tyr Tyr Cys
35

<210> SEQ ID NO 151
<211> LENGTH: 14
<212> TYPE: PRT
<213> ORGANISM: Homo sapiens

<400> SEQUENCE: 151

Ala Ser Glu Gly Leu Pro Glu Thr Asp Asp Ala Phe Asp Ile
1 5 10

<210> SEQ ID NO 152
<211> LENGTH: 11
<212> TYPE: PRT
<213> ORGANISM: Homo sapiens

<400> SEQUENCE: 152

Trp Gly Gln Gly Thr Met Val Thr Val Ser Ser
1 5 10

<210> SEQ ID NO 153
<211> LENGTH: 113
<212> TYPE: PRT
<213> ORGANISM: Homo sapiens

<400> SEQUENCE: 153

Asp Val Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu Tyr Ser
20 25 30

```
Asp Gly Tyr Asn Tyr Leu Asp Trp Tyr Leu Gln Lys Pro Gly Gln Ser
        35                  40                  45

Pro Gln Leu Leu Ile Tyr Leu Gly Ser Arg Arg Ala Ser Gly Val Pro
    50                  55                  60

Asp Arg Phe Ser Gly Ser Gly Ser Gly Thr Asp Phe Thr Leu Lys Ile
65                  70                  75                  80

Asn Thr Val Glu Ala Glu Asp Val Gly Val Tyr Tyr Cys Met Gln Gly
                85                  90                  95

Val Glu Ile Pro Phe Thr Phe Gly Pro Gly Thr Lys Val Glu Ile Lys
            100                 105                 110

Arg


<210> SEQ ID NO 154
<211> LENGTH: 26
<212> TYPE: PRT
<213> ORGANISM: Homo sapiens

<400> SEQUENCE: 154

Asp Val Val Met Thr Gln Ser Pro Leu Ser Leu Pro Val Thr Pro Gly
 1               5                  10                  15

Glu Pro Ala Ser Ile Ser Cys Arg Ser Ser
            20                  25


<210> SEQ ID NO 155
<211> LENGTH: 11
<212> TYPE: PRT
<213> ORGANISM: Homo sapiens

<400> SEQUENCE: 155

Gln Ser Leu Leu Tyr Ser Asp Gly Tyr Asn Tyr
 1               5                  10


<210> SEQ ID NO 156
<211> LENGTH: 17
<212> TYPE: PRT
<213> ORGANISM: Homo sapiens

<400> SEQUENCE: 156

Leu Asp Trp Tyr Leu Gln Lys Pro Gly Gln Ser Pro Gln Leu Leu Ile
 1               5                  10                  15

Tyr


<210> SEQ ID NO 157
<211> LENGTH: 3
<212> TYPE: PRT
<213> ORGANISM: Homo sapiens

<400> SEQUENCE: 157

Leu Gly Ser
 1


<210> SEQ ID NO 158
<211> LENGTH: 36
<212> TYPE: PRT
<213> ORGANISM: Homo sapiens

<400> SEQUENCE: 158

Arg Arg Ala Ser Gly Val Pro Asp Arg Phe Ser Gly Ser Gly Ser Gly
 1               5                  10                  15

Thr Asp Phe Thr Leu Lys Ile Asn Thr Val Glu Ala Glu Asp Val Gly
            20                  25                  30
```

Val Tyr Tyr Cys
        35

<210> SEQ ID NO 159
<211> LENGTH: 9
<212> TYPE: PRT
<213> ORGANISM: Homo sapiens

<400> SEQUENCE: 159

Met Gln Gly Val Glu Ile Pro Phe Thr
 1               5

<210> SEQ ID NO 160
<211> LENGTH: 11
<212> TYPE: PRT
<213> ORGANISM: Homo sapiens

<400> SEQUENCE: 160

Phe Gly Pro Gly Thr Lys Val Glu Ile Lys Arg
 1               5                   10

<210> SEQ ID NO 161
<211> LENGTH: 114
<212> TYPE: PRT
<213> ORGANISM: Homo sapiens

<400> SEQUENCE: 161

Gln Val Gln Leu Val Gln Ser Gly Ala Glu Val Lys Lys Pro Gly Ala
 1               5                   10                  15

Thr Val Lys Ile Ser Cys Lys Val Ser Gly Tyr Thr Phe Thr Asp Tyr
            20                  25                  30

Tyr Met His Trp Val Gln Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Glu Gly Ala Asp Tyr Trp Gly Gln Gly Thr Leu Val Thr Val
            100                 105                 110

Ser Ser

<210> SEQ ID NO 162
<211> LENGTH: 25
<212> TYPE: PRT
<213> ORGANISM: Homo sapiens

<400> SEQUENCE: 162

Gln Val Gln Leu Val Gln Ser Gly Ala Glu Val Lys Lys Pro Gly Ala
 1               5                   10                  15

Thr Val Lys Ile Ser Cys Lys Val Ser
            20                  25

<210> SEQ ID NO 163
<211> LENGTH: 8
<212> TYPE: PRT
<213> ORGANISM: Homo sapiens

<400> SEQUENCE: 163

Gly Tyr Thr Phe Thr Asp Tyr Tyr

```
 1               5


<210> SEQ ID NO 164
<211> LENGTH: 17
<212> TYPE: PRT
<213> ORGANISM: Homo sapiens

<400> SEQUENCE: 164

Met His Trp Val Gln Gln Ala Pro Gly Lys Gly Leu Glu Trp Met Gly
 1               5                   10                  15

Leu


<210> SEQ ID NO 165
<211> LENGTH: 8
<212> TYPE: PRT
<213> ORGANISM: Homo sapiens

<400> SEQUENCE: 165

Val Asp Pro Glu Asp Gly Glu Thr
 1               5


<210> SEQ ID NO 166
<211> LENGTH: 38
<212> TYPE: PRT
<213> ORGANISM: Homo sapiens

<400> SEQUENCE: 166

Ile Tyr Ala Glu Lys Phe Gln Gly Arg Val Thr Ile Thr Ala Asp Thr
 1               5                   10                  15

Ser Thr Asp Thr Ala Tyr Met Glu Leu Ser Ser Leu Arg Ser Glu Asp
            20                  25                  30

Thr Ala Val Tyr Tyr Cys
        35


<210> SEQ ID NO 167
<211> LENGTH: 7
<212> TYPE: PRT
<213> ORGANISM: Homo sapiens

<400> SEQUENCE: 167

Ala Thr Glu Gly Ala Asp Tyr
 1               5


<210> SEQ ID NO 168
<211> LENGTH: 11
<212> TYPE: PRT
<213> ORGANISM: Homo sapiens

<400> SEQUENCE: 168

Trp Gly Gln Gly Thr Leu Val Thr Val Ser Ser
 1               5                   10


<210> SEQ ID NO 169
<211> LENGTH: 114
<212> TYPE: PRT
<213> ORGANISM: Homo sapiens

<400> SEQUENCE: 169

Asp Val Val Met Thr Gln Ser Pro Leu Ser Leu Pro Val Ala Leu Gly
 1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
```

-continued

```
        35                  40                  45

Pro Arg Arg Leu Leu Tyr Lys Val Ser Asn Arg Glu Ser Gly Val Pro
    50                  55                  60

Asp Arg Phe Ser Gly Ser Gly Ser Gly Ser Asp Phe Thr Leu Lys Ile
65                  70                  75                  80

Ser Arg Val Glu Ala Glu Asp Val Gly Ile Tyr Tyr Cys Met Gln Gly
                85                  90                  95

Thr His Trp Pro Pro Ile Thr Phe Gly Gln Gly Thr Arg Leu Glu Ile
            100                 105                 110

Lys Arg


<210> SEQ ID NO 170
<211> LENGTH: 26
<212> TYPE: PRT
<213> ORGANISM: Homo sapiens

<400> SEQUENCE: 170

Asp Val Val Met Thr Gln Ser Pro Leu Ser Leu Pro Val Ala Leu Gly
 1               5                  10                  15

Gln Pro Ala Ser Ile Ser Cys Arg Ser Ser
            20                  25


<210> SEQ ID NO 171
<211> LENGTH: 11
<212> TYPE: PRT
<213> ORGANISM: Homo sapiens

<400> SEQUENCE: 171

Gln Ser Leu Val His Ser Asp Gly Asn Thr Tyr
 1               5                  10


<210> SEQ ID NO 172
<211> LENGTH: 17
<212> TYPE: PRT
<213> ORGANISM: Homo sapiens

<400> SEQUENCE: 172

Leu Asn Trp Phe Gln Gln Arg Pro Gly Gln Ser Pro Arg Arg Leu Leu
 1               5                  10                  15

Tyr


<210> SEQ ID NO 173
<211> LENGTH: 3
<212> TYPE: PRT
<213> ORGANISM: Homo sapiens

<400> SEQUENCE: 173

Lys Val Ser
 1


<210> SEQ ID NO 174
<211> LENGTH: 36
<212> TYPE: PRT
<213> ORGANISM: Homo sapiens

<400> SEQUENCE: 174

Asn Arg Glu Ser Gly Val Pro Asp Arg Phe Ser Gly Ser Gly Ser Gly
 1               5                  10                  15

Ser Asp Phe Thr Leu Lys Ile Ser Arg Val Glu Ala Glu Asp Val Gly
            20                  25                  30

Ile Tyr Tyr Cys
```

35

<210> SEQ ID NO 175
<211> LENGTH: 10
<212> TYPE: PRT
<213> ORGANISM: Homo sapiens

<400> SEQUENCE: 175

Met Gln Gly Thr His Trp Pro Pro Ile Thr
1 5 10

<210> SEQ ID NO 176
<211> LENGTH: 11
<212> TYPE: PRT
<213> ORGANISM: Homo sapiens

<400> SEQUENCE: 176

Phe Gly Gln Gly Thr Arg Leu Glu Ile Lys Arg
1 5 10

<210> SEQ ID NO 177
<211> LENGTH: 114
<212> TYPE: PRT
<213> ORGANISM: Homo sapiens

<400> SEQUENCE: 177

Gln Val Gln Leu Val Gln Ser Gly Ala Glu Val Lys Lys Pro Gly Ala
1 5 10 15

Thr Val Lys Ile Ser Cys Lys Val Ser Gly Tyr Thr Phe Thr Asp Tyr
20 25 30

Tyr Met His Trp Val Gln Gln Ala Pro Gly Lys Gly Leu Glu Trp Met
35 40 45

Gly Leu Val Asp Pro Glu Asp Gly Glu Thr Ile Tyr Ala Gln Lys Phe
50 55 60

Gln Gly Arg Val Thr Ile Thr Ala Asp Thr Ser Thr Asn Thr Ala Tyr
65 70 75 80

Met Glu Leu Ser Ser Leu Arg Ser Glu Asp Thr Ala Val Tyr Tyr Cys
85 90 95

Ala Thr Asp Gly Ala Asp Tyr Trp Asp Gln Gly Thr Leu Gly Thr Val
100 105 110

Ser Thr

<210> SEQ ID NO 178
<211> LENGTH: 25
<212> TYPE: PRT
<213> ORGANISM: Homo sapiens

<400> SEQUENCE: 178

Gln Val Gln Leu Val Gln Ser Gly Ala Glu Val Lys Lys Pro Gly Ala
1 5 10 15

Thr Val Lys Ile Ser Cys Lys Val Ser
20 25

<210> SEQ ID NO 179
<211> LENGTH: 8
<212> TYPE: PRT
<213> ORGANISM: Homo sapiens

<400> SEQUENCE: 179

Gly Tyr Thr Phe Thr Asp Tyr Tyr
1 5

<210> SEQ ID NO 180
<211> LENGTH: 18
<212> TYPE: PRT
<213> ORGANISM: Homo sapiens

<400> SEQUENCE: 180

Met His Trp Val Gln Gln Ala Pro Gly Lys Gly Leu Glu Trp Met Gly
1 5 10 15

Leu Val

<210> SEQ ID NO 181
<211> LENGTH: 8
<212> TYPE: PRT
<213> ORGANISM: Homo sapiens

<400> SEQUENCE: 181

Asp Pro Glu Asp Gly Glu Thr Ile
1 5

<210> SEQ ID NO 182
<211> LENGTH: 37
<212> TYPE: PRT
<213> ORGANISM: Homo sapiens

<400> SEQUENCE: 182

Tyr Ala Gln Lys Phe Gln Gly Arg Val Thr Ile Thr Ala Asp Thr Ser
1 5 10 15

Thr Asn Thr Ala Tyr Met Glu Leu Ser Ser Leu Arg Ser Glu Asp Thr
20 25 30

Ala Val Tyr Tyr Cys
35

<210> SEQ ID NO 183
<211> LENGTH: 7
<212> TYPE: PRT
<213> ORGANISM: Homo sapiens

<400> SEQUENCE: 183

Ala Thr Asp Gly Ala Asp Tyr
1 5

<210> SEQ ID NO 184
<211> LENGTH: 11
<212> TYPE: PRT
<213> ORGANISM: Homo sapiens

<400> SEQUENCE: 184

Trp Asp Gln Gly Thr Leu Gly Thr Val Ser Thr
1 5 10

<210> SEQ ID NO 185
<211> LENGTH: 111
<212> TYPE: PRT
<213> ORGANISM: Homo sapiens

<400> SEQUENCE: 185

Gln Ser Val Leu Thr Gln Pro Pro Ser Val Ser Gly Ala Pro Gly Gln
1 5 10 15

Thr Val Thr Ile Ser Cys Thr Gly Ser Ser Ser Asn Ile Gly Gly Asp
20 25 30

Ser Asp Val His Trp Tyr Gln Gln Leu Pro Gly Ser Ala Pro Lys Leu
35 40 45

```
Leu Ile Tyr Gly Asn Arg Asn Arg Pro Ser Gly Val Pro Asp Arg Phe
    50                  55                  60

Ser Gly Ser Arg Ser Gly Thr Ser Ala Ser Leu Ala Val Ile Gly Val
65                  70                  75                  80

Gln Ala Asp Asp Glu Ala Asp Tyr Tyr Cys Gln Cys Tyr Asp Ser Ser
                85                  90                  95

Leu Asn Gly Tyr Val Phe Gly Pro Gly Thr Lys Val Ile Val Leu
            100                 105                 110


<210> SEQ ID NO 186
<211> LENGTH: 26
<212> TYPE: PRT
<213> ORGANISM: Homo sapiens

<400> SEQUENCE: 186

Gln Ser Val Leu Thr Gln Pro Pro Ser Val Ser Gly Ala Pro Gly Gln
 1               5                  10                  15

Thr Val Thr Ile Ser Cys Thr Gly Ser Ser
            20                  25


<210> SEQ ID NO 187
<211> LENGTH: 8
<212> TYPE: PRT
<213> ORGANISM: Homo sapiens

<400> SEQUENCE: 187

Ser Asn Ile Gly Gly Asp Ser Asp
 1               5


<210> SEQ ID NO 188
<211> LENGTH: 17
<212> TYPE: PRT
<213> ORGANISM: Homo sapiens

<400> SEQUENCE: 188

Val His Trp Tyr Gln Gln Leu Pro Gly Ser Ala Pro Lys Leu Leu Ile
 1               5                  10                  15

Tyr


<210> SEQ ID NO 189
<211> LENGTH: 3
<212> TYPE: PRT
<213> ORGANISM: Homo sapiens

<400> SEQUENCE: 189

Gly Asn Arg
 1


<210> SEQ ID NO 190
<211> LENGTH: 36
<212> TYPE: PRT
<213> ORGANISM: Homo sapiens

<400> SEQUENCE: 190

Asn Arg Pro Ser Gly Val Pro Asp Arg Phe Ser Gly Ser Arg Ser Gly
 1               5                  10                  15

Thr Ser Ala Ser Leu Ala Val Ile Gly Val Gln Ala Asp Asp Glu Ala
            20                  25                  30

Asp Tyr Tyr Cys
        35


<210> SEQ ID NO 191
```

<211> LENGTH: 11
<212> TYPE: PRT
<213> ORGANISM: Homo sapiens

<400> SEQUENCE: 191

Gln Cys Tyr Asp Ser Ser Leu Asn Gly Tyr Val
1 5 10

<210> SEQ ID NO 192
<211> LENGTH: 10
<212> TYPE: PRT
<213> ORGANISM: Homo sapiens

<400> SEQUENCE: 192

Phe Gly Pro Gly Thr Lys Val Ile Val Leu
1 5 10

<210> SEQ ID NO 193
<211> LENGTH: 119
<212> TYPE: PRT
<213> ORGANISM: Homo sapiens

<400> SEQUENCE: 193

Gln Val Gln Leu Gln Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Trp Thr Asn Pro Asn Ser Gly Gly Thr Asn Tyr Ala Gln Lys Leu
50 55 60

Gln Gly Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Asn Tyr Lys Leu Gln Ser Asp Ala Phe Asp Ile Trp Gly Gln Gly
100 105 110

Thr Met Val Thr Val Ser Ser
115

<210> SEQ ID NO 194
<211> LENGTH: 25
<212> TYPE: PRT
<213> ORGANISM: Homo sapiens

<400> SEQUENCE: 194

Gln Val Gln Leu Gln Gln Ser Gly Ala Glu Val Lys Lys Pro Gly Ser
1 5 10 15

Ser Val Lys Val Ser Cys Lys Ala Ser
20 25

<210> SEQ ID NO 195
<211> LENGTH: 6
<212> TYPE: PRT
<213> ORGANISM: Homo sapiens

<400> SEQUENCE: 195

Gly Gly Thr Phe Ser Ser
1 5

<210> SEQ ID NO 196
<211> LENGTH: 20

<212> TYPE: PRT
<213> ORGANISM: Homo sapiens

<400> SEQUENCE: 196

Tyr Ala Ile Ser Trp Val Arg Gln Ala Pro Gly Gln Gly Leu Glu Trp
1 5 10 15

Met Gly Trp Thr
20

<210> SEQ ID NO 197
<211> LENGTH: 7
<212> TYPE: PRT
<213> ORGANISM: Homo sapiens

<400> SEQUENCE: 197

Asn Pro Asn Ser Gly Gly Thr
1 5

<210> SEQ ID NO 198
<211> LENGTH: 38
<212> TYPE: PRT
<213> ORGANISM: Homo sapiens

<400> SEQUENCE: 198

Asn Tyr Ala Gln Lys Leu Gln Gly Arg Val Thr Met Thr Thr Asp Thr
1 5 10 15

Ser Thr Ser Thr Ala Tyr Met Glu Leu Arg Ser Leu Arg Ser Asp Asp
20 25 30

Thr Ala Val Tyr Tyr Cys
35

<210> SEQ ID NO 199
<211> LENGTH: 12
<212> TYPE: PRT
<213> ORGANISM: Homo sapiens

<400> SEQUENCE: 199

Ala Asn Tyr Lys Leu Gln Ser Asp Ala Phe Asp Ile
1 5 10

<210> SEQ ID NO 200
<211> LENGTH: 11
<212> TYPE: PRT
<213> ORGANISM: Homo sapiens

<400> SEQUENCE: 200

Trp Gly Gln Gly Thr Met Val Thr Val Ser Ser
1 5 10

<210> SEQ ID NO 201
<211> LENGTH: 108
<212> TYPE: PRT
<213> ORGANISM: Homo sapiens

<400> SEQUENCE: 201

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Gly Asn Phe
20 25 30

Leu Val Trp Phe Gln Gln Lys Pro Gly Lys Ala Pro Lys Ser Leu Ile
35 40 45

Tyr Ala Ala Ser Arg Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln His Tyr Lys Ser Tyr Pro Leu
85 90 95

Thr Phe Gly Gly Gly Thr Lys Val Glu Ile Lys Arg
100 105

<210> SEQ ID NO 202
<211> LENGTH: 26
<212> TYPE: PRT
<213> ORGANISM: Homo sapiens

<400> SEQUENCE: 202

Asp Ile Gln Met Thr Gln Ser Pro Ser Ser Leu Ser Ala Ser Val Gly
1 5 10 15

Asp Arg Val Thr Ile Thr Cys Arg Ala Ser
20 25

<210> SEQ ID NO 203
<211> LENGTH: 7
<212> TYPE: PRT
<213> ORGANISM: Homo sapiens

<400> SEQUENCE: 203

Gln Asp Ile Gly Asn Phe Leu
1 5

<210> SEQ ID NO 204
<211> LENGTH: 16
<212> TYPE: PRT
<213> ORGANISM: Homo sapiens

<400> SEQUENCE: 204

Val Trp Phe Gln Gln Lys Pro Gly Lys Ala Pro Lys Ser Leu Ile Tyr
1 5 10 15

<210> SEQ ID NO 205
<211> LENGTH: 3
<212> TYPE: PRT
<213> ORGANISM: Homo sapiens

<400> SEQUENCE: 205

Ala Ala Ser
1

<210> SEQ ID NO 206
<211> LENGTH: 36
<212> TYPE: PRT
<213> ORGANISM: Homo sapiens

<400> SEQUENCE: 206

Arg Leu Gln Ser Gly Val Pro Ser Arg Phe Ser Gly Ser Gly Ser Gly
1 5 10 15

Thr Asp Phe Thr Leu Thr Ile Ser Ser Leu Gln Pro Glu Asp Phe Ala
20 25 30

Thr Tyr Tyr Cys
35

<210> SEQ ID NO 207
<211> LENGTH: 9
<212> TYPE: PRT
<213> ORGANISM: Homo sapiens

<400> SEQUENCE: 207

Gln His Tyr Lys Ser Tyr Pro Leu Thr
 1               5

<210> SEQ ID NO 208
<211> LENGTH: 11
<212> TYPE: PRT
<213> ORGANISM: Homo sapiens

<400> SEQUENCE: 208

Phe Gly Gly Gly Thr Lys Val Glu Ile Lys Arg
 1               5                  10

<210> SEQ ID NO 209
<211> LENGTH: 122
<212> TYPE: PRT
<213> ORGANISM: Homo sapiens

<400> SEQUENCE: 209

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Gly Pro Val Gly Ala Thr Thr Gly Thr Phe Asp Tyr Trp
            100                 105                 110

Gly Gln Gly Thr Leu Val Thr Val Ser Ser
        115                 120

<210> SEQ ID NO 210
<211> LENGTH: 25
<212> TYPE: PRT
<213> ORGANISM: Homo sapiens

<400> SEQUENCE: 210

Gln Val Gln Leu Val Gln Ser Gly Ala Glu Val Lys Lys Pro Gly Ser
 1               5                  10                  15

Ser Val Lys Val Ser Cys Lys Ala Ser
            20                  25

<210> SEQ ID NO 211
<211> LENGTH: 10
<212> TYPE: PRT
<213> ORGANISM: Homo sapiens

<400> SEQUENCE: 211

Gly Gly Thr Phe Ser Ser Tyr Ala Ile Ser
 1               5                  10

<210> SEQ ID NO 212
<211> LENGTH: 16
<212> TYPE: PRT
<213> ORGANISM: Homo sapiens

<400> SEQUENCE: 212

-continued

Trp Val Arg Gln Ala Pro Gly Gln Gly Leu Glu Trp Met Gly Gly Ile
1               5                   10                  15

<210> SEQ ID NO 213
<211> LENGTH: 7
<212> TYPE: PRT
<213> ORGANISM: Homo sapiens

<400> SEQUENCE: 213

Ile Pro Ile Phe Gly Thr Ala
1               5

<210> SEQ ID NO 214
<211> LENGTH: 38
<212> TYPE: PRT
<213> ORGANISM: Homo sapiens

<400> SEQUENCE: 214

Asn Tyr Ala Gln Lys Phe Gln Gly Arg Val Thr Ile Thr Ala Asp Glu
1               5                   10                  15

Ser Thr Ser Thr Ala Tyr Met Glu Leu Ser Ser Leu Arg Ser Glu Asp
            20                  25                  30

Thr Ala Val Tyr Tyr Cys
        35

<210> SEQ ID NO 215
<211> LENGTH: 15
<212> TYPE: PRT
<213> ORGANISM: Homo sapiens

<400> SEQUENCE: 215

Ala Arg Ala Gly Pro Val Gly Ala Thr Thr Gly Thr Phe Asp Tyr
1               5                   10                  15

<210> SEQ ID NO 216
<211> LENGTH: 11
<212> TYPE: PRT
<213> ORGANISM: Homo sapiens

<400> SEQUENCE: 216

Trp Gly Gln Gly Thr Leu Val Thr Val Ser Ser
1               5                   10

<210> SEQ ID NO 217
<211> LENGTH: 108
<212> TYPE: PRT
<213> ORGANISM: Homo sapiens

<400> SEQUENCE: 217

Asp Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Phe
                85                  90                  95

```
Thr Phe Gly Pro Gly Thr Lys Val Asp Ile Lys Arg
            100                 105


<210> SEQ ID NO 218
<211> LENGTH: 26
<212> TYPE: PRT
<213> ORGANISM: Homo sapiens

<400> SEQUENCE: 218

Asp Ile Val Met Thr Gln Ser Pro Gly Thr Leu Ser Leu Ser Pro Gly
 1               5                  10                  15

Glu Arg Ala Thr Leu Ser Cys Arg Ala Ser
            20                  25


<210> SEQ ID NO 219
<211> LENGTH: 6
<212> TYPE: PRT
<213> ORGANISM: Homo sapiens

<400> SEQUENCE: 219

Gln Ser Val Ser Ser Ser
 1               5


<210> SEQ ID NO 220
<211> LENGTH: 18
<212> TYPE: PRT
<213> ORGANISM: Homo sapiens

<400> SEQUENCE: 220

Tyr Leu Ala Trp Tyr Gln Gln Lys Pro Gly Gln Ala Pro Arg Leu Leu
 1               5                  10                  15

Ile Tyr


<210> SEQ ID NO 221
<211> LENGTH: 3
<212> TYPE: PRT
<213> ORGANISM: Homo sapiens

<400> SEQUENCE: 221

Gly Ala Ser
 1


<210> SEQ ID NO 222
<211> LENGTH: 36
<212> TYPE: PRT
<213> ORGANISM: Homo sapiens

<400> SEQUENCE: 222

Ser Arg Ala Thr Gly Ile Pro Asp Arg Phe Ser Gly Ser Gly Ser Gly
 1               5                  10                  15

Thr Asp Phe Thr Leu Thr Ile Ser Arg Leu Glu Pro Glu Asp Phe Ala
            20                  25                  30

Val Tyr Tyr Cys
        35


<210> SEQ ID NO 223
<211> LENGTH: 8
<212> TYPE: PRT
<213> ORGANISM: Homo sapiens

<400> SEQUENCE: 223

Gln Gln Tyr Gly Ser Ser Phe Thr
 1               5
```

<210> SEQ ID NO 224
<211> LENGTH: 11
<212> TYPE: PRT
<213> ORGANISM: Homo sapiens

<400> SEQUENCE: 224

Phe Gly Pro Gly Thr Lys Val Asp Ile Lys Arg
1 5 10

<210> SEQ ID NO 225
<211> LENGTH: 124
<212> TYPE: PRT
<213> ORGANISM: Homo sapiens

<400> SEQUENCE: 225

Gln Val Gln Leu Gln Gln Ser Gly Ala Glu Val Lys Lys Pro Gly Ser
1 5 10 15

Ser Val Lys Val Ser Cys Lys Ala Ser Gly Gly Thr Phe Arg Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Gly Ser Gln Ser Tyr Asp His Tyr Tyr Tyr Tyr Gly Met Asp
100 105 110

Val Trp Gly Gln Gly Thr Thr Val Thr Val Ser Ser
115 120

<210> SEQ ID NO 226
<211> LENGTH: 25
<212> TYPE: PRT
<213> ORGANISM: Homo sapiens

<400> SEQUENCE: 226

Gln Val Gln Leu Gln Gln Ser Gly Ala Glu Val Lys Lys Pro Gly Ser
1 5 10 15

Ser Val Lys Val Ser Cys Lys Ala Ser
20 25

<210> SEQ ID NO 227
<211> LENGTH: 8
<212> TYPE: PRT
<213> ORGANISM: Homo sapiens

<400> SEQUENCE: 227

Gly Gly Thr Phe Arg Ser Tyr Ala
1 5

<210> SEQ ID NO 228
<211> LENGTH: 18
<212> TYPE: PRT
<213> ORGANISM: Homo sapiens

<400> SEQUENCE: 228

Ile Ser Trp Val Arg Gln Ala Pro Gly Gln Gly Leu Glu Trp Met Gly
1 5 10 15

Gly Ile

<210> SEQ ID NO 229
<211> LENGTH: 7
<212> TYPE: PRT
<213> ORGANISM: Homo sapiens

<400> SEQUENCE: 229

Ile Pro Ile Phe Gly Thr Ala
1               5

<210> SEQ ID NO 230
<211> LENGTH: 38
<212> TYPE: PRT
<213> ORGANISM: Homo sapiens

<400> SEQUENCE: 230

Asn Tyr Ala Gln Lys Phe Gln Gly Arg Val Thr Ile Thr Ala Asp Glu
1               5                   10                  15

Ser Thr Ser Thr Ala Tyr Met Glu Leu Ser Ser Leu Arg Ser Glu Asp
            20                  25                  30

Thr Ala Val Tyr Tyr Cys
        35

<210> SEQ ID NO 231
<211> LENGTH: 17
<212> TYPE: PRT
<213> ORGANISM: Homo sapiens

<400> SEQUENCE: 231

Ala Arg Gly Ser Gln Ser Tyr Asp His Tyr Tyr Tyr Tyr Gly Met Asp
1               5                   10                  15

Val

<210> SEQ ID NO 232
<211> LENGTH: 11
<212> TYPE: PRT
<213> ORGANISM: Homo sapiens

<400> SEQUENCE: 232

Trp Gly Gln Gly Thr Thr Val Thr Val Ser Ser
1               5                   10

<210> SEQ ID NO 233
<211> LENGTH: 109
<212> TYPE: PRT
<213> ORGANISM: Homo sapiens

<400> SEQUENCE: 233

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Phe Asp Val Ser Asn Arg Pro Ser Gly Val Ser Asn Arg Leu
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Asn
                85                  90                  95

Thr Val Val Phe Gly Gly Gly Thr Lys Leu Thr Val Leu 100 105

<210> SEQ ID NO 234
<211> LENGTH: 26
<212> TYPE: PRT
<213> ORGANISM: Homo sapiens

<400> SEQUENCE: 234

Gln Ser Ala Leu Thr Gln Pro Ala Ser Val Ser Gly Ser Pro Gly Gln
1 5 10 15

Ser Ile Thr Ile Ser Cys Thr Gly Thr Ser
20 25

<210> SEQ ID NO 235
<211> LENGTH: 8
<212> TYPE: PRT
<213> ORGANISM: Homo sapiens

<400> SEQUENCE: 235

Ser Asp Val Gly Gly Tyr Asn Tyr
1 5

<210> SEQ ID NO 236
<211> LENGTH: 17
<212> TYPE: PRT
<213> ORGANISM: Homo sapiens

<400> SEQUENCE: 236

Val Ser Trp Tyr Gln Gln His Pro Gly Lys Ala Pro Lys Leu Met Ile
1 5 10 15

Phe

<210> SEQ ID NO 237
<211> LENGTH: 3
<212> TYPE: PRT
<213> ORGANISM: Homo sapiens

<400> SEQUENCE: 237

Asp Val Ser
1

<210> SEQ ID NO 238
<211> LENGTH: 36
<212> TYPE: PRT
<213> ORGANISM: Homo sapiens

<400> SEQUENCE: 238

Asn Arg Pro Ser Gly Val Ser Asn Arg Leu Ser Gly Ser Lys Ser Gly
1 5 10 15

Asn Thr Ala Ser Leu Thr Ile Ser Gly Leu Gln Ala Glu Asp Glu Ala
20 25 30

Asp Tyr Tyr Cys
35

<210> SEQ ID NO 239
<211> LENGTH: 9
<212> TYPE: PRT
<213> ORGANISM: Homo sapiens

<400> SEQUENCE: 239

Ser Ser Tyr Thr Ser Asn Thr Val Val
1 5

<210> SEQ ID NO 240
<211> LENGTH: 10
<212> TYPE: PRT
<213> ORGANISM: Homo sapiens

<400> SEQUENCE: 240

Phe Gly Gly Gly Thr Lys Leu Thr Val Leu
1 5 10

<210> SEQ ID NO 241
<211> LENGTH: 116
<212> TYPE: PRT
<213> ORGANISM: Homo sapiens

<400> SEQUENCE: 241

Glu Val Gln Leu Val Gln Ser Gly Ala Glu Val Lys Lys Pro Gly Ser
1 5 10 15

Ser Val Lys Val Ser Cys Lys Ala Ser Gly Gly Ala Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Ser Ala Gly Leu Gly Ala Trp Gly Gln Gly Thr Leu Val
100 105 110

Ala Val Ser Ser
115

<210> SEQ ID NO 242
<211> LENGTH: 25
<212> TYPE: PRT
<213> ORGANISM: Homo sapiens

<400> SEQUENCE: 242

Glu Val Gln Leu Val Gln Ser Gly Ala Glu Val Lys Lys Pro Gly Ser
1 5 10 15

Ser Val Lys Val Ser Cys Lys Ala Ser
20 25

<210> SEQ ID NO 243
<211> LENGTH: 8
<212> TYPE: PRT
<213> ORGANISM: Homo sapiens

<400> SEQUENCE: 243

Gly Gly Ala Phe Ser Ser Tyr Ala
1 5

<210> SEQ ID NO 244
<211> LENGTH: 18
<212> TYPE: PRT
<213> ORGANISM: Homo sapiens

<400> SEQUENCE: 244

Ile Ser Trp Val Arg Gln Ala Pro Gly Gln Gly Leu Glu Trp Met Gly
1 5 10 15

Gly Ile

<210> SEQ ID NO 245
<211> LENGTH: 7
<212> TYPE: PRT
<213> ORGANISM: Homo sapiens

<400> SEQUENCE: 245

Ile Pro Ile Phe Gly Thr Ala
1 5

<210> SEQ ID NO 246
<211> LENGTH: 38
<212> TYPE: PRT
<213> ORGANISM: Homo sapiens

<400> SEQUENCE: 246

Asn Tyr Ala Gln Lys Phe Gln Gly Arg Val Thr Ile Thr Ala Asp Glu
1 5 10 15

Ser Thr Ser Thr Ala Tyr Met Glu Leu Ser Ser Leu Arg Ser Glu Asp
20 25 30

Thr Ala Val Tyr Tyr Cys
35

<210> SEQ ID NO 247
<211> LENGTH: 9
<212> TYPE: PRT
<213> ORGANISM: Homo sapiens

<400> SEQUENCE: 247

Ala Arg Asp Ser Ala Gly Leu Gly Ala
1 5

<210> SEQ ID NO 248
<211> LENGTH: 11
<212> TYPE: PRT
<213> ORGANISM: Homo sapiens

<400> SEQUENCE: 248

Trp Gly Gln Gly Thr Leu Val Ala Val Ser Ser
1 5 10

<210> SEQ ID NO 249
<211> LENGTH: 108
<212> TYPE: PRT
<213> ORGANISM: Homo sapiens

<400> SEQUENCE: 249

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Ser Ser Ala
20 25 30

Leu Ala Trp Tyr Gln Gln Lys Pro Gly Lys Ala Pro Lys Leu Leu Ile
35 40 45

Tyr Asp Ala Ser Ser Leu Glu Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Phe Asn Ser Tyr Pro Leu
85 90 95

Thr Phe Gly Gln Gly Thr Arg Leu Glu Ile Lys Arg
100 105

<210> SEQ ID NO 250
<211> LENGTH: 26
<212> TYPE: PRT
<213> ORGANISM: Homo sapiens

<400> SEQUENCE: 250

Asp Ile Gln Met Thr Gln Ser Pro Ser Ser Leu Ser Ala Ser Val Gly
1 5 10 15

Asp Arg Val Thr Ile Thr Cys Arg Ala Ser
20 25

<210> SEQ ID NO 251
<211> LENGTH: 6
<212> TYPE: PRT
<213> ORGANISM: Homo sapiens

<400> SEQUENCE: 251

Gln Gly Ile Ser Ser Ala
1 5

<210> SEQ ID NO 252
<211> LENGTH: 17
<212> TYPE: PRT
<213> ORGANISM: Homo sapiens

<400> SEQUENCE: 252

Leu Ala Trp Tyr Gln Gln Lys Pro Gly Lys Ala Pro Lys Leu Leu Ile
1 5 10 15

Tyr

<210> SEQ ID NO 253
<211> LENGTH: 3
<212> TYPE: PRT
<213> ORGANISM: Homo sapiens

<400> SEQUENCE: 253

Asp Ala Ser
1

<210> SEQ ID NO 254
<211> LENGTH: 36
<212> TYPE: PRT
<213> ORGANISM: Homo sapiens

<400> SEQUENCE: 254

Ser Leu Glu Ser Gly Val Pro Ser Arg Phe Ser Gly Ser Gly Ser Gly
1 5 10 15

Thr Asp Phe Thr Leu Thr Ile Ser Ser Leu Gln Pro Glu Asp Phe Ala
20 25 30

Thr Tyr Tyr Cys
35

<210> SEQ ID NO 255
<211> LENGTH: 9
<212> TYPE: PRT
<213> ORGANISM: Homo sapiens

<400> SEQUENCE: 255

Gln Gln Phe Asn Ser Tyr Pro Leu Thr
1 5

<210> SEQ ID NO 256
<211> LENGTH: 11
<212> TYPE: PRT

<213> ORGANISM: Homo sapiens

<400> SEQUENCE: 256

Phe Gly Gln Gly Thr Arg Leu Glu Ile Lys Arg
1 5 10

<210> SEQ ID NO 257
<211> LENGTH: 120
<212> TYPE: PRT
<213> ORGANISM: Homo sapiens

<400> SEQUENCE: 257

Gln Ile Thr Leu Lys Glu Ser Gly Pro Thr Leu Val Lys Pro Thr Gln
1 5 10 15

Thr Leu Thr Leu Thr Cys Thr Phe Ser Gly Phe Ser Leu Ser Thr Ser
20 25 30

Gly Val Gly Val Gly Trp Ile Arg Gln Pro Pro Gly Lys Ala Leu Glu
35 40 45

Trp Leu Ala Leu Ile Tyr Trp Asp Asp Asp Lys Arg Tyr Ser Pro Ser
50 55 60

Leu Lys Ser Arg Leu Thr Ile Thr Lys Asp Thr Ser Lys Asn Gln Val
65 70 75 80

Val Leu Thr Met Thr Asn Met Asp Pro Val Asp Thr Ala Thr Tyr Tyr
85 90 95

Cys Ala His Arg Glu Ser Gly Pro Glu Phe Phe Gln His Trp Gly Gln
100 105 110

Gly Thr Leu Val Thr Val Ser Ser
115 120

<210> SEQ ID NO 258
<211> LENGTH: 25
<212> TYPE: PRT
<213> ORGANISM: Homo sapiens

<400> SEQUENCE: 258

Gln Ile Thr Leu Lys Glu Ser Gly Pro Thr Leu Val Lys Pro Thr Gln
1 5 10 15

Thr Leu Thr Leu Thr Cys Thr Phe Ser
20 25

<210> SEQ ID NO 259
<211> LENGTH: 10
<212> TYPE: PRT
<213> ORGANISM: Homo sapiens

<400> SEQUENCE: 259

Gly Phe Ser Leu Ser Thr Ser Gly Val Gly
1 5 10

<210> SEQ ID NO 260
<211> LENGTH: 17
<212> TYPE: PRT
<213> ORGANISM: Homo sapiens

<400> SEQUENCE: 260

Val Gly Trp Ile Arg Gln Pro Pro Gly Lys Ala Leu Glu Trp Leu Ala
1 5 10 15

Leu

<210> SEQ ID NO 261
<211> LENGTH: 8

<212> TYPE: PRT
<213> ORGANISM: Homo sapiens

<400> SEQUENCE: 261

Ile Tyr Trp Asp Asp Asp Lys Arg
 1               5

<210> SEQ ID NO 262
<211> LENGTH: 37
<212> TYPE: PRT
<213> ORGANISM: Homo sapiens

<400> SEQUENCE: 262

Tyr Ser Pro Ser Leu Lys Ser Arg Leu Thr Ile Thr Lys Asp Thr Ser
 1               5                  10                  15

Lys Asn Gln Val Val Leu Thr Met Thr Asn Met Asp Pro Val Asp Thr
            20                  25                  30

Ala Thr Tyr Tyr Cys
        35

<210> SEQ ID NO 263
<211> LENGTH: 12
<212> TYPE: PRT
<213> ORGANISM: Homo sapiens

<400> SEQUENCE: 263

Ala His Arg Glu Ser Gly Pro Glu Phe Phe Gln His
 1               5                  10

<210> SEQ ID NO 264
<211> LENGTH: 11
<212> TYPE: PRT
<213> ORGANISM: Homo sapiens

<400> SEQUENCE: 264

Trp Gly Gln Gly Thr Leu Val Thr Val Ser Ser
 1               5                  10

<210> SEQ ID NO 265
<211> LENGTH: 113
<212> TYPE: PRT
<213> ORGANISM: Homo sapiens

<400> SEQUENCE: 265

Asp Val Val Met Thr Gln Ser Pro Leu Ser Leu Pro Val Thr Leu Gly
 1               5                  10                  15

Gln Pro Ala Ser Ile Ser Cys Asn Ser Ser Gln Ser Leu Val Tyr Ser
            20                  25                  30

Asn Gly Ile Thr Tyr Leu Asn Trp Phe His Gln Arg Pro Gly Gln Ser
        35                  40                  45

Pro Arg Arg Leu Ile Tyr Gln Val Ser Asn Trp Asp Ser Glu Val Pro
    50                  55                  60

Asp Arg Phe Ser Gly Ser Gly Ser Ala Thr Asp Phe Thr Leu Lys Ile
65                  70                  75                  80

Ser Arg Val Glu Ala Asp Asp Val Gly Ile Tyr Tyr Cys Met Gln Gly
                85                  90                  95

Thr His Trp Pro Pro Thr Phe Gly Gln Gly Thr Arg Leu Glu Ile Lys
            100                 105                 110

Arg

<210> SEQ ID NO 266

-continued

<211> LENGTH: 26
<212> TYPE: PRT
<213> ORGANISM: Homo sapiens

<400> SEQUENCE: 266

Asp Val Val Met Thr Gln Ser Pro Leu Ser Leu Pro Val Thr Leu Gly
1 5 10 15

Gln Pro Ala Ser Ile Ser Cys Asn Ser Ser
20 25

<210> SEQ ID NO 267
<211> LENGTH: 11
<212> TYPE: PRT
<213> ORGANISM: Homo sapiens

<400> SEQUENCE: 267

Gln Ser Leu Val Tyr Ser Asn Gly Ile Thr Tyr
1 5 10

<210> SEQ ID NO 268
<211> LENGTH: 17
<212> TYPE: PRT
<213> ORGANISM: Homo sapiens

<400> SEQUENCE: 268

Leu Asn Trp Phe His Gln Arg Pro Gly Gln Ser Pro Arg Arg Leu Ile
1 5 10 15

Tyr

<210> SEQ ID NO 269
<211> LENGTH: 3
<212> TYPE: PRT
<213> ORGANISM: Homo sapiens

<400> SEQUENCE: 269

Gln Val Ser
1

<210> SEQ ID NO 270
<211> LENGTH: 36
<212> TYPE: PRT
<213> ORGANISM: Homo sapiens

<400> SEQUENCE: 270

Asn Trp Asp Ser Glu Val Pro Asp Arg Phe Ser Gly Ser Gly Ser Ala
1 5 10 15

Thr Asp Phe Thr Leu Lys Ile Ser Arg Val Glu Ala Asp Asp Val Gly
20 25 30

Ile Tyr Tyr Cys
35

<210> SEQ ID NO 271
<211> LENGTH: 9
<212> TYPE: PRT
<213> ORGANISM: Homo sapiens

<400> SEQUENCE: 271

Met Gln Gly Thr His Trp Pro Pro Thr
1 5

<210> SEQ ID NO 272
<211> LENGTH: 11
<212> TYPE: PRT
<213> ORGANISM: Homo sapiens

<400> SEQUENCE: 272

Phe Gly Gln Gly Thr Arg Leu Glu Ile Lys Arg
 1 5 10

<210> SEQ ID NO 273
<211> LENGTH: 132
<212> TYPE: PRT
<213> ORGANISM: Homo sapiens

<400> SEQUENCE: 273

Glu Val Gln Val Ile Gln Ser Gly Ala Asp Val Lys Lys Pro Gly Ser
 1 5 10 15

Ser Val Lys Val Ser Cys Lys Ser Ser Gly Gly Thr Phe Ser Lys Tyr
 20 25 30

Ala Ile Asn Trp Val Arg Gln Ala Pro Gly Gln Gly Leu Glu Trp Met
 35 40 45

Gly Gly Ile Ile Pro Ile Leu Gly Ile Ala Asn Tyr Ala Gln Lys Phe
 50 55 60

Gln Gly Arg Val Thr Ile Thr Thr Asp Glu Ser Thr Ser Thr Ala Tyr
65 70 75 80

Met Glu Leu Ser Ser Leu Arg Ser Glu Asp Thr Ala Val Tyr Tyr Cys
 85 90 95

Ala Arg Gly Trp Gly Arg Glu Gln Leu Ala Pro His Pro Ser Gln Tyr
 100 105 110

Tyr Tyr Tyr Tyr Tyr Gly Met Asp Val Trp Gly Gln Gly Thr Thr Val
 115 120 125

Thr Val Ser Ser
 130

<210> SEQ ID NO 274
<211> LENGTH: 25
<212> TYPE: PRT
<213> ORGANISM: Homo sapiens

<400> SEQUENCE: 274

Glu Val Gln Val Ile Gln Ser Gly Ala Asp Val Lys Lys Pro Gly Ser
 1 5 10 15

Ser Val Lys Val Ser Cys Lys Ser Ser
 20 25

<210> SEQ ID NO 275
<211> LENGTH: 8
<212> TYPE: PRT
<213> ORGANISM: Homo sapiens

<400> SEQUENCE: 275

Gly Gly Thr Phe Ser Lys Tyr Ala
 1 5

<210> SEQ ID NO 276
<211> LENGTH: 18
<212> TYPE: PRT
<213> ORGANISM: Homo sapiens

<400> SEQUENCE: 276

Ile Asn Trp Val Arg Gln Ala Pro Gly Gln Gly Leu Glu Trp Met Gly
 1 5 10 15

Gly Ile

-continued

<210> SEQ ID NO 277
<211> LENGTH: 7
<212> TYPE: PRT
<213> ORGANISM: Homo sapiens

<400> SEQUENCE: 277

```
Ile Pro Ile Leu Gly Ile Ala
 1               5
```

<210> SEQ ID NO 278
<211> LENGTH: 38
<212> TYPE: PRT
<213> ORGANISM: Homo sapiens

<400> SEQUENCE: 278

```
Asn Tyr Ala Gln Lys Phe Gln Gly Arg Val Thr Ile Thr Thr Asp Glu
 1               5                  10                  15

Ser Thr Ser Thr Ala Tyr Met Glu Leu Ser Ser Leu Arg Ser Glu Asp
            20                  25                  30

Thr Ala Val Tyr Tyr Cys
        35
```

<210> SEQ ID NO 279
<211> LENGTH: 25
<212> TYPE: PRT
<213> ORGANISM: Homo sapiens

<400> SEQUENCE: 279

```
Ala Arg Gly Trp Gly Arg Glu Gln Leu Ala Pro His Pro Ser Gln Tyr
 1               5                  10                  15

Tyr Tyr Tyr Tyr Tyr Gly Met Asp Val
            20                  25
```

<210> SEQ ID NO 280
<211> LENGTH: 11
<212> TYPE: PRT
<213> ORGANISM: Homo sapiens

<400> SEQUENCE: 280

```
Trp Gly Gln Gly Thr Thr Val Thr Val Ser Ser
 1               5                  10
```

<210> SEQ ID NO 281
<211> LENGTH: 110
<212> TYPE: PRT
<213> ORGANISM: Homo sapiens

<400> SEQUENCE: 281

```
Glu Ile Val Met Thr Gln Ser Pro Gly Thr Leu Ser Leu Ser Pro Gly
 1               5                  10                  15

Glu Arg Ala Thr Leu Ser Cys Arg Ala Ser Gln Ser Val Ala Ser Arg
            20                  25                  30

Tyr Leu Ala Trp Tyr Gln His Lys Pro Gly Leu Ala Pro Arg Leu Leu
        35                  40                  45

Ile Tyr Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Arg Thr Pro
                85                  90                  95

Ser Val Thr Phe Gly Gly Gly Thr Lys Val Glu Ile Lys Arg
            100                 105                 110
```

<210> SEQ ID NO 282
<211> LENGTH: 26
<212> TYPE: PRT
<213> ORGANISM: Homo sapiens

<400> SEQUENCE: 282

```
Glu Ile Val Met Thr Gln Ser Pro Gly Thr Leu Ser Leu Ser Pro Gly
 1               5                  10                  15

Glu Arg Ala Thr Leu Ser Cys Arg Ala Ser
            20                  25
```

<210> SEQ ID NO 283
<211> LENGTH: 7
<212> TYPE: PRT
<213> ORGANISM: Homo sapiens

<400> SEQUENCE: 283

```
Gln Ser Val Ala Ser Arg Tyr
 1               5
```

<210> SEQ ID NO 284
<211> LENGTH: 17
<212> TYPE: PRT
<213> ORGANISM: Homo sapiens

<400> SEQUENCE: 284

```
Leu Ala Trp Tyr Gln His Lys Pro Gly Leu Ala Pro Arg Leu Leu Ile
 1               5                  10                  15

Tyr
```

<210> SEQ ID NO 285
<211> LENGTH: 3
<212> TYPE: PRT
<213> ORGANISM: Homo sapiens

<400> SEQUENCE: 285

```
Gly Ala Ser
 1
```

<210> SEQ ID NO 286
<211> LENGTH: 36
<212> TYPE: PRT
<213> ORGANISM: Homo sapiens

<400> SEQUENCE: 286

```
Thr Arg Ala Thr Gly Ile Pro Asp Arg Phe Ser Gly Ser Gly Ser Gly
 1               5                  10                  15

Thr Asp Phe Thr Leu Thr Ile Ser Arg Leu Glu Pro Glu Asp Phe Ala
            20                  25                  30

Val Tyr Tyr Cys
        35
```

<210> SEQ ID NO 287
<211> LENGTH: 10
<212> TYPE: PRT
<213> ORGANISM: Homo sapiens

<400> SEQUENCE: 287

```
Gln Gln Tyr Gly Arg Thr Pro Ser Val Thr
 1               5                  10
```

<210> SEQ ID NO 288

<211> LENGTH: 11
<212> TYPE: PRT
<213> ORGANISM: Homo sapiens

<400> SEQUENCE: 288

Phe Gly Gly Gly Thr Lys Val Glu Ile Lys Arg
1 5 10

<210> SEQ ID NO 289
<211> LENGTH: 132
<212> TYPE: PRT
<213> ORGANISM: Homo sapiens

<400> SEQUENCE: 289

Glu Val Gln Val Ile Gln Ser Gly Ala Asp Val Lys Lys Pro Gly Ser
1 5 10 15

Ser Val Lys Val Ser Cys Lys Ser Ser Gly Gly Thr Phe Ser Lys Tyr
20 25 30

Ala Ile Asn Trp Val Arg Gln Ala Pro Gly Gln Gly Leu Glu Trp Met
35 40 45

Gly Gly Ile Ile Pro Ile Leu Gly Ile Ala Asn Tyr Ala Gln Lys Phe
50 55 60

Gln Gly Arg Val Thr Ile Thr Thr Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Gly Trp Gly Arg Glu Gln Leu Ala Pro His Pro Ser Gln Tyr
100 105 110

Tyr Tyr Tyr Tyr Tyr Gly Met Asp Val Trp Gly Gln Gly Thr Thr Val
115 120 125

Thr Val Ser Ser
130

<210> SEQ ID NO 290
<211> LENGTH: 25
<212> TYPE: PRT
<213> ORGANISM: Homo sapiens

<400> SEQUENCE: 290

Glu Val Gln Val Ile Gln Ser Gly Ala Asp Val Lys Lys Pro Gly Ser
1 5 10 15

Ser Val Lys Val Ser Cys Lys Ser Ser
20 25

<210> SEQ ID NO 291
<211> LENGTH: 8
<212> TYPE: PRT
<213> ORGANISM: Homo sapiens

<400> SEQUENCE: 291

Gly Gly Thr Phe Ser Lys Tyr Ala
1 5

<210> SEQ ID NO 292
<211> LENGTH: 18
<212> TYPE: PRT
<213> ORGANISM: Homo sapiens

<400> SEQUENCE: 292

Ile Asn Trp Val Arg Gln Ala Pro Gly Gln Gly Leu Glu Trp Met Gly
1 5 10 15

-continued

Gly Ile

<210> SEQ ID NO 293
<211> LENGTH: 7
<212> TYPE: PRT
<213> ORGANISM: Homo sapiens

<400> SEQUENCE: 293

Ile Pro Ile Leu Gly Ile Ala
1 5

<210> SEQ ID NO 294
<211> LENGTH: 38
<212> TYPE: PRT
<213> ORGANISM: Homo sapiens

<400> SEQUENCE: 294

Asn Tyr Ala Gln Lys Phe Gln Gly Arg Val Thr Ile Thr Thr Asp Glu
1 5 10 15

Ser Thr Ser Thr Ala Tyr Met Glu Leu Ser Ser Leu Arg Ser Glu Asp
20 25 30

Thr Ala Val Tyr Tyr Cys
35

<210> SEQ ID NO 295
<211> LENGTH: 25
<212> TYPE: PRT
<213> ORGANISM: Homo sapiens

<400> SEQUENCE: 295

Ala Arg Gly Trp Gly Arg Glu Gln Leu Ala Pro His Pro Ser Gln Tyr
1 5 10 15

Tyr Tyr Tyr Tyr Tyr Gly Met Asp Val
20 25

<210> SEQ ID NO 296
<211> LENGTH: 11
<212> TYPE: PRT
<213> ORGANISM: Homo sapiens

<400> SEQUENCE: 296

Trp Gly Gln Gly Thr Thr Val Thr Val Ser Ser
1 5 10

<210> SEQ ID NO 297
<211> LENGTH: 108
<212> TYPE: PRT
<213> ORGANISM: Homo sapiens

<400> SEQUENCE: 297

Glu Ile Val Met Thr Gln Ser Pro Gly Thr Pro Ser Leu Ser Pro Gly
1 5 10 15

Glu Arg Ala Thr Leu Ser Cys Arg Ala Ser Gln Ser Ile Arg Ser Thr
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Arg Ser Pro
85 90 95

Ser Phe Gly Gln Gly Thr Lys Val Glu Ile Lys Arg
100 105

<210> SEQ ID NO 298
<211> LENGTH: 26
<212> TYPE: PRT
<213> ORGANISM: Homo sapiens

<400> SEQUENCE: 298

Glu Ile Val Met Thr Gln Ser Pro Gly Thr Pro Ser Leu Ser Pro Gly
1 5 10 15

Glu Arg Ala Thr Leu Ser Cys Arg Ala Ser
20 25

<210> SEQ ID NO 299
<211> LENGTH: 7
<212> TYPE: PRT
<213> ORGANISM: Homo sapiens

<400> SEQUENCE: 299

Gln Ser Ile Arg Ser Thr Tyr
1 5

<210> SEQ ID NO 300
<211> LENGTH: 17
<212> TYPE: PRT
<213> ORGANISM: Homo sapiens

<400> SEQUENCE: 300

Leu Ala Trp Tyr Gln Gln Lys Pro Gly Gln Ala Pro Arg Leu Leu Ile
1 5 10 15

Tyr

<210> SEQ ID NO 301
<211> LENGTH: 3
<212> TYPE: PRT
<213> ORGANISM: Homo sapiens

<400> SEQUENCE: 301

Gly Ala Ser
1

<210> SEQ ID NO 302
<211> LENGTH: 36
<212> TYPE: PRT
<213> ORGANISM: Homo sapiens

<400> SEQUENCE: 302

Ser Arg Ala Thr Gly Ile Pro Asp Arg Phe Ser Gly Ser Gly Ser Gly
1 5 10 15

Thr Asp Phe Thr Leu Thr Ile Ser Arg Leu Glu Pro Glu Asp Phe Ala
20 25 30

Val Tyr Tyr Cys
35

<210> SEQ ID NO 303
<211> LENGTH: 8
<212> TYPE: PRT
<213> ORGANISM: Homo sapiens

<400> SEQUENCE: 303

Gln Gln Tyr Gly Arg Ser Pro Ser
1 5

<210> SEQ ID NO 304
<211> LENGTH: 11
<212> TYPE: PRT
<213> ORGANISM: Homo sapiens

<400> SEQUENCE: 304

Phe Gly Gln Gly Thr Lys Val Glu Ile Lys Arg
1               5                   10

<210> SEQ ID NO 305
<211> LENGTH: 132
<212> TYPE: PRT
<213> ORGANISM: Homo sapiens

<400> SEQUENCE: 305

Glu Val Gln Val Ile Gln Ser Gly Ala Asp Val Lys Lys Pro Gly Ser
1               5                   10                  15

Ser Val Lys Val Ser Cys Lys Ser Ser Gly Gly Thr Phe Ser Lys Tyr
            20                  25                  30

Ala Ile Asn Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
    50                  55                  60

Gln Gly Arg Val Thr Ile Thr Thr Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Trp Gly Arg Glu Gln Leu Ala Pro His Pro Ser Gln Tyr
            100                 105                 110

Tyr Tyr Tyr Tyr Tyr Gly Met Asp Val Trp Gly Gln Gly Thr Thr Val
        115                 120                 125

Thr Val Ser Ser
    130

<210> SEQ ID NO 306
<211> LENGTH: 25
<212> TYPE: PRT
<213> ORGANISM: Homo sapiens

<400> SEQUENCE: 306

Glu Val Gln Val Ile Gln Ser Gly Ala Asp Val Lys Lys Pro Gly Ser
1               5                   10                  15

Ser Val Lys Val Ser Cys Lys Ser Ser
            20                  25

<210> SEQ ID NO 307
<211> LENGTH: 8
<212> TYPE: PRT
<213> ORGANISM: Homo sapiens

<400> SEQUENCE: 307

Gly Gly Thr Phe Ser Lys Tyr Ala
1               5

<210> SEQ ID NO 308
<211> LENGTH: 18
<212> TYPE: PRT
<213> ORGANISM: Homo sapiens

<400> SEQUENCE: 308

-continued

```
Ile Asn Trp Val Arg Gln Ala Pro Gly Gln Gly Leu Glu Trp Met Gly
 1              5                   10                  15

Gly Ile


<210> SEQ ID NO 309
<211> LENGTH: 7
<212> TYPE: PRT
<213> ORGANISM: Homo sapiens

<400> SEQUENCE: 309

Ile Pro Ile Leu Gly Ile Ala
 1              5


<210> SEQ ID NO 310
<211> LENGTH: 38
<212> TYPE: PRT
<213> ORGANISM: Homo sapiens

<400> SEQUENCE: 310

Asn Tyr Ala Gln Lys Phe Gln Gly Arg Val Thr Ile Thr Thr Asp Glu
 1              5                   10                  15

Ser Thr Ser Thr Ala Tyr Met Glu Leu Ser Ser Leu Arg Ser Glu Asp
            20                  25                  30

Thr Ala Val Tyr Tyr Cys
        35


<210> SEQ ID NO 311
<211> LENGTH: 25
<212> TYPE: PRT
<213> ORGANISM: Homo sapiens

<400> SEQUENCE: 311

Ala Arg Gly Trp Gly Arg Glu Gln Leu Ala Pro His Pro Ser Gln Tyr
 1              5                   10                  15

Tyr Tyr Tyr Tyr Tyr Gly Met Asp Val
            20                  25


<210> SEQ ID NO 312
<211> LENGTH: 11
<212> TYPE: PRT
<213> ORGANISM: Homo sapiens

<400> SEQUENCE: 312

Trp Gly Gln Gly Thr Thr Val Thr Val Ser Ser
 1              5                   10


<210> SEQ ID NO 313
<211> LENGTH: 110
<212> TYPE: PRT
<213> ORGANISM: Homo sapiens

<400> SEQUENCE: 313

Glu Ile Val Met Thr Gln Ser Pro Gly Thr Leu Ser Leu Ala Pro Gly
 1              5                   10                  15

Glu Arg Ala Thr Leu Ser Cys Trp Ala Ser Gln Ser Val Arg Asn Asn
            20                  25                  30

Tyr Leu Ala Trp Tyr Gln Gln Lys Pro Gly Gln Ala Pro Arg Leu Val
        35                  40                  45

Ile Tyr Asn Gly Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Asp
65                  70                  75                  80
```

```
Pro Glu Asp Phe Ala Val Tyr Tyr Cys Gln Gln Tyr Gly Asn Ser Arg
                85                  90                  95

Arg Val Thr Phe Gly Gly Gly Thr Lys Val Glu Ile Lys Arg
            100                 105                 110


<210> SEQ ID NO 314
<211> LENGTH: 26
<212> TYPE: PRT
<213> ORGANISM: Homo sapiens

<400> SEQUENCE: 314

Glu Ile Val Met Thr Gln Ser Pro Gly Thr Leu Ser Leu Ala Pro Gly
 1               5                  10                  15

Glu Arg Ala Thr Leu Ser Cys Trp Ala Ser
            20                  25


<210> SEQ ID NO 315
<211> LENGTH: 7
<212> TYPE: PRT
<213> ORGANISM: Homo sapiens

<400> SEQUENCE: 315

Gln Ser Val Arg Asn Asn Tyr
 1               5


<210> SEQ ID NO 316
<211> LENGTH: 17
<212> TYPE: PRT
<213> ORGANISM: Homo sapiens

<400> SEQUENCE: 316

Leu Ala Trp Tyr Gln Gln Lys Pro Gly Gln Ala Pro Arg Leu Val Ile
 1               5                  10                  15

Tyr


<210> SEQ ID NO 317
<211> LENGTH: 3
<212> TYPE: PRT
<213> ORGANISM: Homo sapiens

<400> SEQUENCE: 317

Asn Gly Ser
 1


<210> SEQ ID NO 318
<211> LENGTH: 36
<212> TYPE: PRT
<213> ORGANISM: Homo sapiens

<400> SEQUENCE: 318

Thr Arg Ala Thr Gly Ile Pro Asp Arg Phe Ser Gly Ser Gly Ser Gly
 1               5                  10                  15

Thr Asp Phe Thr Leu Thr Ile Ser Arg Leu Asp Pro Glu Asp Phe Ala
            20                  25                  30

Val Tyr Tyr Cys
        35


<210> SEQ ID NO 319
<211> LENGTH: 10
<212> TYPE: PRT
<213> ORGANISM: Homo sapiens

<400> SEQUENCE: 319
```

Gln Gln Tyr Gly Asn Ser Arg Arg Val Thr
1 5 10

<210> SEQ ID NO 320
<211> LENGTH: 11
<212> TYPE: PRT
<213> ORGANISM: Homo sapiens

<400> SEQUENCE: 320

Phe Gly Gly Gly Thr Lys Val Glu Ile Lys Arg
1 5 10

<210> SEQ ID NO 321
<211> LENGTH: 132
<212> TYPE: PRT
<213> ORGANISM: Homo sapiens

<400> SEQUENCE: 321

Glu Val Gln Val Ile Gln Ser Gly Ala Asp Val Lys Lys Pro Gly Ser
1 5 10 15

Ser Val Lys Val Ser Cys Lys Ser Ser Gly Gly Thr Phe Ser Lys Tyr
20 25 30

Ala Ile Asn Trp Val Arg Gln Ala Pro Gly Gln Gly Leu Glu Trp Met
35 40 45

Gly Gly Ile Ile Pro Ile Leu Gly Ile Ala Asn Tyr Ala Gln Lys Phe
50 55 60

Gln Gly Arg Val Thr Ile Thr Thr Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Gly Trp Gly Arg Glu Gln Leu Ala Pro His Pro Ser Gln Tyr
100 105 110

Tyr Tyr Tyr Tyr Tyr Gly Met Asp Val Trp Gly Gln Gly Thr Thr Val
115 120 125

Thr Val Ser Ser
130

<210> SEQ ID NO 322
<211> LENGTH: 25
<212> TYPE: PRT
<213> ORGANISM: Homo sapiens

<400> SEQUENCE: 322

Glu Val Gln Val Ile Gln Ser Gly Ala Asp Val Lys Lys Pro Gly Ser
1 5 10 15

Ser Val Lys Val Ser Cys Lys Ser Ser
20 25

<210> SEQ ID NO 323
<211> LENGTH: 8
<212> TYPE: PRT
<213> ORGANISM: Homo sapiens

<400> SEQUENCE: 323

Gly Gly Thr Phe Ser Lys Tyr Ala
1 5

<210> SEQ ID NO 324
<211> LENGTH: 18
<212> TYPE: PRT
<213> ORGANISM: Homo sapiens

<400> SEQUENCE: 324

```
Ile Asn Trp Val Arg Gln Ala Pro Gly Gln Gly Leu Glu Trp Met Gly
 1               5                  10                  15

Gly Ile
```

<210> SEQ ID NO 325
<211> LENGTH: 7
<212> TYPE: PRT
<213> ORGANISM: Homo sapiens

<400> SEQUENCE: 325

```
Ile Pro Ile Leu Gly Ile Ala
 1               5
```

<210> SEQ ID NO 326
<211> LENGTH: 38
<212> TYPE: PRT
<213> ORGANISM: Homo sapiens

<400> SEQUENCE: 326

```
Asn Tyr Ala Gln Lys Phe Gln Gly Arg Val Thr Ile Thr Thr Asp Glu
 1               5                  10                  15

Ser Thr Ser Thr Ala Tyr Met Glu Leu Ser Ser Leu Arg Ser Glu Asp
            20                  25                  30

Thr Ala Val Tyr Tyr Cys
        35
```

<210> SEQ ID NO 327
<211> LENGTH: 25
<212> TYPE: PRT
<213> ORGANISM: Homo sapiens

<400> SEQUENCE: 327

```
Ala Arg Gly Trp Gly Arg Glu Gln Leu Ala Pro His Pro Ser Gln Tyr
 1               5                  10                  15

Tyr Tyr Tyr Tyr Tyr Gly Met Asp Val
            20                  25
```

<210> SEQ ID NO 328
<211> LENGTH: 11
<212> TYPE: PRT
<213> ORGANISM: Homo sapiens

<400> SEQUENCE: 328

```
Trp Gly Gln Gly Thr Thr Val Thr Val Ser Ser
 1               5                  10
```

<210> SEQ ID NO 329
<211> LENGTH: 108
<212> TYPE: PRT
<213> ORGANISM: Homo sapiens

<400> SEQUENCE: 329

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Thr Ser Thr Arg Ala Thr Gly Ile Pro Asp Arg Phe Ser
    50                  55                  60
```

```
Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Arg Tyr Gly Ser Ser Pro
                85                  90                  95

Ala Phe Gly Gln Gly Thr Lys Val Glu Ile Lys Arg
            100                 105


<210> SEQ ID NO 330
<211> LENGTH: 26
<212> TYPE: PRT
<213> ORGANISM: Homo sapiens

<400> SEQUENCE: 330

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser
            20                  25


<210> SEQ ID NO 331
<211> LENGTH: 7
<212> TYPE: PRT
<213> ORGANISM: Homo sapiens

<400> SEQUENCE: 331

Gln Ser Val Ser Ser Ser Tyr
 1               5


<210> SEQ ID NO 332
<211> LENGTH: 17
<212> TYPE: PRT
<213> ORGANISM: Homo sapiens

<400> SEQUENCE: 332

Leu Ala Trp Tyr Gln Gln Lys Pro Gly Gln Ala Pro Arg Leu Leu Ile
 1               5                  10                  15

Tyr


<210> SEQ ID NO 333
<211> LENGTH: 3
<212> TYPE: PRT
<213> ORGANISM: Homo sapiens

<400> SEQUENCE: 333

Gly Thr Ser
 1


<210> SEQ ID NO 334
<211> LENGTH: 36
<212> TYPE: PRT
<213> ORGANISM: Homo sapiens

<400> SEQUENCE: 334

Thr Arg Ala Thr Gly Ile Pro Asp Arg Phe Ser Gly Ser Gly Ser Gly
 1               5                  10                  15

Thr Asp Phe Thr Leu Thr Ile Ser Arg Leu Glu Pro Glu Asp Phe Ala
            20                  25                  30

Val Tyr Tyr Cys
        35


<210> SEQ ID NO 335
<211> LENGTH: 8
<212> TYPE: PRT
```

<213> ORGANISM: Homo sapiens

<400> SEQUENCE: 335

Gln Arg Tyr Gly Ser Ser Pro Ala
1 5

<210> SEQ ID NO 336
<211> LENGTH: 11
<212> TYPE: PRT
<213> ORGANISM: Homo sapiens

<400> SEQUENCE: 336

Phe Gly Gln Gly Thr Lys Val Glu Ile Lys Arg
1 5 10

<210> SEQ ID NO 337
<211> LENGTH: 132
<212> TYPE: PRT
<213> ORGANISM: Homo sapiens

<400> SEQUENCE: 337

Glu Val Gln Val Ile Gln Ser Gly Ala Asp Val Lys Lys Pro Gly Ser
1 5 10 15

Ser Val Lys Val Ser Cys Lys Ser Ser Gly Gly Thr Phe Ser Lys Tyr
20 25 30

Ala Ile Asn Trp Val Arg Gln Ala Pro Gly Gln Gly Leu Glu Trp Met
35 40 45

Gly Gly Ile Ile Pro Ile Leu Gly Ile Ala Asn Tyr Ala Gln Lys Phe
50 55 60

Gln Gly Arg Val Thr Ile Thr Thr Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Gly Trp Gly Arg Glu Gln Leu Ala Pro His Pro Ser Gln Tyr
100 105 110

Tyr Tyr Tyr Tyr Tyr Gly Met Asp Val Trp Gly Gln Gly Thr Thr Val
115 120 125

Thr Val Ser Ser
130

<210> SEQ ID NO 338
<211> LENGTH: 25
<212> TYPE: PRT
<213> ORGANISM: Homo sapiens

<400> SEQUENCE: 338

Glu Val Gln Val Ile Gln Ser Gly Ala Asp Val Lys Lys Pro Gly Ser
1 5 10 15

Ser Val Lys Val Ser Cys Lys Ser Ser
20 25

<210> SEQ ID NO 339
<211> LENGTH: 8
<212> TYPE: PRT
<213> ORGANISM: Homo sapiens

<400> SEQUENCE: 339

Gly Gly Thr Phe Ser Lys Tyr Ala
1 5

<210> SEQ ID NO 340

<211> LENGTH: 18
<212> TYPE: PRT
<213> ORGANISM: Homo sapiens

<400> SEQUENCE: 340

Ile Asn Trp Val Arg Gln Ala Pro Gly Gln Gly Leu Glu Trp Met Gly
1 5 10 15

Gly Ile

<210> SEQ ID NO 341
<211> LENGTH: 7
<212> TYPE: PRT
<213> ORGANISM: Homo sapiens

<400> SEQUENCE: 341

Ile Pro Ile Leu Gly Ile Ala
1 5

<210> SEQ ID NO 342
<211> LENGTH: 38
<212> TYPE: PRT
<213> ORGANISM: Homo sapiens

<400> SEQUENCE: 342

Asn Tyr Ala Gln Lys Phe Gln Gly Arg Val Thr Ile Thr Thr Asp Glu
1 5 10 15

Ser Thr Ser Thr Ala Tyr Met Glu Leu Ser Ser Leu Arg Ser Glu Asp
20 25 30

Thr Ala Val Tyr Tyr Cys
35

<210> SEQ ID NO 343
<211> LENGTH: 25
<212> TYPE: PRT
<213> ORGANISM: Homo sapiens

<400> SEQUENCE: 343

Ala Arg Gly Trp Gly Arg Glu Gln Leu Ala Pro His Pro Ser Gln Tyr
1 5 10 15

Tyr Tyr Tyr Tyr Tyr Gly Met Asp Val
20 25

<210> SEQ ID NO 344
<211> LENGTH: 11
<212> TYPE: PRT
<213> ORGANISM: Homo sapiens

<400> SEQUENCE: 344

Trp Gly Gln Gly Thr Thr Val Thr Val Ser Ser
1 5 10

<210> SEQ ID NO 345
<211> LENGTH: 107
<212> TYPE: PRT
<213> ORGANISM: Homo sapiens

<400> SEQUENCE: 345

Asp Ile Gln Met Thr Gln Ser Pro Ala Thr Leu Ser Ala Ser Ile Gly
1 5 10 15

Asp Arg Val Thr Ile Thr Cys Arg Ala Ser Gln Ser Ile Ser Lys Trp
20 25 30

Leu Ala Trp Tyr Gln Gln Lys Pro Gly Lys Ala Pro Lys Leu Leu Ile
35 40 45

```
Tyr Lys Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Tyr Ile Asn Tyr Ala Thr
                85                  90                  95

Phe Gly Gln Gly Thr Lys Val Glu Ile Lys Arg
            100                 105


<210> SEQ ID NO 346
<211> LENGTH: 26
<212> TYPE: PRT
<213> ORGANISM: Homo sapiens

<400> SEQUENCE: 346

Asp Ile Gln Met Thr Gln Ser Pro Ala Thr Leu Ser Ala Ser Ile Gly
 1               5                  10                  15

Asp Arg Val Thr Ile Thr Cys Arg Ala Ser
            20                  25


<210> SEQ ID NO 347
<211> LENGTH: 6
<212> TYPE: PRT
<213> ORGANISM: Homo sapiens

<400> SEQUENCE: 347

Gln Ser Ile Ser Lys Trp
 1               5


<210> SEQ ID NO 348
<211> LENGTH: 17
<212> TYPE: PRT
<213> ORGANISM: Homo sapiens

<400> SEQUENCE: 348

Leu Ala Trp Tyr Gln Gln Lys Pro Gly Lys Ala Pro Lys Leu Leu Ile
 1               5                  10                  15

Tyr


<210> SEQ ID NO 349
<211> LENGTH: 3
<212> TYPE: PRT
<213> ORGANISM: Homo sapiens

<400> SEQUENCE: 349

Lys Ala Ser
 1


<210> SEQ ID NO 350
<211> LENGTH: 36
<212> TYPE: PRT
<213> ORGANISM: Homo sapiens

<400> SEQUENCE: 350

Thr Leu Glu Ser Gly Val Pro Ser Arg Phe Ser Gly Ser Gly Ser Gly
 1               5                  10                  15

Thr Asp Phe Thr Leu Thr Ile Ser Ser Leu Gln Pro Asp Asp Phe Ala
            20                  25                  30

Thr Tyr Tyr Cys
        35
```

<210> SEQ ID NO 351
<211> LENGTH: 8
<212> TYPE: PRT
<213> ORGANISM: Homo sapiens

<400> SEQUENCE: 351

```
Gln Gln Tyr Ile Asn Tyr Ala Thr
 1               5
```

<210> SEQ ID NO 352
<211> LENGTH: 11
<212> TYPE: PRT
<213> ORGANISM: Homo sapiens

<400> SEQUENCE: 352

```
Phe Gly Gln Gly Thr Lys Val Glu Ile Lys Arg
 1               5                   10
```

<210> SEQ ID NO 353
<211> LENGTH: 132
<212> TYPE: PRT
<213> ORGANISM: Homo sapiens

<400> SEQUENCE: 353

```
Glu Val Gln Val Ile Gln Ser Gly Ala Asp Val Lys Lys Pro Gly Ser
 1               5                   10                  15

Ser Val Lys Val Ser Cys Lys Ser Ser Gly Gly Thr Phe Ser Lys Tyr
            20                  25                  30

Ala Ile Asn Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
    50                  55                  60

Gln Gly Arg Val Thr Ile Thr Thr Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Trp Gly Arg Glu Gln Leu Ala Pro His Pro Ser Gln Tyr
            100                 105                 110

Tyr Tyr Tyr Tyr Tyr Gly Met Asp Val Trp Gly Gln Gly Thr Thr Val
        115                 120                 125

Thr Val Ser Ser
    130
```

<210> SEQ ID NO 354
<211> LENGTH: 25
<212> TYPE: PRT
<213> ORGANISM: Homo sapiens

<400> SEQUENCE: 354

```
Glu Val Gln Val Ile Gln Ser Gly Ala Asp Val Lys Lys Pro Gly Ser
 1               5                   10                  15

Ser Val Lys Val Ser Cys Lys Ser Ser
            20                  25
```

<210> SEQ ID NO 355
<211> LENGTH: 8
<212> TYPE: PRT
<213> ORGANISM: Homo sapiens

<400> SEQUENCE: 355

```
Gly Gly Thr Phe Ser Lys Tyr Ala
 1               5
```

<210> SEQ ID NO 356
<211> LENGTH: 18
<212> TYPE: PRT
<213> ORGANISM: Homo sapiens

<400> SEQUENCE: 356

Ile Asn Trp Val Arg Gln Ala Pro Gly Gln Gly Leu Glu Trp Met Gly
1 5 10 15

Gly Ile

<210> SEQ ID NO 357
<211> LENGTH: 7
<212> TYPE: PRT
<213> ORGANISM: Homo sapiens

<400> SEQUENCE: 357

Ile Pro Ile Leu Gly Ile Ala
1 5

<210> SEQ ID NO 358
<211> LENGTH: 38
<212> TYPE: PRT
<213> ORGANISM: Homo sapiens

<400> SEQUENCE: 358

Asn Tyr Ala Gln Lys Phe Gln Gly Arg Val Thr Ile Thr Thr Asp Glu
1 5 10 15

Ser Thr Ser Thr Ala Tyr Met Glu Leu Ser Ser Leu Arg Ser Glu Asp
20 25 30

Thr Ala Val Tyr Tyr Cys
35

<210> SEQ ID NO 359
<211> LENGTH: 25
<212> TYPE: PRT
<213> ORGANISM: Homo sapiens

<400> SEQUENCE: 359

Ala Arg Gly Trp Gly Arg Glu Gln Leu Ala Pro His Pro Ser Gln Tyr
1 5 10 15

Tyr Tyr Tyr Tyr Tyr Gly Met Asp Val
20 25

<210> SEQ ID NO 360
<211> LENGTH: 11
<212> TYPE: PRT
<213> ORGANISM: Homo sapiens

<400> SEQUENCE: 360

Trp Gly Gln Gly Thr Thr Val Thr Val Ser Ser
1 5 10

<210> SEQ ID NO 361
<211> LENGTH: 110
<212> TYPE: PRT
<213> ORGANISM: Homo sapiens

<400> SEQUENCE: 361

Glu Ile Val Met Thr Gln Ser Pro Gly Thr Leu Ser Leu Ala Pro Gly
1 5 10 15

Glu Arg Ala Thr Leu Ser Cys Trp Ala Ser Gln Ser Val Arg Asn Asn
20 25 30

```
Tyr Leu Ala Trp Tyr Gln Gln Lys Pro Gly Gln Ala Pro Arg Leu Val
        35                  40                  45

Ile Tyr Asn Gly Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Asp
65                  70                  75                  80

Pro Glu Asp Phe Ala Val Tyr Tyr Cys Gln Gln Tyr Gly Asn Ser Arg
                85                  90                  95

Arg Val Thr Phe Gly Gly Gly Thr Lys Val Glu Ile Lys Arg
            100                 105                 110


<210> SEQ ID NO 362
<211> LENGTH: 26
<212> TYPE: PRT
<213> ORGANISM: Homo sapiens

<400> SEQUENCE: 362

Glu Ile Val Met Thr Gln Ser Pro Gly Thr Leu Ser Leu Ala Pro Gly
 1               5                  10                  15

Glu Arg Ala Thr Leu Ser Cys Trp Ala Ser
            20                  25


<210> SEQ ID NO 363
<211> LENGTH: 7
<212> TYPE: PRT
<213> ORGANISM: Homo sapiens

<400> SEQUENCE: 363

Gln Ser Val Arg Asn Asn Tyr
 1               5


<210> SEQ ID NO 364
<211> LENGTH: 17
<212> TYPE: PRT
<213> ORGANISM: Homo sapiens

<400> SEQUENCE: 364

Leu Ala Trp Tyr Gln Gln Lys Pro Gly Gln Ala Pro Arg Leu Val Ile
 1               5                  10                  15

Tyr


<210> SEQ ID NO 365
<211> LENGTH: 3
<212> TYPE: PRT
<213> ORGANISM: Homo sapiens

<400> SEQUENCE: 365

Asn Gly Ser
 1


<210> SEQ ID NO 366
<211> LENGTH: 36
<212> TYPE: PRT
<213> ORGANISM: Homo sapiens

<400> SEQUENCE: 366

Thr Arg Ala Thr Gly Ile Pro Asp Arg Phe Ser Gly Ser Gly Ser Gly
 1               5                  10                  15

Thr Asp Phe Thr Leu Thr Ile Ser Arg Leu Asp Pro Glu Asp Phe Ala
            20                  25                  30

Val Tyr Tyr Cys
```

35

<210> SEQ ID NO 367
<211> LENGTH: 10
<212> TYPE: PRT
<213> ORGANISM: Homo sapiens

<400> SEQUENCE: 367

Gln Gln Tyr Gly Asn Ser Arg Arg Val Thr
1 5 10

<210> SEQ ID NO 368
<211> LENGTH: 11
<212> TYPE: PRT
<213> ORGANISM: Homo sapiens

<400> SEQUENCE: 368

Phe Gly Gly Gly Thr Lys Val Glu Ile Lys Arg
1 5 10

<210> SEQ ID NO 369
<211> LENGTH: 132
<212> TYPE: PRT
<213> ORGANISM: Homo sapiens

<400> SEQUENCE: 369

Glu Val Gln Val Ile Gln Ser Gly Ala Asp Val Lys Lys Pro Gly Ser
1 5 10 15

Ser Val Lys Val Ser Cys Lys Ser Ser Gly Gly Thr Phe Ser Lys Tyr
20 25 30

Ala Ile Asn Trp Val Arg Gln Ala Pro Gly Gln Gly Leu Glu Trp Met
35 40 45

Gly Gly Ile Ile Pro Ile Leu Gly Ile Ala Asn Tyr Ala Gln Lys Phe
50 55 60

Gln Gly Arg Val Thr Ile Thr Thr Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Gly Trp Gly Arg Glu Gln Leu Ala Pro His Pro Ser Gln Tyr
100 105 110

Tyr Tyr Tyr Tyr Tyr Gly Met Asp Val Trp Gly Gln Gly Thr Thr Val
115 120 125

Thr Val Ser Ser
130

<210> SEQ ID NO 370
<211> LENGTH: 25
<212> TYPE: PRT
<213> ORGANISM: Homo sapiens

<400> SEQUENCE: 370

Glu Val Gln Val Ile Gln Ser Gly Ala Asp Val Lys Lys Pro Gly Ser
1 5 10 15

Ser Val Lys Val Ser Cys Lys Ser Ser
20 25

<210> SEQ ID NO 371
<211> LENGTH: 8
<212> TYPE: PRT
<213> ORGANISM: Homo sapiens

<400> SEQUENCE: 371

Gly Gly Thr Phe Ser Lys Tyr Ala
1 5

<210> SEQ ID NO 372
<211> LENGTH: 18
<212> TYPE: PRT
<213> ORGANISM: Homo sapiens

<400> SEQUENCE: 372

Ile Asn Trp Val Arg Gln Ala Pro Gly Gln Gly Leu Glu Trp Met Gly
1 5 10 15

Gly Ile

<210> SEQ ID NO 373
<211> LENGTH: 7
<212> TYPE: PRT
<213> ORGANISM: Homo sapiens

<400> SEQUENCE: 373

Ile Pro Ile Leu Gly Ile Ala
1 5

<210> SEQ ID NO 374
<211> LENGTH: 38
<212> TYPE: PRT
<213> ORGANISM: Homo sapiens

<400> SEQUENCE: 374

Asn Tyr Ala Gln Lys Phe Gln Gly Arg Val Thr Ile Thr Thr Asp Glu
1 5 10 15

Ser Thr Ser Thr Ala Tyr Met Glu Leu Ser Ser Leu Arg Ser Glu Asp
20 25 30

Thr Ala Val Tyr Tyr Cys
35

<210> SEQ ID NO 375
<211> LENGTH: 25
<212> TYPE: PRT
<213> ORGANISM: Homo sapiens

<400> SEQUENCE: 375

Ala Arg Gly Trp Gly Arg Glu Gln Leu Ala Pro His Pro Ser Gln Tyr
1 5 10 15

Tyr Tyr Tyr Tyr Tyr Gly Met Asp Val
20 25

<210> SEQ ID NO 376
<211> LENGTH: 11
<212> TYPE: PRT
<213> ORGANISM: Homo sapiens

<400> SEQUENCE: 376

Trp Gly Gln Gly Thr Thr Val Thr Val Ser Ser
1 5 10

<210> SEQ ID NO 377
<211> LENGTH: 107
<212> TYPE: PRT
<213> ORGANISM: Homo sapiens

<400> SEQUENCE: 377

Glu Ile Val Leu Thr Gln Ser Pro Ala Thr Leu Ser Leu Ser Pro Gly
1 5 10 15

```
Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys Arg
            100                 105


<210> SEQ ID NO 378
<211> LENGTH: 26
<212> TYPE: PRT
<213> ORGANISM: Homo sapiens

<400> SEQUENCE: 378

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser
            20                  25


<210> SEQ ID NO 379
<211> LENGTH: 6
<212> TYPE: PRT
<213> ORGANISM: Homo sapiens

<400> SEQUENCE: 379

Gln Ser Val Ser Ser Tyr
 1               5


<210> SEQ ID NO 380
<211> LENGTH: 17
<212> TYPE: PRT
<213> ORGANISM: Homo sapiens

<400> SEQUENCE: 380

Leu Ala Trp Tyr Gln Gln Lys Pro Gly Gln Ala Pro Arg Leu Leu Ile
 1               5                  10                  15

Tyr


<210> SEQ ID NO 381
<211> LENGTH: 3
<212> TYPE: PRT
<213> ORGANISM: Homo sapiens

<400> SEQUENCE: 381

Asp Ala Ser
 1


<210> SEQ ID NO 382
<211> LENGTH: 36
<212> TYPE: PRT
<213> ORGANISM: Homo sapiens

<400> SEQUENCE: 382

Asn Arg Ala Thr Gly Ile Pro Ala Arg Phe Ser Gly Ser Gly Ser Gly
 1               5                  10                  15

Thr Asp Phe Thr Leu Thr Ile Ser Ser Leu Glu Pro Glu Asp Phe Ala
```

-continued

```
            20                  25                  30

Val Tyr Tyr Cys
        35


<210> SEQ ID NO 383
<211> LENGTH: 8
<212> TYPE: PRT
<213> ORGANISM: Homo sapiens

<400> SEQUENCE: 383

Gln Gln Arg Ser Asn Trp Pro Thr
 1               5


<210> SEQ ID NO 384
<211> LENGTH: 11
<212> TYPE: PRT
<213> ORGANISM: Homo sapiens

<400> SEQUENCE: 384

Phe Gly Gln Gly Thr Lys Val Glu Ile Lys Arg
 1               5                  10


<210> SEQ ID NO 385
<211> LENGTH: 132
<212> TYPE: PRT
<213> ORGANISM: Homo sapiens

<400> SEQUENCE: 385

Glu Val Gln Val Ile Gln Ser Gly Ala Asp Val Lys Lys Pro Gly Ser
 1               5                  10                  15

Ser Val Lys Val Ser Cys Lys Ser Ser Gly Gly Thr Phe Ser Lys Tyr
            20                  25                  30

Ala Ile Asn Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
    50                  55                  60

Gln Gly Arg Val Thr Ile Thr Thr Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Trp Gly Arg Glu Gln Leu Ala Pro His Pro Ser Gln Tyr
            100                 105                 110

Tyr Tyr Tyr Tyr Tyr Gly Met Asp Val Trp Gly Gln Gly Thr Thr Val
        115                 120                 125

Thr Val Ser Ser
    130


<210> SEQ ID NO 386
<211> LENGTH: 25
<212> TYPE: PRT
<213> ORGANISM: Homo sapiens

<400> SEQUENCE: 386

Glu Val Gln Val Ile Gln Ser Gly Ala Asp Val Lys Lys Pro Gly Ser
 1               5                  10                  15

Ser Val Lys Val Ser Cys Lys Ser Ser
            20                  25


<210> SEQ ID NO 387
<211> LENGTH: 8
<212> TYPE: PRT
```

<213> ORGANISM: Homo sapiens

<400> SEQUENCE: 387

Gly Gly Thr Phe Ser Lys Tyr Ala
1 5

<210> SEQ ID NO 388
<211> LENGTH: 18
<212> TYPE: PRT
<213> ORGANISM: Homo sapiens

<400> SEQUENCE: 388

Ile Asn Trp Val Arg Gln Ala Pro Gly Gln Gly Leu Glu Trp Met Gly
1 5 10 15

Gly Ile

<210> SEQ ID NO 389
<211> LENGTH: 7
<212> TYPE: PRT
<213> ORGANISM: Homo sapiens

<400> SEQUENCE: 389

Ile Pro Ile Leu Gly Ile Ala
1 5

<210> SEQ ID NO 390
<211> LENGTH: 38
<212> TYPE: PRT
<213> ORGANISM: Homo sapiens

<400> SEQUENCE: 390

Asn Tyr Ala Gln Lys Phe Gln Gly Arg Val Thr Ile Thr Thr Asp Glu
1 5 10 15

Ser Thr Ser Thr Ala Tyr Met Glu Leu Ser Ser Leu Arg Ser Glu Asp
20 25 30

Thr Ala Val Tyr Tyr Cys
35

<210> SEQ ID NO 391
<211> LENGTH: 25
<212> TYPE: PRT
<213> ORGANISM: Homo sapiens

<400> SEQUENCE: 391

Ala Arg Gly Trp Gly Arg Glu Gln Leu Ala Pro His Pro Ser Gln Tyr
1 5 10 15

Tyr Tyr Tyr Tyr Tyr Gly Met Asp Val
20 25

<210> SEQ ID NO 392
<211> LENGTH: 11
<212> TYPE: PRT
<213> ORGANISM: Homo sapiens

<400> SEQUENCE: 392

Trp Gly Gln Gly Thr Thr Val Thr Val Ser Ser
1 5 10

<210> SEQ ID NO 393
<211> LENGTH: 110
<212> TYPE: PRT
<213> ORGANISM: Homo sapiens

<400> SEQUENCE: 393

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Thr Ile Thr Phe Gly Gln Gly Thr Arg Leu Glu Ile Lys Arg
            100                 105                 110


<210> SEQ ID NO 394
<211> LENGTH: 26
<212> TYPE: PRT
<213> ORGANISM: Homo sapiens

<400> SEQUENCE: 394

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser
            20                  25


<210> SEQ ID NO 395
<211> LENGTH: 7
<212> TYPE: PRT
<213> ORGANISM: Homo sapiens

<400> SEQUENCE: 395

Gln Ser Val Ser Ser Ser Tyr
 1               5


<210> SEQ ID NO 396
<211> LENGTH: 17
<212> TYPE: PRT
<213> ORGANISM: Homo sapiens

<400> SEQUENCE: 396

Leu Ala Trp Tyr Gln Gln Lys Pro Gly Gln Ala Pro Arg Leu Leu Ile
 1               5                  10                  15

Tyr


<210> SEQ ID NO 397
<211> LENGTH: 3
<212> TYPE: PRT
<213> ORGANISM: Homo sapiens

<400> SEQUENCE: 397

Gly Ala Ser
 1


<210> SEQ ID NO 398
<211> LENGTH: 36
<212> TYPE: PRT
<213> ORGANISM: Homo sapiens

<400> SEQUENCE: 398

Ser Arg Ala Thr Gly Ile Pro Asp Arg Phe Ser Gly Ser Gly Ser Gly
```

-continued

```
 1               5                   10                  15

Thr Asp Phe Thr Leu Thr Ile Ser Arg Leu Glu Pro Glu Asp Phe Ala
            20                  25                  30

Val Tyr Tyr Cys
        35


<210> SEQ ID NO 399
<211> LENGTH: 10
<212> TYPE: PRT
<213> ORGANISM: Homo sapiens

<400> SEQUENCE: 399

Gln Gln Tyr Gly Ser Ser Pro Thr Ile Thr
 1               5                   10


<210> SEQ ID NO 400
<211> LENGTH: 11
<212> TYPE: PRT
<213> ORGANISM: Homo sapiens

<400> SEQUENCE: 400

Phe Gly Gln Gly Thr Arg Leu Glu Ile Lys Arg
 1               5                   10


<210> SEQ ID NO 401
<211> LENGTH: 132
<212> TYPE: PRT
<213> ORGANISM: Homo sapiens

<400> SEQUENCE: 401

Glu Val Gln Val Ile Gln Ser Gly Ala Asp Val Lys Lys Pro Gly Ser
 1               5                   10                  15

Ser Val Lys Val Ser Cys Lys Ser Ser Gly Gly Thr Phe Ser Lys Tyr
            20                  25                  30

Ala Ile Asn Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
    50                  55                  60

Gln Gly Arg Val Thr Ile Thr Thr Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Trp Gly Arg Glu Gln Leu Ala Pro His Pro Ser Gln Tyr
            100                 105                 110

Tyr Tyr Tyr Tyr Tyr Gly Met Asp Val Trp Gly Gln Gly Thr Thr Val
        115                 120                 125

Thr Val Ser Ser
    130


<210> SEQ ID NO 402
<211> LENGTH: 25
<212> TYPE: PRT
<213> ORGANISM: Homo sapiens

<400> SEQUENCE: 402

Glu Val Gln Val Ile Gln Ser Gly Ala Asp Val Lys Lys Pro Gly Ser
 1               5                   10                  15

Ser Val Lys Val Ser Cys Lys Ser Ser
            20                  25
```

<210> SEQ ID NO 403
<211> LENGTH: 8
<212> TYPE: PRT
<213> ORGANISM: Homo sapiens

<400> SEQUENCE: 403

Gly Gly Thr Phe Ser Lys Tyr Ala
1 5

<210> SEQ ID NO 404
<211> LENGTH: 18
<212> TYPE: PRT
<213> ORGANISM: Homo sapiens

<400> SEQUENCE: 404

Ile Asn Trp Val Arg Gln Ala Pro Gly Gln Gly Leu Glu Trp Met Gly
1 5 10 15

Gly Ile

<210> SEQ ID NO 405
<211> LENGTH: 7
<212> TYPE: PRT
<213> ORGANISM: Homo sapiens

<400> SEQUENCE: 405

Ile Pro Ile Leu Gly Ile Ala
1 5

<210> SEQ ID NO 406
<211> LENGTH: 38
<212> TYPE: PRT
<213> ORGANISM: Homo sapiens

<400> SEQUENCE: 406

Asn Tyr Ala Gln Lys Phe Gln Gly Arg Val Thr Ile Thr Thr Asp Glu
1 5 10 15

Ser Thr Ser Thr Ala Tyr Met Glu Leu Ser Ser Leu Arg Ser Glu Asp
20 25 30

Thr Ala Val Tyr Tyr Cys
35

<210> SEQ ID NO 407
<211> LENGTH: 25
<212> TYPE: PRT
<213> ORGANISM: Homo sapiens

<400> SEQUENCE: 407

Ala Arg Gly Trp Gly Arg Glu Gln Leu Ala Pro His Pro Ser Gln Tyr
1 5 10 15

Tyr Tyr Tyr Tyr Tyr Gly Met Asp Val
20 25

<210> SEQ ID NO 408
<211> LENGTH: 11
<212> TYPE: PRT
<213> ORGANISM: Homo sapiens

<400> SEQUENCE: 408

Trp Gly Gln Gly Thr Thr Val Thr Val Ser Ser
1 5 10

<210> SEQ ID NO 409
<211> LENGTH: 108
<212> TYPE: PRT

-continued

<213> ORGANISM: Homo sapiens

<400> SEQUENCE: 409

```
Glu Ile Val Leu Thr Gln Ser Pro Gly Thr Leu Ser Leu Ser Pro Gly
 1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Val Phe Gly Gln Gly Thr Lys Leu Glu Ile Lys Arg
            100                 105
```

<210> SEQ ID NO 410
<211> LENGTH: 26
<212> TYPE: PRT
<213> ORGANISM: Homo sapiens

<400> SEQUENCE: 410

```
Glu Ile Val Leu Thr Gln Ser Pro Gly Thr Leu Ser Leu Ser Pro Gly
 1               5                   10                  15

Glu Arg Ala Thr Leu Ser Cys Arg Ala Ser
            20                  25
```

<210> SEQ ID NO 411
<211> LENGTH: 7
<212> TYPE: PRT
<213> ORGANISM: Homo sapiens

<400> SEQUENCE: 411

```
Gln Ser Val Ser Ser Ser Tyr
 1               5
```

<210> SEQ ID NO 412
<211> LENGTH: 17
<212> TYPE: PRT
<213> ORGANISM: Homo sapiens

<400> SEQUENCE: 412

```
Leu Ala Trp Tyr Gln Gln Lys Pro Gly Gln Ala Pro Arg Leu Leu Ile
 1               5                   10                  15

Tyr
```

<210> SEQ ID NO 413
<211> LENGTH: 3
<212> TYPE: PRT
<213> ORGANISM: Homo sapiens

<400> SEQUENCE: 413

```
Gly Ala Ser
 1
```

<210> SEQ ID NO 414
<211> LENGTH: 36
<212> TYPE: PRT
<213> ORGANISM: Homo sapiens -continued

```
<400> SEQUENCE: 414

Ser Arg Ala Thr Gly Ile Pro Asp Arg Phe Ser Gly Ser Gly Ser Gly
 1               5                  10                  15

Thr Asp Phe Thr Leu Thr Ile Ser Arg Leu Glu Pro Glu Asp Phe Ala
            20                  25                  30

Val Tyr Tyr Cys
        35


<210> SEQ ID NO 415
<211> LENGTH: 8
<212> TYPE: PRT
<213> ORGANISM: Homo sapiens

<400> SEQUENCE: 415

Gln Gln Tyr Gly Ser Ser Pro Val
 1               5


<210> SEQ ID NO 416
<211> LENGTH: 11
<212> TYPE: PRT
<213> ORGANISM: Homo sapiens

<400> SEQUENCE: 416

Phe Gly Gln Gly Thr Lys Leu Glu Ile Lys Arg
 1               5                  10
```

HUMAN MONOCLONAL ANTIBODIES AGAINST HENDRA AND NIPAH VIRUSES

RELATED APPLICATIONS

The present application is a U.S. National Phase Application of International Application PCT/US2005/040050, filed Nov. 4, 2005, which claims the benefit of U.S. Provisional Patent Application 60/661,766, filed Mar. 14, 2005, U.S. Provisional Patent Application 60/678,547, filed May 5, 2005, and U.S. Provisional Patent Application 60/718,902, filed Sep. 20, 2005, the disclosures of all of which are hereby expressly incorporated by reference in their entireties.

FIELD OF THE INVENTION

This invention relates generally to the field of immunology and specifically to monoclonal antibodies that bind or neutralize Hendra and Nipah viruses.

BACKGROUND OF THE INVENTION

Nipah virus (NiV) and Hendra virus (HeV) are closely related emerging paramyxoviruses that comprise the *Henipavirus* genus (Anonymous 1999 *MMWR Morb Mortal Wkly Rep* Ward, J. W. ed. 48:335-337; Chew, M. H. et al. 2000 *J Infect Dis* 181:1760-1763; Chua, K. B. et al. 2000 *Ann Neurol* 48:802-805; Eaton, B. T. 2001 *Microbes Infect* 3:277-278; Goh, K. J. et al. 2000 *N Engl J Med* 342:1229-1235; Lee, K. E. et al. 1999 *Ann Neurol* 46:428-432; Lim, C. C. et al. 2000 *Am J Neuroradiol* 21:455-461; Murray, K. et al. 1995 *Science* 268:94-97). Paramyxoviruses are negative-sense RNA containing enveloped viruses and contain two major membrane-anchored envelope glycoproteins that are required for infection of a receptive host cell. All members contain an F glycoprotein which mediates pH-independent membrane fusion between the virus and its host cell, while the second attachment glycoprotein can be either a hemagglutinin-neuraminidase protein (HN), a hemagglutinin protein (H), or a G protein depending on the particular virus (reviewed in Lamb, R. A. and Kolakofsky, D. 2001 in *Fields Virology*, eds. Knippe, D. M. & Howley, P. M., Lippincott Williams & Wilkins, Philadelphia, pp. 1305-1340). As with all paramyxoviruses, these glycoproteins are also the principal antigens to which virtually all neutralizing antibodies are directed.

The broad species tropisms and the ability to cause fatal disease in both animals and humans distinguish HeV and NiV from all other known paramyxoviruses (reviewed in Eaton, B. T. 2001 *Microbes Infect* 3:277-278). They are Biological Safety Level-4 (BSL-4) pathogens, and are on the NIAID Biodefense research agenda as zoonotic emerging category C priority pathogens that could be used as bioterror agents. The henipaviruses can be amplified and cause disease in large animals and be aerosol transmitted to humans where disease can be a severe respiratory illness and febrile encephalitis. They can be readily grown in cell culture or embryonated chicken eggs, produce high un-concentrated titers (~$10^8$ $TCID_{50}$/ml; Crameri, G. et al. 2002 *J Virol Methods* 99:41-51), and are highly infectious (Field, H. et al. 2001 *Microbes Infect* 3:307-314; Hooper, P. et al. 2001 *Microbes Infect* 3:315-322).

NiV has recently re-emerged in Bangladesh. Two outbreaks of NiV in 2004 have been confirmed, and yet another one occurred in January of 2005 (Anonymous 2005 *Communicable Disease Report Weekly* (*CDR Weekly*) Vol. 15 No. 16). Several important observations in these most recent outbreaks have been made, including a higher incidence of acute respiratory distress syndrome, person-to-person transmission, and significantly higher case fatality rates (60-75%) than in Malaysia (about 40%) where the virus was discovered or suspected to have originated (Anonymous 2004 *Wkly Epidemiol Rec* 79:168-171; Anonymous 2004 *Health and Science Bulletin* (*ICDDR,B*) 2:5-9; Butler, D. 2004 *Nature* 429:7; Enserink, M. 2004 *Science* 303:1121; Hsu, V. P. et al. 2004 *Emerg Infect Dis* 10:2082-2087). Currently, no therapeutics for NiV or HeV-infected individuals are available, and a vaccine for prevention of disease in human or livestock populations does not exist. Although antibody responses were detected in infections caused by these viruses, human monoclonal antibodies (hmabs) have not been identified against either virus. A number of studies have shown the importance of neutralizing antibodies in recovery and protection from viral infections (Dimitrov, D. S. 2004 *Nat Rev Microbiol* 2:109-122). Therefore, the development of neutralizing hmAbs against NiV and HeV could have important implications for prophylaxis and passive immunotherapy. In addition, the characterization of the epitopes of the neutralizing antibodies could provide helpful information for development of candidate vaccines and drugs. Finally, such antibodies could be used for diagnosis and as research reagents.

SEGUE TO THE INVENTION

Here, we report the identification of potent neutralizing hmAbs targeting the viral envelope glycoprotein G by using a highly purified, oligomeric, soluble HeV G (sG) glycoprotein as the antigen for screening of a large naïve human phage-display library. One of these antibodies exhibited exceptional potency against infectious HeV, and another one neutralized both HeV and NiV. Because these antibodies are fully human antibodies, they serve as the basis for prophylaxis and treatment of humans infected with HeV or NiV.

SUMMARY OF THE INVENTION

The present invention relates to monoclonal antibodies that bind or neutralize Hendra or Nipah virus. The invention provides such antibodies, fragments of such antibodies retaining Hendra or Nipah virus-binding ability, fully human antibodies retaining Hendra or Nipah virus-binding ability, and pharmaceutical compositions including such antibodies. The invention further provides for isolated nucleic acids encoding the antibodies of the invention and host cells transformed therewith. Additionally, the invention provides for prophylactic, therapeutic, and diagnostic methods employing the antibodies and nucleic acids of the invention.

BRIEF DESCRIPTION OF THE DRAWINGS

FIG. 8. CDR1-3s and FR1-4s for m101-117 and m102 mutants.

TABLE A

Figure 1A:
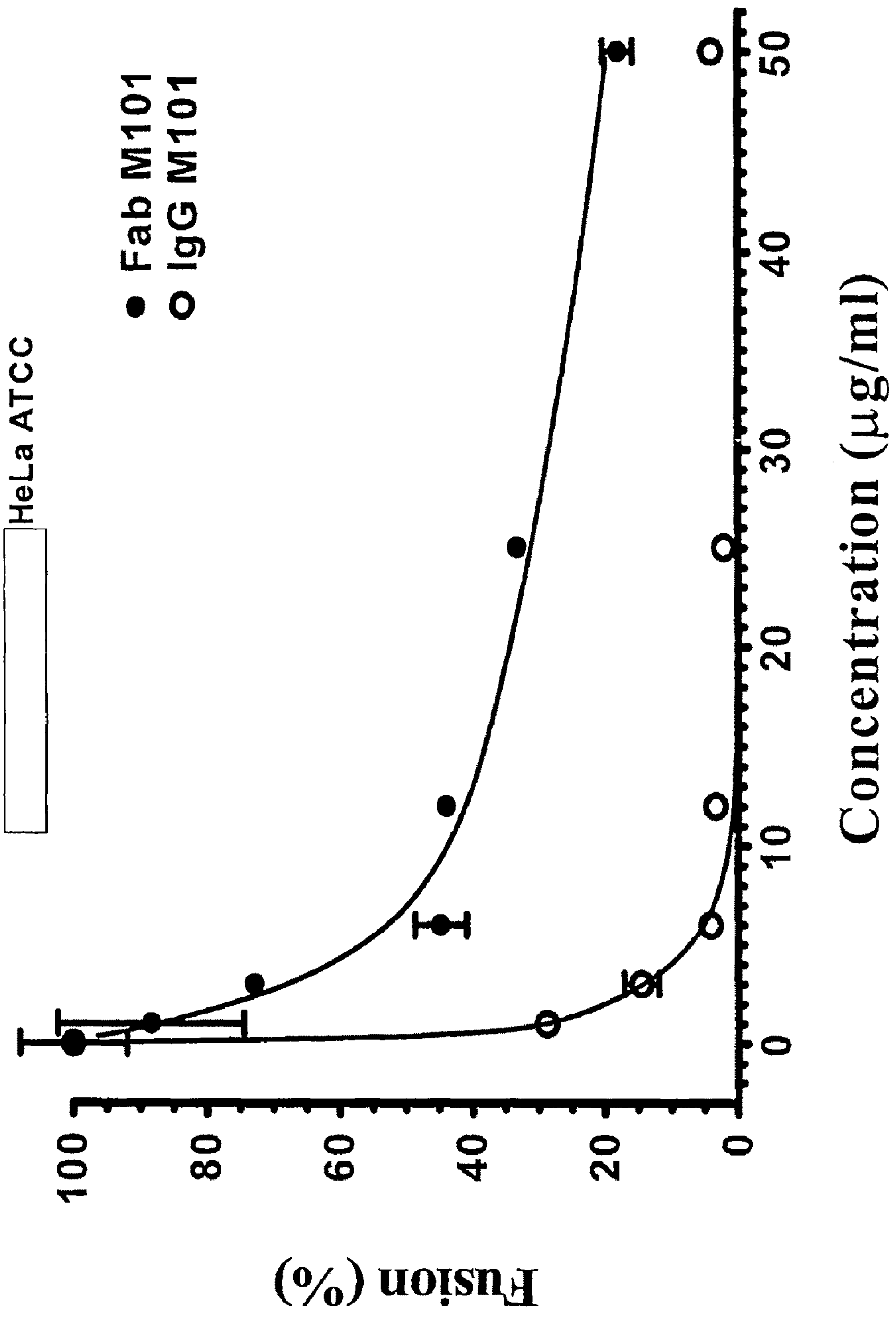
FIG. 1: Significantly higher inhibitory activity of IgG1 m101 than Fab m101 in HeV Env-mediated cell fusion. HeLa-USU cells were infected with *vaccinia* recombinants encoding HeV F and G glycoproteins, and with a *vaccinia* recombinant encoding T7 RNA polymerase (effector cells). Each designated target cell type was infected with the *E. coli* LacZ-encoding reporter *vaccinia* virus vCB21R. IgG1 m101 and Fab m101 were pre-incubated with effector cells and then mixed with target cells. The cell fusion assay was performed for 2.5 hr at 37° C. Fusion was measured as described in Example 1. Inhibition of HeV Env-mediated fusion by IgG1 m101 and Fab m101 in HeLa-ATCC cells is shown in A, and of PCI-13 cells—in B. Percentage of fusion is shown as function of the antibody concentration. The curves represent the best fit of the experimental data from which $IC_{50}$s were calculated using Prism GraphPad software.

Brief Description of m101-m117 SEQ ID NOs.

| | Heavy Chain SEQ ID NOs | | | | | | | | Light Chain SEQ ID NOs | | | | | | | |
|---|---|---|---|---|---|---|---|---|---|---|---|---|---|---|---|---|
| Fab/mab | $V_H$ | FR1 | CDR1 | FR2 | CDR2 | FR3 | CDR3 | FR4 | $V_L$ | FR1 | CDR1 | FR2 | CDR2 | FR3 | CDR3 | FR4 |
| m101 | 1 | 2 | 3 | 4 | 5 | 6 | 7 | 8 | 9 | 10 | 11 | 12 | 13 | 14 | 15 | 16 |
| m102 | 17 | 18 | 19 | 20 | 21 | 22 | 23 | 24 | 25 | 26 | 27 | 28 | 29 | 30 | 31 | 32 |
| m103 | 33 | 34 | 35 | 36 | 37 | 38 | 39 | 40 | 41 | 42 | 43 | 44 | 45 | 46 | 47 | 48 |
| m104 | 49 | 50 | 51 | 52 | 53 | 54 | 55 | 56 | 57 | 58 | 59 | 60 | 61 | 62 | 63 | 64 |
| m105 | 65 | 66 | 67 | 68 | 69 | 70 | 71 | 72 | 73 | 74 | 75 | 76 | 77 | 78 | 79 | 80 |
| m106 | 81 | 82 | 83 | 84 | 85 | 86 | 87 | 88 | 89 | 90 | 91 | 92 | 93 | 94 | 95 | 96 |
| m107 | 97 | 98 | 99 | 100 | 101 | 102 | 103 | 104 | 105 | 106 | 107 | 108 | 109 | 110 | 111 | 112 |
| m108 | 113 | 114 | 115 | 116 | 117 | 118 | 119 | 120 | 121 | 122 | 123 | 124 | 125 | 126 | 127 | 128 |
| m109 | 129 | 130 | 131 | 132 | 133 | 134 | 135 | 136 | 137 | 138 | 139 | 140 | 141 | 142 | 143 | 144 |
| m110 | 145 | 146 | 147 | 148 | 149 | 150 | 151 | 152 | 153 | 154 | 155 | 156 | 157 | 158 | 159 | 160 |
| m111 | 161 | 162 | 163 | 164 | 165 | 166 | 167 | 168 | 169 | 170 | 171 | 172 | 173 | 174 | 175 | 176 |
| m112 | 177 | 178 | 179 | 180 | 181 | 182 | 183 | 184 | 185 | 186 | 187 | 188 | 189 | 190 | 191 | 192 |
| m113 | 193 | 194 | 195 | 196 | 197 | 198 | 199 | 200 | 201 | 202 | 203 | 204 | 205 | 206 | 207 | 208 |
| m114 | 209 | 210 | 211 | 212 | 213 | 214 | 215 | 216 | 217 | 218 | 219 | 220 | 221 | 222 | 223 | 224 |
| m115 | 225 | 226 | 227 | 228 | 229 | 230 | 231 | 232 | 233 | 234 | 235 | 236 | 237 | 238 | 239 | 240 |
| m116 | 241 | 242 | 243 | 244 | 245 | 246 | 247 | 248 | 249 | 250 | 251 | 252 | 253 | 254 | 255 | 256 |
| m117 | 257 | 258 | 259 | 260 | 261 | 262 | 263 | 264 | 265 | 266 | 267 | 268 | 269 | 270 | 271 | 272 |

TABLE B

| Brief Description of Mutant m102 SEQ ID NOs. | | | | | | | | | | | | | | | | |
|---|---|---|---|---|---|---|---|---|---|---|---|---|---|---|---|---|
| Mutant | Heavy Chain SEQ ID NOs | | | | | | | | Light Chain SEQ ID NOs | | | | | | | |
| m102 | $V_H$ | FR1 | CDR1 | FR2 | CDR2 | FR3 | CDR3 | FR4 | $V_L$ | FR1 | CDR1 | FR2 | CDR2 | FR3 | CDR3 | FR4 |
| m102.2 | 273 | 274 | 275 | 276 | 277 | 278 | 279 | 280 | 281 | 282 | 283 | 284 | 285 | 286 | 287 | 288 |
| m102.3 | 289 | 290 | 291 | 292 | 293 | 294 | 295 | 296 | 297 | 298 | 299 | 300 | 301 | 302 | 303 | 304 |
| m102.4 | 305 | 306 | 307 | 308 | 309 | 310 | 311 | 312 | 313 | 314 | 315 | 316 | 317 | 318 | 319 | 320 |
| m102.5 | 321 | 322 | 323 | 324 | 325 | 326 | 327 | 328 | 329 | 330 | 331 | 332 | 333 | 334 | 335 | 336 |
| m102.11 | 337 | 338 | 339 | 340 | 341 | 342 | 343 | 344 | 345 | 346 | 347 | 348 | 349 | 350 | 351 | 352 |
| m102.12 | 353 | 354 | 355 | 356 | 357 | 358 | 359 | 360 | 361 | 362 | 363 | 364 | 365 | 366 | 367 | 368 |
| m102.13 | 369 | 370 | 371 | 372 | 373 | 374 | 375 | 376 | 377 | 378 | 379 | 380 | 381 | 382 | 383 | 384 |
| m102.15 | 385 | 386 | 387 | 388 | 389 | 390 | 391 | 392 | 393 | 394 | 395 | 396 | 397 | 398 | 399 | 400 |
| m102.16 | 401 | 402 | 403 | 404 | 405 | 406 | 407 | 408 | 409 | 410 | 411 | 412 | 413 | 414 | 415 | 416 |

DETAILED DESCRIPTION OF THE PREFERRED EMBODIMENT

Hendra virus (HeV) and Nipah virus (NiV) are closely related emerging viruses comprising the *Henipavirus* genus of the Paramyxovirinae. Each has a broad species tropism and can cause high mortality disease in both animal and human hosts. These viruses infect cells by a pH-independent membrane fusion event mediated by their attachment (G) and fusion (F) envelope glycoproteins (Envs). Seven Fabs, m101-7, were selected for their significant binding to a soluble form of Hendra G (sG) which was used as the antigen for panning of a large naïve human antibody library. The selected Fabs inhibited to various degrees cell fusion mediated by the HeV or NiV Envs and virus infection. The conversion of the most potent neutralizer of infectious HeV, Fab ml 0, to IgG1 significantly increased its cell fusion inhibitory activity—the $IC_{50}$ was decreased more than 10-fold to approximately 1 μg/ml. The IgG1 m101 was also exceptionally potent in neutralizing infectious HeV; complete (100%) neutralization was achieved with 12.5 μg/ml and 98% neutralization required only 1.6 μg/ml. The inhibition of fusion and infection correlated with binding of the Fabs to full-length G as measured by immunoprecipitation, and less with binding to sG as measured by ELISA and Biacore. M101 and m102 competed with the ephrin-B2, which we recently identified as a functional receptor for HeV and NiV, indicating a possible mechanism of neutralization by these antibodies. The m101, m102 and m103 antibodies competed with each other indicating that they bind to overlapping epitopes which are distinct from the epitopes of m106 and m107. In an initial attempt to localize the epitopes of m101 and m102 we measured their binding to a panel of 10 G alanine scanning mutants, and identified one residue, G183, which decreases binding of both m101 and m102 to G; it is localized at the base of the globular head of the G protein according to a model structure, and could be part of the antibody epitope that does not overlap with the receptor binding site on G. These results indicate that m101-7 are specific for HeV or NiV or both, and exhibit various neutralizing activity; they are the first human monoclonal antibodies identified against these viruses and are contemplated for use in treatment, prophylaxis and diagnosis, and as research reagents and serving as the basis for vaccines.

Definitions

Unless defined otherwise, technical and scientific terms used herein have the same meaning as commonly understood by one of ordinary skill in the art to which this invention belongs. See, e.g., Singleton P and Sainsbury D., *Dictionary of Microbiology and Molecular Biology* 3rd ed., J. Wiley & Sons, Chichester, New York, 2001, and *Fields Virology* 4th ed., Knipe D. M. and Howley P. M. eds, Lippincott Williams & Wilkins, Philadelphia 2001.

As used herein, the term "antibody" means an immunoglobulin molecule or a fragment of an immunoglobulin molecule having the ability to specifically bind to a particular antigen. Antibodies are well known to those of ordinary skill in the science of immunology. As used herein, the term "antibody" means not only full-length antibody molecules but also fragments of antibody molecules retaining antigen binding ability. Such fragments are also well known in the art and are regularly employed both in vitro and in vivo. In particular, as used herein, the term "antibody" means not only full-length immunoglobulin molecules but also antigen binding active fragments such as the well-known active fragments F(ab')2, Fab, Fv, and Fd.

As used herein, the terms "Hendra Virus Disease" and "Nipah Virus Disease" refer to diseases caused, directly or indirectly, by infection with Hendra or Nipah virus. The broad species tropisms and the ability to cause fatal disease in both animals and humans have distinguished Hendra virus (HeV) and Nipah virus (NiV) from all other known paramyxoviruses (Eaton B. T. 2001 *Microbes Infect* 3:277-278). These viruses can be amplified and cause disease in large animals and can be transmitted to humans where infection is manifested as a severe respiratory illness and/or febrile encephalitis.

As used herein with respect to polypeptides, the term "substantially pure" means that the polypeptides are essentially free of other substances with which they may be found in nature or in vivo systems to an extent practical and appropriate for their intended use. In particular, the polypeptides are sufficiently pure and are sufficiently free from other biological constituents of their host cells so as to be useful in, for example, generating antibodies, sequencing, or producing pharmaceutical preparations. By techniques well known in the art, substantially pure polypeptides may be produced in light of the nucleic acid and amino acid sequences disclosed herein. Because a substantially purified polypeptide of the invention may be admixed with a pharmaceutically acceptable carrier in a pharmaceutical preparation, the polypeptide may comprise only a certain percentage by weight of the preparation. The polypeptide is nonetheless substantially pure in that it has been substantially separated from the substances with which it may be associated in living systems.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

As used herein, a coding sequence and regulatory sequences are said to be "operably joined" when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribing and 5' non-translating sequences involved with initiation of transcription and translation respectively, such as a TATA box, capping sequence, CAAT sequence, and the like. Especially, such 5' non-transcribing regulatory sequences will include a promoter region which includes a promoter sequence for transcriptional control of the operably joined gene. Regulatory sequences may also include enhancer sequences or upstream activator sequences, as desired.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired: sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification and selection of cells which have been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

Novel Anti-HeV and NiV G Glycoprotein Monoclonal Antibodies

The present invention derives, in part, from the isolation and characterization of novel, fully human monoclonal antibodies that selectively bind to and neutralize Hendra and Nipah viruses. As described more fully below, these monoclonal antibodies have been shown to bind the G glycoprotein and to neutralize Hendra and Nipah viruses. The paratope of the anti-HeV and NiV Fab fragments associated with the neutralization epitope on the HeV and NiV glycoprotein G are defined by the amino acid (aa) sequences of the immunoglobulin heavy and light chain V-regions described in Tables A and B and SEQ ID NO: 1 through SEQ ID NO: 416.

In one set of embodiments, the present invention provides the full-length, fully human Hendra and Nipah monoclonal, antibodies in isolated form and in pharmaceutical preparations. Similarly, as described below, the present invention provides isolated nucleic acids, host cells transformed with nucleic acids, and pharmaceutical preparations including isolated nucleic acids, encoding the full-length, fully human Hendra and Nipah monoclonal antibodies. Finally, the present invention provides methods, as described more fully below, employing these antibodies and nucleic acids in the in vitro and in vivo diagnosis, prevention and therapy of Hendra Virus Disease or Nipah Virus Disease.

Significantly, as is well-known in the art, only a small portion of an antibody molecule, the paratope, is involved in the binding of the antibody to its epitope (see, in general, Clark, W. R. 1986 in *The Experimental Foundations of Modem Immunology* Wiley & Sons, Inc., New York; Roitt, I. 1991 in *Essential Immunology,* 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')2 fragment, retains both of the antigen binding sites of a full-length antibody. Similarly, an antibody from which the Fc region has been enzymatically cleaved, or which has been produced without the Fc region, designated an Fab fragment, retains one of the antigen binding sites of a full-length antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986, supra; Roitt, 1991, supra). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

The complete amino acid sequences of the antigen-binding Fab portions of the Hendra and Nipah monoclonal antibodies as well as the relevant FR and CDR regions are disclosed herein. SEQ ID NOs: 1, 17, 33, 49, 65, 81, 97, 113, 129, 145, 161, 177, 193, 209, 225, 241, 257, 273, 289, 305, 321, 337, 353, 369, 385, and 401 disclose the amino acid sequences of the Fd fragment of the Hendra and Nipah monoclonal antibodies. The amino acid sequences of the heavy chain FR1, CDR1, FR2, CDR2, FR3, CDR3 and FR4 regions are disclosed as (FR1, SEQ ID NOs: 2, 18, 34, 50, 66; 82, 98, 114, 130, 146, 162, 178, 194, 210, 226, 242, 258, 274, 290, 306, 322, 338, 354, 370, 386, and 402); (CDR1, SEQ ID NOs: 3, 19, 35, 51, 67, 83, 99, 115, 131, 147, 163, 179, 195, 211, 227, 243, 259, 275, 291, 307, 323, 339, 355, 371, 387, and 403); (FR2, SEQ ID NOs: 4, 20, 36, 52, 68, 84, 100, 116, 132, 148, 164, 180, 196, 212, 228, 244, 260, 276, 292, 308, 324, 340, 356, 372, 388, and 404); (CDR2, SEQ ID NOs: 5, 21, 37, 53, 69, 85, 101, 117, 133, 149, 165, 181, 197, 213, 229, 245, 261, 277, 293, 309, 325, 341, 357, 373, 389, and 405); (FR3, SEQ ID NOs: 6, 22, 38, 54, 70, 86, 102, 118, 134, 150, 166, 182, 198, 214, 230, 246, 262, 278, 294, 310, 326, 342, 358, 374, 390, and 406); (CDR3, SEQ ID NOs: 7, 23, 39, 55, 71, 87, 103, 119, 135, 151, 167, 183, 199, 215, 231, 247, 263, 279, 295, 311, 327, 343, 359, 375, 391, and 407); and (FR4, SEQ ID NOs: 8, 24, 40, 56, 72, 88, 104, 120, 136, 152, 168, 184, 200, 216, 232, 248, 264, 280, 296, 312, 328, 344, 360, 376, 392 and 408). SEQ ID NOs: 9, 25, 41, 57, 73, 89, 105, 121, 137, 153, 169, 185, 201, 217, 233, 249, 265, 281, 297, 313, 329, 345, 361, 377, 393 and 409 disclose the amino acid sequences of the light chains of the Hendra and Nipah monoclonal antibodies. The amino acid sequences of the light chain FR1, CDR1, FR2, CDR2, FR3, CDR3 and FR4 regions are disclosed as (FR1, SEQ ID NOs: 10, 26, 42, 58, 74, 90, 106, 122, 138, 154, 170, 186, 202, 218, 234, 250, 266, 282, 298, 314, 330, 346, 362, 378, 394, and 410); (CDR1, SEQ ID NOs: 11, 27, 43, 59, 75, 91, 107, 123, 139, 155, 171, 187, 203, 219, 235, 251, 267, 283, 299, 315, 331, 347, 363, 379, 395, and 411); (FR2, SEQ ID NOs: 12, 28, 44, 60, 76, 92, 108, 124, 140, 156, 172, 188, 204, 220, 236, 252, 268, 284, 300, 316, 332, 348, 364, 380, 396, and 412); (CDR2, SEQ ID NOs: 13, 29, 45, 61, 77, 93, 109, 125, 141, 157, 173, 189, 205, 221, 237, 253, 269, 285, 301, 317, 333, 349, 365, 381, 397, and 413); (FR3, SEQ ID NOs: 14, 30, 46, 62, 78, 94, 110, 126, 142, 158, 174, 190, 206, 222, 238, 254, 270, 286, 302, 318, 334, 350, 366, 382, 398, and 414); (CDR3, SEQ ID NOs: 15, 31, 47, 63, 79, 95, 111, 127, 143, 159, 175, 191, 207, 223, 239, 255, 271, 287, 303, 319, 335, 351, 367, 383, 399, and 415); (FR4, SEQ ID NOs: 16, 32, 48, 64, 80, 96, 112, 128, 144, 160, 176, 192, 208, 224, 240, 256, 272, 288, 304, 320, 336, 352, 368, 384, 400 and 416).

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of full-length antibodies with antigen-binding ability, are often referred to as "chimeric" antibodies.

Thus, as will be apparent to one of ordinary skill in the art, the present invention also provides for F(ab')2, Fab, Fv and Fd fragments of Hendra and Nipah monoclonal antibodies; chimeric antibodies in which the Fc and/or FR and/or, CDR1 and/or CDR2 and/or light chain CDR3 regions of the Hendra and Nipah monoclonal antibodies have been replaced by homologous human or non-human sequences; chimeric F(ab')2 fragment antibodies in which the FR and/or CDR1 and/or CDR2 and/or light chain CDR3 regions of the Hendra and Nipah monoclonal antibodies have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. Thus, those skilled in the art may alter the Hendra and Nipah monoclonal antibodies by the construction of CDR grafted or chimeric antibodies or antibody fragments containing all, or part thereof, of the disclosed heavy and light chain V-region CDR aa sequences (Jones, P. T. et al. 1986 *Nature* 321:522-525; Verhoeyen, M. et al. 1988 *Science* 39:1534-1536; and Tempest, P. R. et al. 1991 *Biotechnology* 9:266-271), without destroying the specificity of the antibodies for the G glycoprotein epitope. Such CDR grafted or chimeric antibodies or antibody fragments can be effective in prevention and treatment of Hendra or Nipah virus infection in animals (e.g., horses) and man.

In preferred embodiments, the chimeric antibodies of the invention are fully human monoclonal antibodies including at least the heavy chain CDR3 region of the Hendra and Nipah monoclonal antibodies. As noted above, such chimeric antibodies may be produced in which some or all of the FR regions of the Hendra and Nipah monoclonal antibodies have been replaced by other homologous human FR regions. In addition, the Fc portions may be replaced so as to produce IgA or IgM as well as IgG antibodies bearing some or all of the CDRs of the Hendra and Nipah monoclonal antibodies. Of particular importance is the inclusion of the Hendra and Nipah monoclonal antibodies heavy chain CDR3 region and, to a lesser extent, the other CDRs of the Hendra and Nipah monoclonal antibodies. Such fully human or chimeric antibodies will have particular utility in that they will not evoke an immune response against the antibody itself.

It is also possible, in accordance with the present invention, to produce chimeric antibodies including non-human sequences. Thus, one may use, for example, murine, ovine, equine, bovine or other mammalian Fc or FR sequences to replace some or all of the Fc or FR regions of the Hendra and Nipah monoclonal antibodies. Some of the CDRs may be replaced as well. Again, however, it is preferred that at least the heavy chain CDR3 of the Hendra and Nipah monoclonal antibodies, be included in such chimeric antibodies and, to a lesser extent, it is also preferred that some or all of the other CDRs of the Hendra and Nipah monoclonal antibodies be included. Such chimeric antibodies bearing non-human immunoglobulin sequences admixed with the CDRs of the human Hendra and Nipah monoclonal antibodies are not preferred for use in humans and are particularly not preferred for extended use because they may evoke an immune response against the non-human sequences. They may, of course, be used for brief periods or in immunosuppressed individuals but, again, fully human monoclonal antibodies are preferred. Because, however, Hendra and Nipah viruses also infect animals and because such antibodies may be used for brief periods or in immunosuppressed subjects, chimeric antibodies bearing non-human mammalian Fc and FR sequences but including at least the heavy chain CDR3 of the Hendra and Nipah monoclonal antibodies are contemplated as alternative embodiments of the present invention.

For inoculation or prophylactic uses, the antibodies of the present invention are preferably full-length antibody molecules including the Fc region. Such full-length antibodies will have longer half-lives than smaller fragment antibodies (e.g., Fab) and are more suitable for intravenous, intraperitoneal, intramuscular, intracavity, subcutaneous, or transdermal administration.

In some embodiments, Fab fragments, including chimeric Fab fragments, are preferred. Fabs offer several advantages over $F(ab')_2$ and whole immunoglobulin molecules for this therapeutic modality. First, because Fabs have only one binding site for their cognate antigen, the formation of immune complexes is precluded whereas such complexes can be generated when bivalent $F(ab')_2$ s and whole immunoglobulin molecules encounter their target antigen. This is of some importance because immune complex deposition in tissues can produce adverse inflammatory react-ions. Second, because Fabs lack an Fc region they cannot trigger adverse inflammatory reactions that are activated by Fc, such as activation of the complement cascade. Third, the tissue penetration of the small Fab molecule is likely to be much better than that of the larger whole antibody. Fourth, Fabs can be produced easily and inexpensively in bacteria, such as *E. coli*, whereas whole immunoglobulin antibody molecules require mammalian cells for their production in useful amounts. The latter entails transfection of immunoglobulin sequences into mammalian cells with resultant transformation. Amplification of these sequences must then be achieved by rigorous selective procedures and stable transformants must be identified and maintained. The whole immunoglobulin molecules must be produced by stably transformed, high expression mammalian cells in culture with the attendant problems of serum-containing culture medium. In contrast, production of Fabs in *E. coli* eliminates these difficulties and makes it possible to produce these antibody fragments in large fermenters which are less expensive than cell culture-derived products.

In addition to Fabs, smaller antibody fragments and epitope-binding peptides having binding specificity for the epitopes defined by the Hendra and Nipah monoclonal antibodies are also contemplated by the present invention and can also be used to bind or neutralize the virus. For example, single chain antibodies can be constructed according to the method of U.S. Pat. No. 4,946,778, to Ladner et al. Single chain antibodies comprise the variable regions of the light and heavy chains joined by a flexible linker moiety. Yet smaller is the antibody fragment known as the single domain antibody or Fd, which comprises an isolated $V_H$ single domain. Techniques for obtaining a single domain antibody with at least some of the binding specificity of the full-length antibody from which they are derived are known in the art.

It is possible to determine, without undue experimentation, if an altered or chimeric antibody has the same specificity as the Hendra and Nipah monoclonal antibodies by ascertaining whether the former blocks the latter from binding to G glycoprotein. If the monoclonal antibody being tested competes with the Hendra or Nipah monoclonal antibody as shown by a decrease in binding of the Hendra or Nipah monoclonal antibody, then it is likely that the two monoclonal antibodies bind to the same, or a closely spaced, epitope. Still another way to determine whether a monoclonal antibody has the specificity of the Hendra and Nipah monoclonal antibodies is to pre-incubate the Hendra or Nipah monoclonal antibody with G glycoprotein with which it is normally reactive, and then add the monoclonal antibody being tested to determine if the monoclonal antibody being tested is inhibited in its ability to bind G glycoprotein. If the monoclonal antibody being tested is inhibited then, in all likelihood, it has the same, or a functionally equivalent, epitope and specificity as the Hendra and Nipah monoclonal antibodies of the invention. Screening of Hendra and Nipah monoclonal antibodies also can be carried out by utilizing Hendra or Nipah viruses and determining whether the mAb neutralizes the virus.

By using the antibodies of the invention, it is now possible to produce anti-idiotypic antibodies which can be used to screen other monoclonal antibodies to identify whether the antibody has the same binding specificity as an antibody of the invention. In addition, such antiidiotypic antibodies can be used for active immunization (Herlyn, D. et al. 1986 *Science* 232:100-102). Such anti-idiotypic antibodies can be produced using well-known hybridoma techniques (Kohler, G. and Milstein, C. 1975 *Nature* 256:495-497). An anti-idiotypic antibody is an antibody which recognizes unique determinants present on the monoclonal antibody produced by the cell line of interest. These determinants are located in the hypervariable region of the antibody. It is this region which binds to a given epitope and, thus, is responsible for the specificity of the antibody. An anti-idiotypic antibody can be prepared by immunizing an animal with the monoclonal antibody of interest. The immunized animal will recognize and respond to the idiotypic determinants of the immunizing antibody and produce an antibody to these idiotypic determinants. By using the anti-idiotypic antibodies of the immunized animal, which are specific for the monoclonal antibodies of the invention, it is possible to identify other clones with the same idiotype as the antibody of the hybridoma used for immunization. Idiotypic identity between monoclonal antibodies of two cell lines demonstrates that the two monoclonal antibodies are the same with respect to their recognition of the same epitopic determinant. Thus, by using anti-idiotypic antibodies, it is possible to identify other hybridomas expressing monoclonal antibodies having the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the image of the epitope bound by the first monoclonal antibody. Thus, the anti-idiotypic monoclonal antibody can be used, for immunization, since the anti-idiotype monoclonal antibody binding domain effectively acts as an antigen.

Nucleic Acids Encoding Anti-HeV and NiV G Glycoprotein Antibodies

Given the disclosure herein of the amino acid sequences of the heavy chain Fd and light chain variable domains of the Hendra and Nipah monoclonal antibodies, one of ordinary skill in the art is now enabled to produce nucleic acids which encode this antibody or which encode the various fragment antibodies or chimeric antibodies described above. It is contemplated that such nucleic acids will be operably joined to other nucleic acids forming a recombinant vector for cloning or for expression of the antibodies of the invention. The present invention includes any recombinant vector containing the coding sequences, or part thereof, whether for prokaryotic or eukaryotic transformation, transfection or gene therapy. Such vectors may be prepared using conventional molecular biology techniques, known to those with skill in the art, and would comprise DNA coding sequences for the immunoglobulin V-regions of the Hendra and Nipah monoclonal antibodies, including framework and CDRs or parts thereof, and a suitable promoter either with (Whittle, N. et al. 1987 *Protein Eng* 1:499-505 and Burton, D. R. et al. 1994 *Science* 266: 1024-1027) or without (Marasco, W. A. et al. 1993. *Proc Natl Acad Sci USA* 90:7889-7893 and Duan, L. et al. 1994 *Proc Natl Acad Sci USA* 91:5075-5079) a signal sequence for export or secretion. Such vectors may be transformed or transfected into prokaryotic (Huse, W. D. et al. 1989 *Science* 246:1275-1281; Ward, S. et al. 1989 *Nature* 341:544-546; Marks, J. D. et al. 1991 *J Mol Biol* 222:581-597; and Barbas, C. F. et al. 1991 *Proc Natl Acad Sci USA* 88:7978-7982) or eukaryotic (Whittle, N. et al. 1987 *Protein Eng* 1:499-505 and Burton, D. R. et al. 1994 *Science* 266:1024-1027) cells or used for gene therapy (Marasco, W. A. et al. 1993 *Proc Natl Acad Sci USA* 90:7889-7893 and Duan, L. et al. 1994 *Proc Natl Acad Sci USA* 91:5075-5079) by conventional techniques, known to those with skill in the art.

The expression vectors of the present invention include regulatory sequences operably joined to a nucleotide sequence encoding one of the antibodies of the invention. As used herein, the term "regulatory sequences" means nucleotide sequences which are necessary for or conducive to the transcription of a nucleotide sequence which encodes a desired polypeptide and/or which are necessary for or conducive to the translation of the resulting transcript into the desired polypeptide. Regulatory sequences include, but are not limited to, 5' sequences such as operators, promoters and ribosome binding sequences, and 3' sequences such as polyadenylation signals. The vectors of the invention may optionally include 5' leader or signal sequences, 5' or 3' sequences encoding fusion products to aid in protein purification, and various markers which aid in the identification or selection of transformants. The choice and design of an appropriate vector is within the ability and discretion of one of ordinary skill in the art. The subsequent purification of the antibodies may be accomplished by any of a variety of standard means known in the art.

A preferred vector for screening monoclonal antibodies, but not necessarily preferred for the mass production of the antibodies of the invention, is a recombinant DNA molecule containing a nucleotide sequence that codes for and is capable of expressing a fusion polypeptide containing, in the direction of amino- to carboxy-terminus, (1) a prokaryotic secretion signal domain, (2) a polypeptide of the invention, and, optionally, (3) a fusion protein domain. The vector includes DNA regulatory sequences for expressing the fusion polypeptide, preferably prokaryotic, regulatory sequences. Such vectors can be constructed by those with skill in the art and have been described by Smith, G. P. et al. (1985 *Science* 228:13151317); Clackson, T. et al. (1991 *Nature* 352:624-628); Kang et al. (1991 in *Methods: A Companion to Methods in Enzymology*, vol. 2, R. A. Lerner and D. R. Burton, ed. Academic Press, NY, pp 111-118); Batbas, C. F. et al. (1991 *Proc Natl Acad Sci USA* 88:7978-7982); Roberts, B. L. et al. (1992 *Proc Natl Acad Sci USA* 89:2429-2433).

A fusion polypeptide may be useful for purification of the antibodies of the invention. The fusion domain may, for example, include a poly-His tail which allows for purification on $Ni^{+}$ columns or the maltose binding protein of the commercially available vector pMAL (New England BioLabs, Beverly, Mass.). A currently preferred, but by no means necessary, fusion domain is a filamentous phage membrane anchor. This domain is particularly useful for screening phage display libraries of monoclonal antibodies but may be of less utility for the mass production of antibodies. The filamentous phage membrane anchor is preferably a domain of the cpIII or cpVIII coat protein capable of associating with the matrix of a filamentous phage particle, thereby incorporating the fusion polypeptide onto the phage surface, to enable solid phase binding to specific antigens or epitopes and thereby allow enrichment and selection of the specific antibodies or fragments encoded by the phagemid vector.

The secretion signal is a leader peptide domain of a protein that targets the protein to the membrane of the host cell, such as the periplasmic membrane of Gram-negative bacteria. A preferred secretion signal for *E. coli* is a pelB secretion signal. The leader sequence of the pelB protein has previously been used as a secretion signal for fusion proteins (Better, M. et al. 1988 *Science* 240:1041-1043; Sastry, L. et al. 1989 *Proc Natl Acad Sci USA* 86:5728-5732; and Mullinax, R. L. et al., 1990 *Proc Natl Acad Sci USA* 87:8095-8099). Amino acid residue sequences for other secretion signal polypeptide domains from *E. coli* useful in this invention can be found in Neidhard, F. C. (ed.), 1987 in *Escherichia coli* and *Salmonella Typhimurium: Typhimurium Cellular and Molecular Biology*, American Society for Microbiology, Washington, D.C.

To achieve high levels of gene expression in *E. coli*, it is necessary to use not only strong promoters to generate large quantities of mRNA, but also ribosome binding sites to ensure that the mRNA is efficiently translated. In *E. coli*, the ribosome binding site includes an initiation codon (AUG) and a sequence 3-9 nucleotides long located 3-11 nucleotides upstream from the initiation codon (Shine J. and Dalgamo L. 1975 *Nature* 254:34-38). The sequence, which is called the Shine-Dalgarno (SD) sequence, is complementary to the 3' end of *E. coli* 16S rRNA. Binding of the ribosome to mRNA and the sequence at the 3' end of the mRNA can be affected by several factors: the degree of complementarity between the SD sequence and 3' end of the 16S rRNA; the spacing lying between the SD sequence and the AUG; and the nucleotide sequence following the AUG, which affects ribosome binding. The 3' regulatory sequences define at least one termination (stop) codon in frame with and operably joined to the heterologous fusion polypeptide.

In preferred embodiments with a prokaryotic expression host, the vector utilized includes a prokaryotic origin of replication or replicon, i.e., a DNA sequence having the ability to direct autonomous replication and maintenance of the recombinant DNA molecule extrachromosomally in a prokaryotic host cell, such as a bacterial host cell, transformed therewith. Such origins of replication are well known in the art. Preferred origins of replication are those that are efficient in the host organism. A preferred host cell is *E. coli*. For use of a vector in *E. coli*, a preferred origin of replication is ColEI found in pBR322 and a variety of other common plasmids. Also preferred is the p15A origin of replication found on pACYC and its derivatives. The ColEI and p15A replicons have been extensively utilized in molecular biology, are available on a variety of plasmids and are described by Sambrook et al., 1989, in *Molecular Cloning: A Laboratory Manual*, 2nd edition, Cold Spring Harbor Laboratory Press.

In addition, those embodiments that include a prokaryotic replicon preferably also include a gene whose expression confers a selective advantage, such as drug resistance, to a bacterial host transformed therewith. Typical bacterial drug resistance genes are those that confer resistance to ampicillin, tetracycline, neomycin/kanamycin or chloramphenicol. Vectors typically also contain convenient restriction sites for insertion of translatable DNA sequences. Exemplary vectors are the plasmids pUC18 and pUC19 and derived vectors such as those commercially available from suppliers such as Invitrogen (San Diego, Calif.).

When the antibodies of the invention include both heavy chain and light chain sequences, these sequences may be encoded on separate vectors or, more conveniently, may be expressed by a single vector. The heavy and light chain may, after translation or after secretion, form the heterodimeric structure of natural antibody molecules. Such a heterodimeric antibody may or may not be stabilized by disulfide bonds between the heavy and light chains.

A vector for expression of heterodimeric antibodies, such as the full-length antibodies of the invention or the $F(ab')_2$, Fab or Fv fragment antibodies of the invention, is a recombinant DNA molecule adapted for receiving and expressing translatable first and second DNA sequences. That is, a DNA expression vector for expressing a heterodimeric antibody provides a system for independently cloning (inserting) the two translatable DNA sequences into two separate cassettes present in the vector, to form two separate cistrons for expressing the first and second polypeptides of a heterodimeric antibody. The DNA expression vector for expressing two cistrons is referred to as a dicistronic expression vector.

Preferably, the vector comprises a first cassette that includes upstream and downstream DNA regulatory sequences operably joined via a sequence of nucleotides adapted for directional ligation to an insert DNA. The upstream translatable sequence preferably encodes the secretion signal as described above. The cassette includes DNA regulatory sequences for expressing the first antibody polypeptide that is produced when an insert translatable DNA sequence (insert DNA) is directionally inserted into the cassette via the sequence of nucleotides adapted for directional ligation.

The dicistronic expression vector also contains a second cassette for expressing the second antibody polypeptide. The second cassette includes a second translatable DNA sequence that preferably encodes a secretion signal, as described above, operably joined at its 3' terminus via a sequence of nucleotides adapted for directional ligation to a downstream DNA sequence of the vector that typically defines at least one stop codon in the reading frame of the cassette. The second translatable DNA sequence is operably joined at its 5' terminus to DNA regulatory sequences forming the 5' elements. The second cassette is capable, upon insertion of a translatable DNA sequence (insert DNA), of expressing the second fusion polypeptide comprising a secretion signal with a polypeptide coded by the insert DNA.

The antibodies of the present invention may additionally, of course, be produced by eukaryotic cells such as CHO cells, human or mouse hybridomas, immortalized B-lymphoblastoid cells, and the like. In this case, a vector is constructed in which eukaryotic regulatory sequences are operably joined to the nucleotide sequences encoding the antibody polypeptide or polypeptides. The design and selection of an appropriate eukaryotic vector is within the ability and discretion of one of ordinary skill in the art. The subsequent purification of the antibodies may be accomplished by any of a variety of standard means known in the art.

The antibodies of the present invention may furthermore, of course, be produced in plants. In 1989, Hiatt A. et al. 1989 *Nature* 342:76-78 first demonstrated that functional antibodies could be produced in transgenic plants. Since then, a considerable amount of effort has been invested in developing plants for antibody (or "plantibody") production (for reviews see Giddings, G. et al. 2000 *Nat Biotechnol* 18:1151-1155; Fischer, R. and Emans, N. 2000 *Transgenic Res* 9:279-299). Recombinant antibodies can be targeted to seeds, tubers, or fruits, making administration of antibodies in such plant tissues advantageous for immunization programs in developing countries and worldwide.

In another embodiment, the present invention provides host cells, both prokaryotic and eukaryotic, transformed or transfected with, and therefore including, the vectors of the present invention.

Diagnostic and Pharmaceutical Anti-HeV and NiV G Glycoprotein Antibody Preparations The invention also relates to a method for preparing diagnostic or pharmaceutical compositions comprising the monoclonal antibodies of the invention or polynucleotide sequences encoding the antibodies of the invention or part thereof, the pharmaceutical compositions being used for immunoprophylaxis or immunotherapy of Hendra Virus Disease or Nipah Virus Disease. The pharmaceutical preparation includes a pharmaceutically acceptable carrier. Such carriers, as used herein, means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

A preferred embodiment of the invention relates to monoclonal antibodies whose heavy chains comprise in CDR3 the polypeptide having SEQ ID NO: 7, and/or whose light chains comprise in CDR3 the polypeptide having SEQ ID NO: 15; whose heavy chains comprise in CDR3 the polypeptide having SEQ ID NO: 23, and/or whose light chains comprise in CDR3 the polypeptide having SEQ ID NO: 31; whose heavy chains comprise in CDR3 the polypeptide having SEQ ID NO: 39, and/or whose light chains comprise in CDR3 the polypeptide having SEQ ID NO: 47; whose heavy chains comprise in CDR3 the polypeptide having SEQ ID NO: 55, and/or whose light chains comprise in CDR3 the polypeptide having SEQ ID NO: 63; whose heavy chains comprise in CDR3 the polypeptide having SEQ ID NO: 71, and/or whose light chains comprise in CDR3 the polypeptide having SEQ ID NO: 79; whose heavy chains comprise in CDR3 the polypeptide having SEQ ID NO: 87, and/or whose light chains comprise in CDR3 the polypeptide having SEQ ID NO: 95; whose heavy chains comprise in CDR3 the polypeptide having SEQ ID NO: 103, and/or whose light chains comprise in CDR3 the polypeptide having SEQ ID NO: 111; whose heavy chains comprise in CDR3 the polypeptide having SEQ ID NO: 119, and/or whose light chains comprise in CDR3 the polypeptide having SEQ ID NO: 127; whose heavy chains comprise in CDR3 the polypeptide having SEQ ID NO: 135, and/or whose light chains comprise in CDR3 the polypeptide having SEQ ID NO: 143; whose heavy chains comprise in CDR3 the polypeptide having SEQ ID NO: 151, and/or whose light chains comprise in CDR3 the polypeptide having SEQ ID NO: 159; whose heavy chains comprise in CDR3 the polypeptide having SEQ ID NO: 167, and/or whose light chains comprise in CDR3 the polypeptide having SEQ ID NO: 175; whose heavy chains comprise in CDR3 the polypeptide having SEQ ID NO: 183, and/or whose light chains comprise in CDR3 the polypeptide having SEQ ID NO: 191; whose heavy chains comprise in CDR3 the polypeptide having SEQ ID NO: 199, and/or whose light chains comprise in CDR3 the polypeptide having SEQ ID NO: 207; whose heavy chains comprise in CDR3 the polypeptide having SEQ ID NO: 215, and/or whose light chains comprise in CDR3 the polypeptide having SEQ ID NO: 223; whose heavy chains comprise in CDR3 the polypeptide having SEQ ID NO: 231, and/or whose light chains comprise in CDR3 the polypeptide having SEQ ID NO: 239; whose heavy chains comprise in CDR3 the polypeptide having SEQ. ID NO: 247, and/or whose light chains comprise in CDR3 the polypeptide having SEQ ID NO: 255; whose heavy chains comprise in CDR3 the polypeptide having SEQ ID NO: 263, and/or whose light chains comprise in CDR3 the polypeptide having SEQ ID NO: 271; whose heavy chains comprise in CDR3 the polypeptide having SEQ ID NO: 279, and/or whose light chains comprise in CDR3 the polypeptide having SEQ ID NO: 287; whose heavy chains comprise in CDR3 the polypeptide having SEQ ID NO: 295, and/or whose light chains comprise in CDR3 the polypeptide having SEQ ID NO: 303; whose heavy chains comprise in CDR3 the polypeptide having SEQ ID NO: 311, and/or whose light chains comprise in CDR3 the polypeptide having SEQ ID NO: 319; whose heavy chains comprise in CDR3 the polypeptide having SEQ ID NO: 327, and/or whose light chains comprise in CDR3 the polypeptide having SEQ ID NO: 335; whose heavy chains comprise in CDR3 the polypeptide having SEQ ID NO: 343, and/or whose light chains comprise in CDR3 the polypeptide having SEQ ID NO: 351; whose heavy chains comprise in CDR3 the polypeptide having SEQ ID NO: 359, and/or whose light chains comprise in CDR3 the polypeptide having SEQ ID NO: 367; whose heavy chains comprise in CDR3 the polypeptide having SEQ ID NO: 375, and/or whose light chains comprise in CDR3 the polypeptide having SEQ ID NO: 383; whose heavy chains comprise in CDR3 the polypeptide having SEQ ID NO: 391, and/or whose light chains comprise in CDR3 the polypeptide having SEQ ID NO: 399; whose heavy chains comprise in CDR3 the polypeptide having SEQ ID NO: 407, and/or whose light chains comprise in CDR3 the polypeptide having SEQ ID NO: 415; and conservative variations of these peptides. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies having the substituted polypeptide also bind or neutralize Hendra or Nipah virus. Analogously, another preferred embodiment of the invention relates to polynucleotides which encode the above noted heavy chain polypeptides and to polynucleotide sequences which are complementary to these polynucleotide sequences. Complementary polynucleotide sequences include those sequences that hybridize to the polynucleotide sequences of the invention under stringent hybridization conditions.

The anti-Hendra and Nipah antibodies of the invention may be labeled by a variety of means for use in diagnostic and/or pharmaceutical applications. There are many different labels and methods of labeling known to those of ordinary skill in the art. Examples of the types of labels which can be used in the present invention include enzymes, radioisotopes, fluorescent compounds, colloidal metals, chemiluminescent compounds; and bioluminescent compounds. Those of ordinary skill in the art will know of other suitable labels for binding to the monoclonal antibodies of the invention, or will be able to ascertain such, using routine experimentation. Furthermore, the binding of these labels to the monoclonal antibodies of the invention can be done using standard techniques common to those of ordinary skill in the art.

Another labeling technique which may result in greater sensitivity consists of coupling the antibodies to low molecular weight haptens. These haptens can then be specifically altered by means of a second reaction. For example, it is common to use haptens such as biotin, which reacts with avidin, or dinitrophenol, pyridoxal, or fluorescein, which can react with specific anti-hapten antibodies.

The materials for use in the assay of the invention are ideally suited for the preparation of a kit. Such a kit may comprise a carrier means being compartmentalized to receive in close confinement one or more container means such as vials, tubes, and the like, each of the container means comprising one of the separate elements to be used in the method. For example, one of the container means may comprise a monoclonal antibody of the invention that is, or can be, detectably labeled. The kit may also have containers containing buffer(s) and/or a container comprising a reporter-means, such as a biotin-binding protein, such as avidin or streptavidin, bound to a reporter molecule, such as an enzymatic or fluorescent label.

In vitro Detection and Diagnostics

The monoclonal antibodies of the invention are suited for in vitro use, for example, in immunoassays in which they can be utilized in liquid phase or bound to a solid phase carrier. In addition, the monoclonal antibodies in these immunoassays can be detectably labeled in various ways. Examples of types of immunoassays which can utilize the monoclonal antibodies of the invention are competitive and non-competitive immunoassays in either a direct or indirect format. Examples of such immunoassays are the radioimmunoassay (RIA) and the sandwich (immunometric) assay. Detection of antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The monoclonal antibodies of the invention can be bound to many different carriers and used to detect the presence of Hendra or Nipah virus. Examples of well-known carriers include glass, polystyrene, polypropylene, polyethylene, dextran, nylon, amylase, natural and modified cellulose, polyacrylamide, agarose and magnetite. The nature of the carrier can be either soluble or insoluble for purposes of the invention. Those skilled in the art will know of other suitable carriers for binding monoclonal antibodies, or will be able to ascertain such, using routine experimentation.

For purposes of the invention, Hendra or Nipah virus may be detected by the monoclonal antibodies of the invention when present in biological fluids and tissues. Any sample containing a detectable amount of Hendra or Nipah virus can be used. A sample can be a liquid such as urine, saliva, cerebrospinal fluid, blood, serum or the like; a solid or semi-solid such as tissues, feces, or the like; or, alternatively, a solid tissue such as those commonly used in histological diagnosis.

In vivo Detection of Hendra or Nipah Virus

In using the monoclonal antibodies of the invention for the in vivo detection of antigen, the detectably labeled monoclonal antibody is given in a dose which is diagnostically effective. The term "diagnostically effective" means that the amount of detectably labeled monoclonal antibody is administered in sufficient quantity to enable detection of the site having the Hendra or Nipah virus antigen for which the monoclonal antibodies are specific.

The concentration of detectably labeled monoclonal antibody which is administered should be sufficient such that the binding to Hendra or Nipah virus is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. The dosage of monoclonal antibody can vary from about 0.01 mg/kg to about 50 mg/kg, preferably 0.1 mg/kg to about 20 mg/kg, most preferably about 0.1 mg/kg to about 2 mg/kg. Such dosages may vary, for example, depending on whether multiple injections are given, on the tissue being assayed, and other factors known to those of skill in the art.

For in vivo diagnostic imaging, the type of detection instrument available is a major factor in selecting an appropriate radioisotope. The radioisotope chosen must have a type of decay which is detectable for the given type of instrument. Still another important factor in selecting a radioisotope for in vivo diagnosis is that the half-life of the radioisotope be long enough such that it is still detectable at the time of maximum uptake by the target, but short enough such that deleterious radiation with respect to the host is acceptable. Ideally, a radioisotope used for in vivo imaging will lack a particle emission but produce a large number of photons in the 140-250 keV range, which may be readily detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions are the bifunctional chelating agents such as diethylenetriaminepentacetic acid (DTPA) and ethylenediaminetetra-acetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr and $^{56}$Fe.

The monoclonal antibodies of the invention can be used in vitro and in vivo to monitor the course of Hendra Virus Disease or Nipah Virus Disease therapy. Thus, for example, by measuring the increase or decrease in the number of cells infected with Hendra or Nipah virus or changes in the concentration of Hendra or Nipah virus present in the body or in various body fluids, it would be possible to determine whether a particular therapeutic regimen aimed at ameliorating Hendra Virus Disease or Nipah Virus Disease is effective.

Prophylaxis and Therapy of Hendra Virus Disease and Nipah Virus Disease

The monoclonal antibodies can also be used in prophylaxis and as therapy for Hendra Virus Disease and Nipah Virus Disease in both humans and other animals. The terms, "prophylaxis" and "therapy" as used herein in conjunction with the monoclonal antibodies of the invention denote both prophylactic as well as therapeutic administration and both passive immunization with substantially purified polypeptide products, as well as gene therapy by transfer of polynucleotide sequences encoding the product or part thereof. Thus, the monoclonal antibodies can be administered to high-risk subjects in order to lessen the likelihood and/or severity of Hendra Virus Disease and Nipah Virus Disease or administered to subjects already evidencing active Hendra or Nipah virus infection. In the present invention, Fab fragments also bind or neutralize Hendra or Nipah virus and therefore may be used to treat infection but full-length antibody molecules are otherwise preferred.

As used herein, a "prophylactically effective amount" of the monoclonal antibodies of the invention is a dosage large enough to produce the desired effect in the protection of individuals against Hendra or Nipah virus infection for a reasonable period of time, such as one to two months or longer following administration. A prophylactically effective amount is not, however, a dosage so large as to cause adverse side effects, such as hyperviscosity syndromes, pulmonary edema, congestive heart failure, and the like. Generally, a prophylactically effective amount may vary with the subject's age, condition, and sex, as well as the extent of the disease in the subject and can be determined by one of skill in the art. The dosage of the prophylactically effective amount may be adjusted by the individual physician or veterinarian in the event of any complication. A prophylactically effective amount may vary from about 0.01 mg/kg to about 50 mg/kg, preferably from about 0.1 mg/kg to about 20 mg/kg, most preferably from about 0.2 mg/kg to about 2 mg/kg, in one or more administrations (priming and boosting).

As used herein, a "therapeutically effective amount" of the monoclonal antibodies of the invention is a dosage large enough to produce the desired effect in which the symptoms of Hendra Virus Disease or Nipah Virus Disease are ameliorated or the likelihood of infection is decreased. A therapeutically effective amount is not, however, a dosage so large as to cause adverse side effects, such as hyperviscosity syndromes, pulmonary edema, congestive heart failure, and the like. Generally, a therapeutically effective amount may vary with the subject's age, condition, and sex, as well as the extent of the disease in the subject and can be determined by one of skill in the art. The dosage of the therapeutically effective amount may be adjusted by the individual physician or veterinarian in the event of any complication. A therapeutically effective amount may vary from about 0.01 mg/kg to about 50 mg/kg, preferably from about 0.1 mg/kg to about 20 mg/kg, most preferably from about 0.2 mg/kg to about 2 mg/kg, in one or more dose administrations daily, for one or several days. Preferred is administration of the antibody for 2 to 5 or more consecutive days in order to avoid "rebound" of virus replication from occurring.

The monoclonal antibodies of the invention can be administered by injection or by gradual infusion over time. The administration of the monoclonal antibodies of the invention may, for example, be intravenous, intraperitoneal, intramuscular, intracavity, subcutaneous, or transdermal. Techniques for preparing injectate or infusate delivery systems containing antibodies are well known to those of skill in the art. Generally, such systems should utilize components which will not significantly impair the biological properties of the antibodies, such as the paratope binding capacity (see, for example, Remington's Pharmaceutical Sciences, 18th edition, 1990, Mack Publishing). Those of skill in the art can readily determine the various parameters and conditions for producing antibody injectates or infusates without resort to undue experimentation.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and the like.

Potent Neutralization of Hendra and Nipah Viruses by Human Monoclonal Antibodies Selection of Phage-displayed Fabs (m101-7) Specific for Hendra Virus Soluble G Glycoprotein (sG)

Our initial efforts to develop G-specific human monoclonal antibodies (hmAbs) by using cell-associated G and synthetic antibody libraries as well as an immune library constructed from frozen lymphocytes of a survivor from Nipah infection have not been successful. To develop hmAbs against the G envelope glycoprotein of HeV and NiV we used a large naïve human Fab library containing about $10^{10}$ different phage-displayed Fabs we have recently developed. Here, we have made use of a unique soluble and secreted form of the attachment (G) glycoprotein of HeV (sG) which we have recently produced and characterized (Bossart, K. N. et al. 2005 *J Virol* 79:6690-6702). This protein was used as an antigen for screening of the antibody library. After four rounds of panning, screening of 380 individual phage clones was performed in phage ELISA with sG as described in Example 1. Of those, 71 clones that exhibited significant binding to sG were sequenced. Seventeen Fabs had unique sequences (Table 1). They were expressed in bacteria, purified and tested for binding activity. Seven Fabs, designated m101 through m107, exhibited significant (A450>0.5) binding to sG in ELISA (Table 1). Notably, on average, the heavy chain CDR3s (H3) of the binders (m101-7) were significantly longer than those of Fabs that bind weaker (m108-17) (Table 1). Interestingly, the heavy chains of m101 and m102 (the most potent HeV and NiV neutralizers—see below) were the most divergent from the germ line heavy chains indicating a certain level of maturation although they are IgM specific. The light chains were from all Ig classes and show greater variation as compared to the germ line light chains (Table 2).

Inhibition of HeV Env-mediated Fusion by the Selected Fabs

To test the neutralizing activity of the antibodies we first measured their ability to inhibit fusion mediated by HeV envelope glycoprotein (Env) expressing cells with cells that we had previously identified as fusion-competent. Fusion was measured by two assays—a reporter gene assay and a syncytia formation assay. The seven Fabs that bound strongly to sG (Table 1) also exhibited measurable inhibitory activity in the reporter gene assay (Table 3) and were selected for further characterization. They also inhibited syncytia formation to various degrees in general correlation with the inhibitory activity measured by the reporter gene assay. Interestingly, six of the seven Fabs also inhibited to various degrees NiV Env-mediated fusion (Table 3). One antibody, m101, was most active against HeV Env-mediated fusion, while another one, m102, exhibited the highest cross-inhibitory activity against both HeV- and NiV Env-mediated fusion.

Neutralization of HeV and NiV by Fabs

The inhibitory activity of these Fabs was further tested by using infectious HeV and NiV in a neutralization assay as described in the Example 1. When tested at concentrations above 80 μg/ml, Fab m101 showed neutralizing activity against HeV but not against NiV, and Fab m102 exhibited weaker neutralizing activity against HeV as compared to m101. Interestingly, as in the cell fusion assay, m102 exhibited cross-neutralizing activity for both HeV and NiV. The other tested Fabs did not show measurable neutralizing activity when tested at concentrations up to 100 μg/ml. These results indicated that two of the selected Fabs could neutralize infectious HeV and NiV.

Figure 1B:
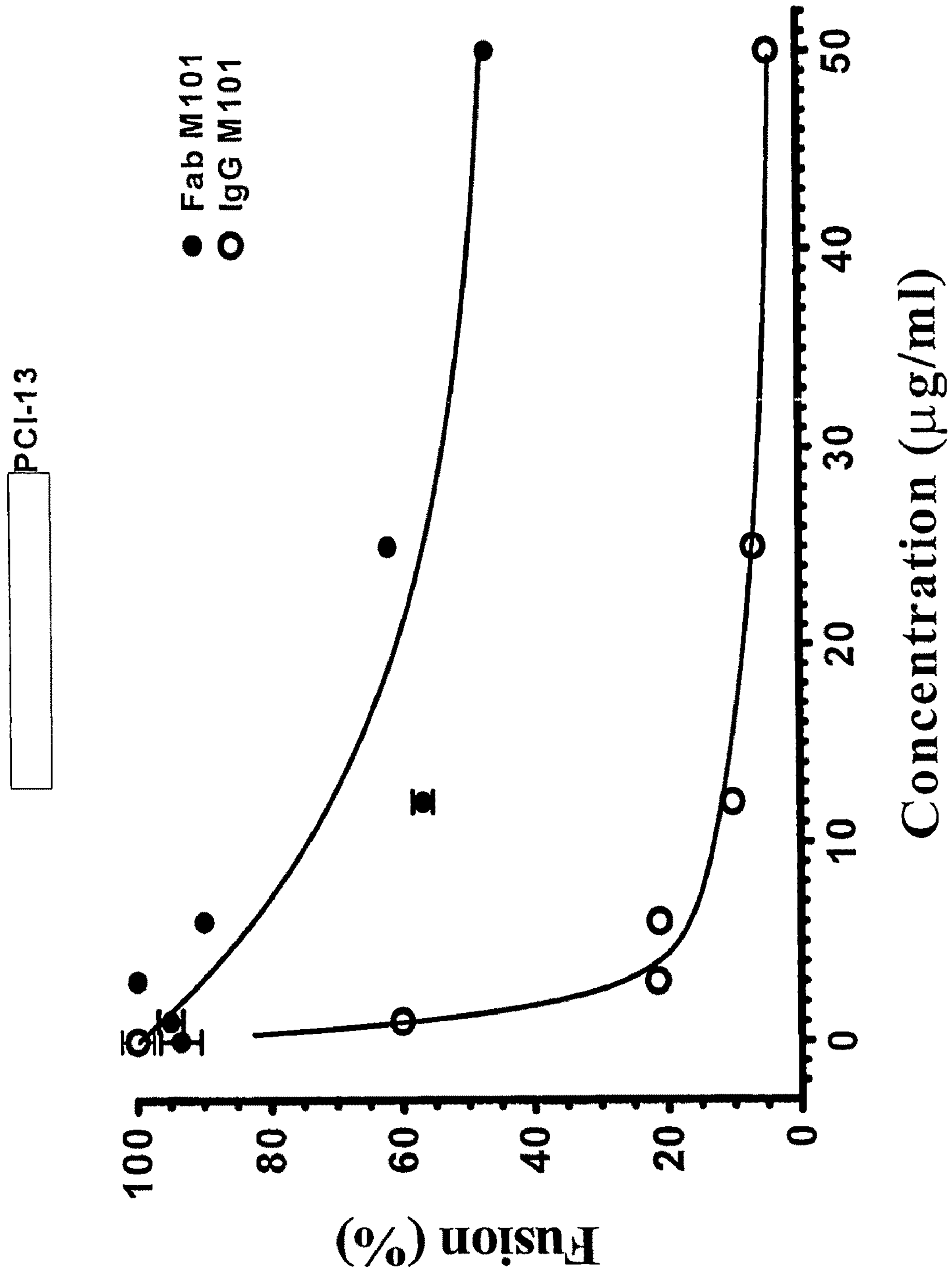
Figure 2:
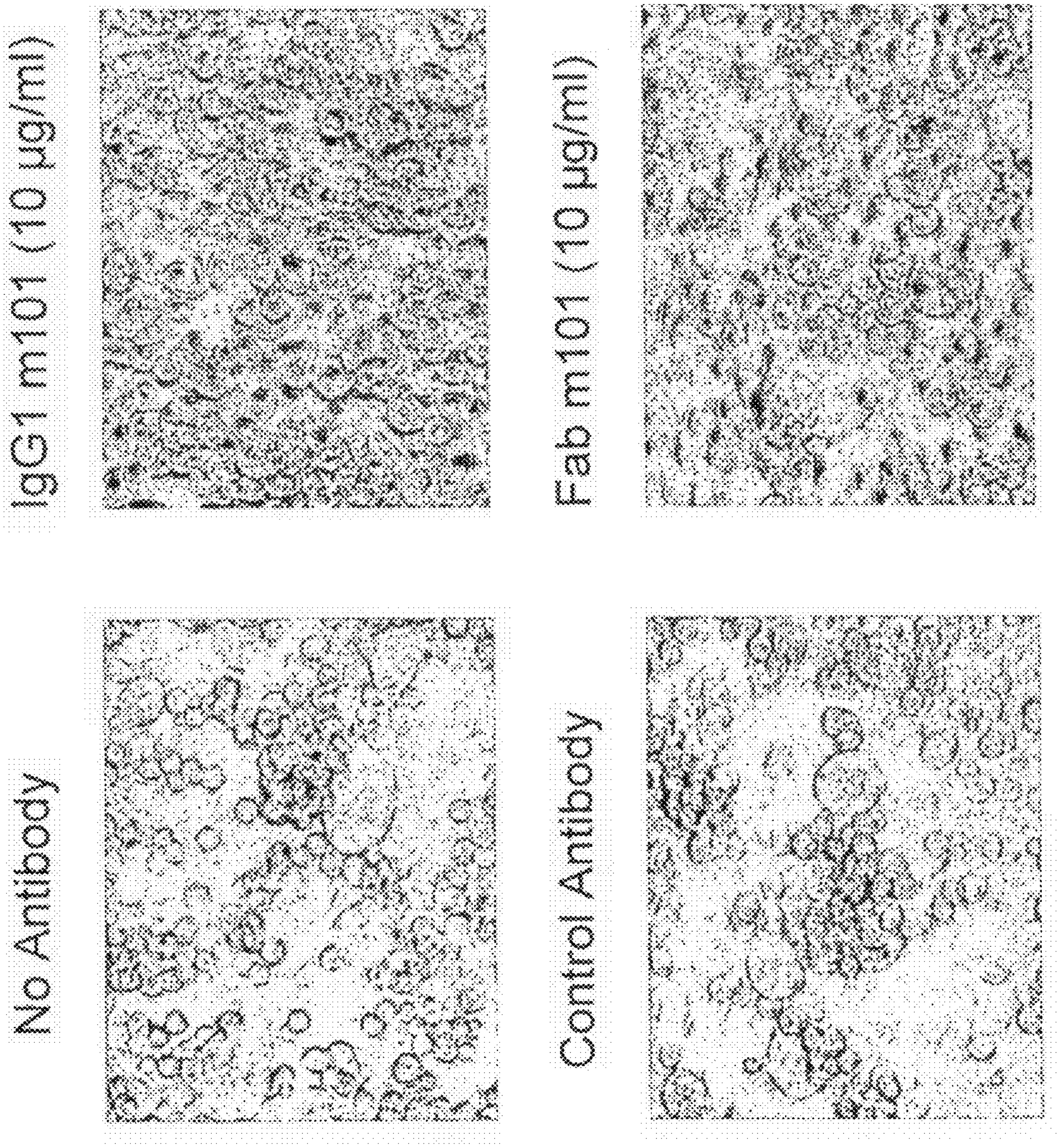
FIG. 2: Inhibition of HeV Env-mediated syncytia formation by m101. The effector cells, prepared as described in FIG. 1 legend were pre-incubated with IgG1 m101, Fab m101, or the control irrelevant antibody (X5 specific for HIV (Moulard, M. et al. 2002 *Proc Natl Acad Sci USA* 99:6913-6918)) for 20 min at room temperature, then $2\times10^5$ cells in 200 μl were overlaid on 80% confluent monolayers of PCI-13 cells plated in a 48-well plate, and incubated for 3 h at 37° C. in a humidified 5% $CO_2$ atmosphere. Photographs were taken using phase contrast microscope with a 10× objective. Shown are illustrative portions of the original photographs that are electronically amplified for clarity. The top and bottom pictures of the left panel show formation of syncytia in the absence of antibody or in the presence of a control antibody; there were 17 or 20 giant fused cells (syncytia) counted per complete photograph view, respectively. The top and bottom pictures of the right panel show complete inhibition of syncytia formation by IgG1 m101 or reduction in the number of syncytia by Fab m101 at 10 μg/ml, there were 0 or 9 syncytia per complete view, respectively.

Potent Inhibitory Activity of IgG1 m101 Against HeV Env-mediated Fusion and Live Virus In most cases, but not always, whole antibodies are better neutralizers than Fabs. Thus the most potent HeV-fusion inhibiting Fab, m101, was converted to a whole antibody format (IgG1) and tested in a cell fusion assay. The IgG1 m101 inhibitory activity was much higher than the activity of the Fab m101 (FIGS. 1 and 2). The conversion of Fab m101 to IgG1 dramatically decreased its IC50s. For HeLa-ATCC cells which exhibit lower fusion rates, the IC50 decreased from 4.2 μg/ml to 0.5 μg/ml (FIG. 1A). For the highly fusogenic PCI-13 cells, the IC50 decreased from 38 μg/ml to 1.2 μg/ml (FIG. 1B). In another experiment the IgG1 m101 inhibited 95% of fusion at 3 μg/ml. IgG1 m101 also potently inhibited syncytia formation in correlation with its inhibitory activity measured by the reporter gene assay. An example using the highly fusogenic PCI-13 cells is shown in FIG. 2. Here IgG1 m101 completely inhibited formation of syncytia at 10 μg/ml, whereas at the same concentration, Fab m101 inhibited approximately 50% of syncytia formation.

IgG1 m101 was also exceptionally potent in neutralizing infectious HeV. Complete (100%) neutralization was achieved at 12.5 μg/ml, more than 99% at 6 μg/ml, and 98% at 1.6 μg/ml (Table 4). These results demonstrated that IgG1 m101 is a very potent neutralizer of infectious HeV.

Mechanism of Virus Entry Inhibition by the Antibodies: Correlation with Binding to Native G To begin to elucidate the mechanisms of the inhibitory activity of the selected antibodies we measured their binding rate constants and affinities to sG in a Biacore assay. The antibodies bound with high (1 to $10^3$ nM range) affinity to sG as measured by Biacore (Table 5). The on rate constants varied significantly but there was no significant variation in the off rate constants except the very low dissociation rate constant of m102. The best inhibitors of HeV G-mediated fusion and infection, m101 and m102, exhibited the highest affinity. In this context there was correlation between binding to sG and fusion inhibition by groups of antibodies divided into good (m101 and m102) and poor (the rest) neutralizers although direct mathematically calculated correlation between the Biacore measured affinity of each antibody to sG and fusion inhibitory activity was not found.

Figure 3:
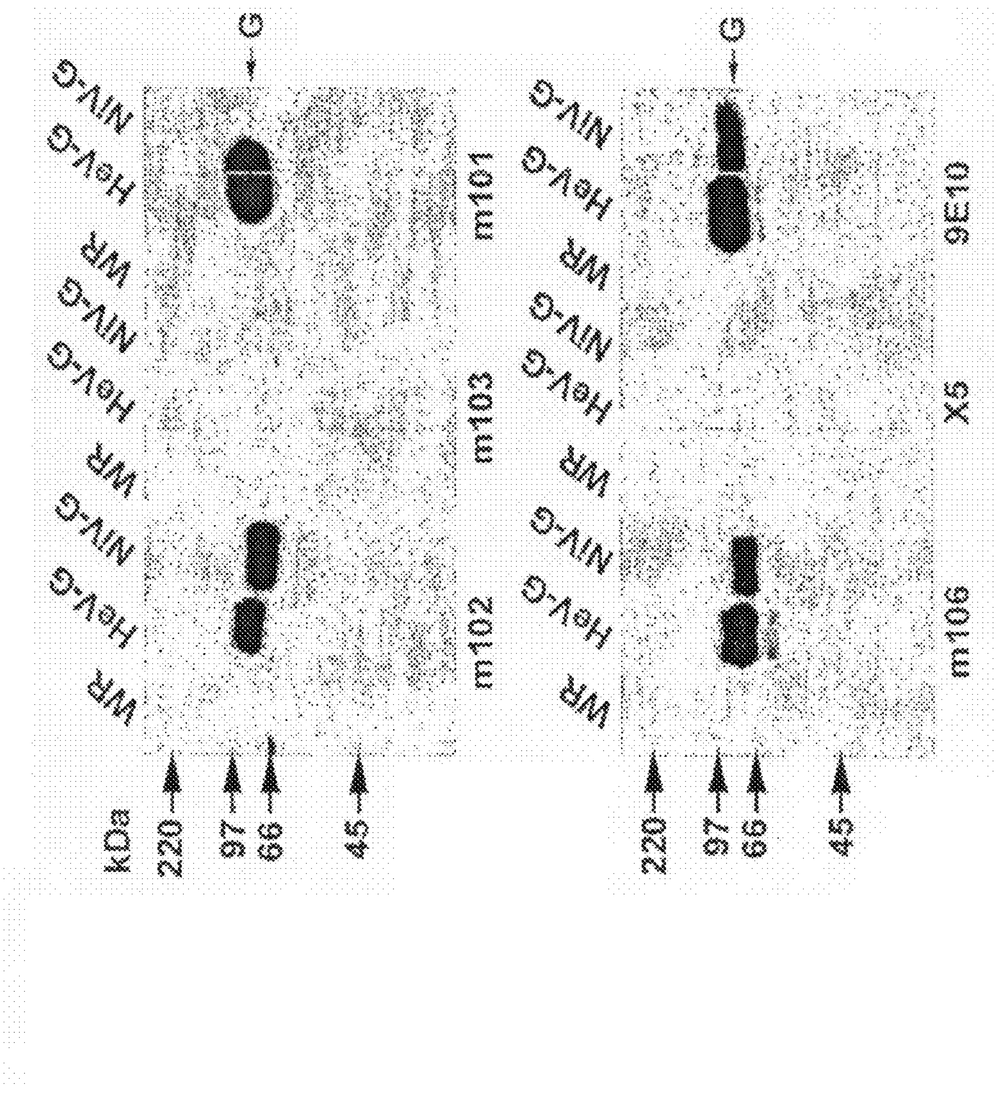
FIG. 3. Immunoprecipitation of HeV and NiV G glycoproteins by anti-G Fabs. HeLa cells were infected with WR, a control *vaccinia* virus, or recombinant *vaccinia* virus expressing myc-tagged HeV G or NiV G, and beginning at 6 h postinfection, labeled with $[^{35}S]$ methionine-cysteine at 37° C. overnight. Lysates were made in buffer containing Triton-X100 and incubated with various Fabs or mouse anti-myc 9E10 for at least 1 h at 4° C., then precipitated with Protein G Sepharose. Immunoprecipitated proteins were analyzed by 10% SDS-PAGE followed by autoradiography. WR denotes a control where the cells were infected with wild type *vaccinia* virus, X5 is a control antibody specific for gp120 of HIV, and 9E10 is an anti-c-Myc antibody serving as a positive control. Gels for m108 and m109 are also shown. The arrows next to G denote the position of the bands corresponding to the monomeric G.

To find other possible correlations between binding and inhibition we measured binding to native G which was immunoprecipitated from lysates of cells infected with recombinant *vaccinia* viruses. The extent of immunoprecipitation, which is proportional to the antibody binding affinity to native full-length G glycoprotein, was highest for m101 binding to HeV G (FIG. 3). Two of these antibodies, m102 and m106 demonstrated significant cross-reactivity to both HeV and NiV G (FIG. 3). The levels of immunoprecipitation correlated with cell fusion (Table 3) indicating that binding to native G is a better correlate of fusion inhibitory activity than binding to soluble G.

Outcompeting the Receptor Ephrin-B2 as a Mechanism of Virus Entry Inhibition by m101 and m102

To further define the mechanism of virus entry inhibition by the most potent neutralizer m101 we measured its competition with the recently identified receptor for Hendra and Nipah viruses, ephrin-B2 (Bonaparte M. I. et al. 2005 *Proc*

Figure 4:
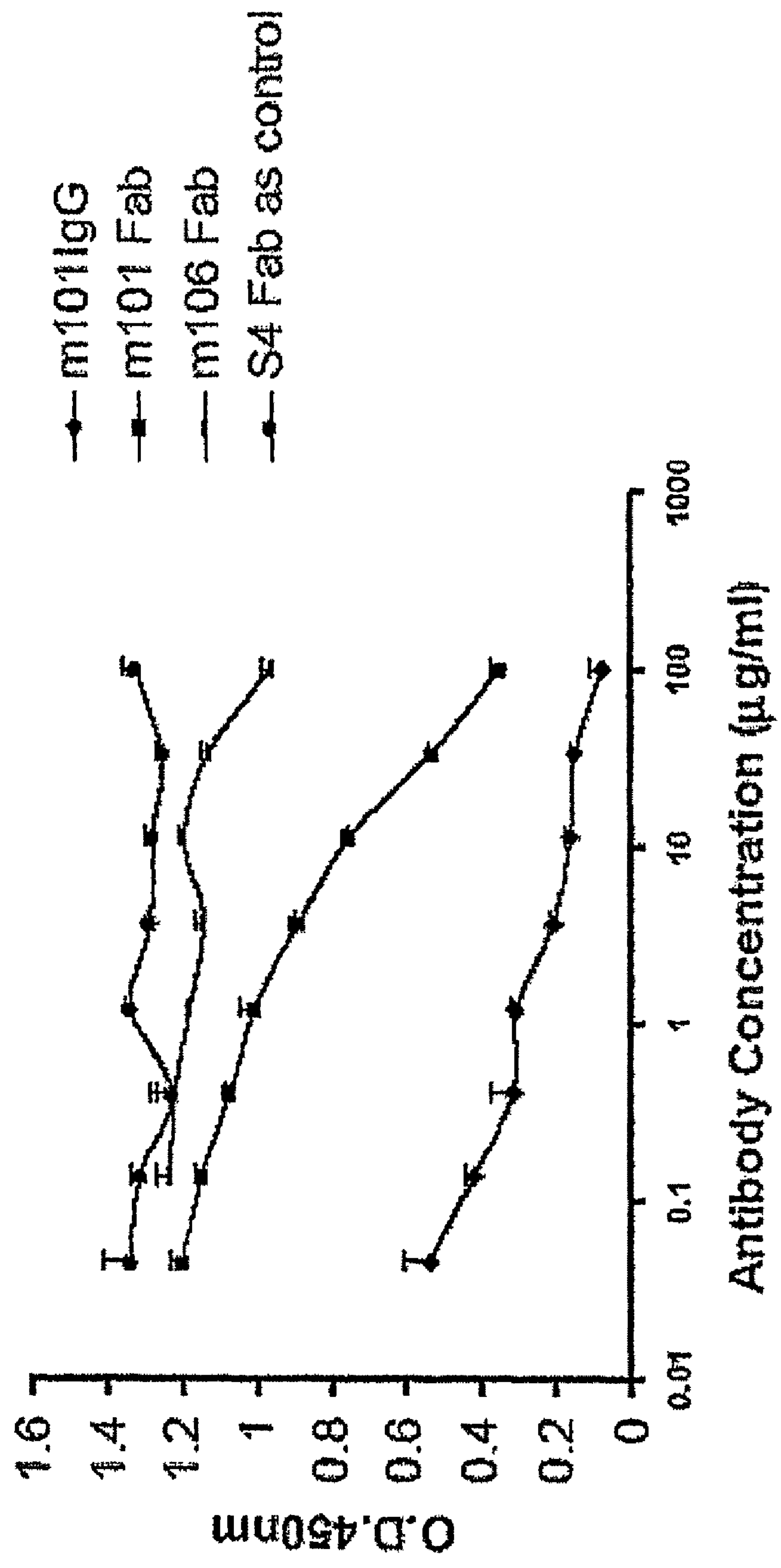
FIG. 4. Competition between anti-G antibodies and ephrin-B2 for binding to Hendra G. Serially diluted Fab m101, IgG1 m101 and Fab m106 were mixed with Hendra G, and added to the virus receptor ephrin-B2 coated on the bottom of a 96-well plate, and the amount of bound G measured as described in Example 1. An Fab specific for the SARS-CoV S protein was used as control.

*Natl Acad Sci USA* 102:10652-10657). M101 competed with ephrin-B2 for binding to sG; IgG m101 was a much better competitor than Fab m101 (FIG. 4), which correlates with their inhibitory activity and is likely due to the multivalent nature of their interaction. Similar results were obtained with m102 and by using Biacore (supplemental FIG. 2 in Bonaparte M. I. et al. 2005 *Proc Natl Acad Sci USA* 102: 10652-10657). These data indicate that m101 and m102 inhibit entry of Hendra virus and likely Nipah virus by preventing the access of these viruses to their receptor. They also indicate that the epitopes of m101 and m102 overlap with the receptor binding site on G. Interestingly, m106 competed with ephrin-B2 much weaker than m101 and only at very high concentrations (FIG. 4).

Further Characterization of the Epitopes of the Selected Anti-G Antibodies

To further characterize the epitopes of the newly identified antibodies we measured the competition of m101, m102, m103, m106 and m107 with one another by ELISA (presently, there are no anti-Hendra G antibodies with known epitopes). The m101, m102, and m103 antibodies competed with each other indicating that they bind to overlapping epitopes that are distinct from the epitopes of m106 and m107. Interestingly, m103 appears to synergize with m106 leading to increased binding of one in the presence of the other. These results indicate that m101-3 may neutralize the virus by a different mechanism from m106 and m107 but further studies with ephrin competition are needed to definitely elucidate the mechanism of their neutralizing activity.

Figure 5:
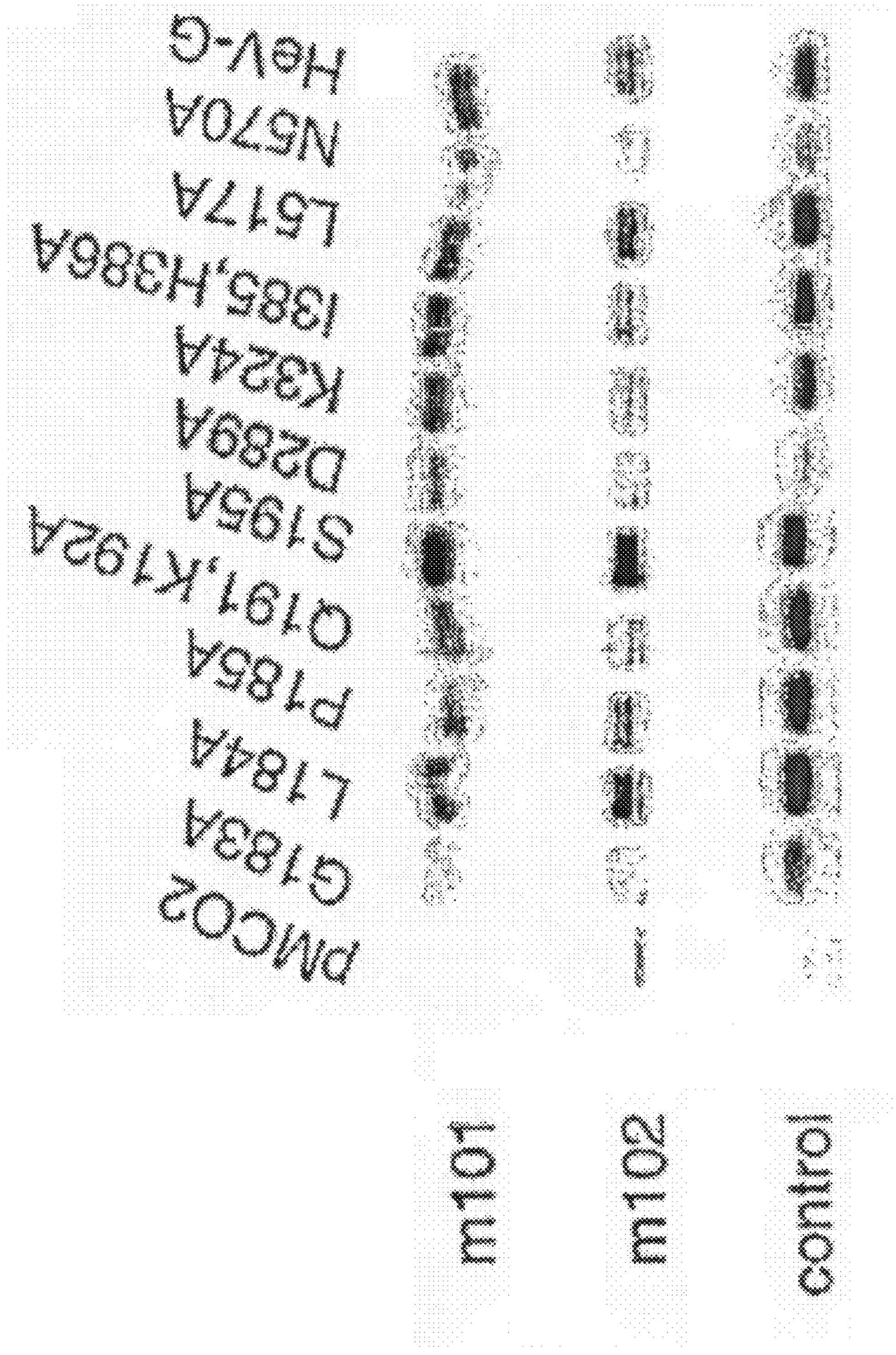
FIG. 5. Binding of m101 and m102 to alanine mutants of HeV G. HeLa cells transfected with wild type HeV G, various alanine mutants of HeV G, or pMC02 (empty vector) were infected with WR *vaccinia* virus to drive expression, radio-labeled with $[^{35}]$S methionine-cysteine overnight, lysed in buffer containing Triton X-100, and subjected to immunoprecipitation by m101, m102, or rabbit polyclonal G antisera. Lysates were then precipitated with Protein G Sepharose and analyzed by 10% SDS-PAGE followed by autoradiography.
Figure 6:
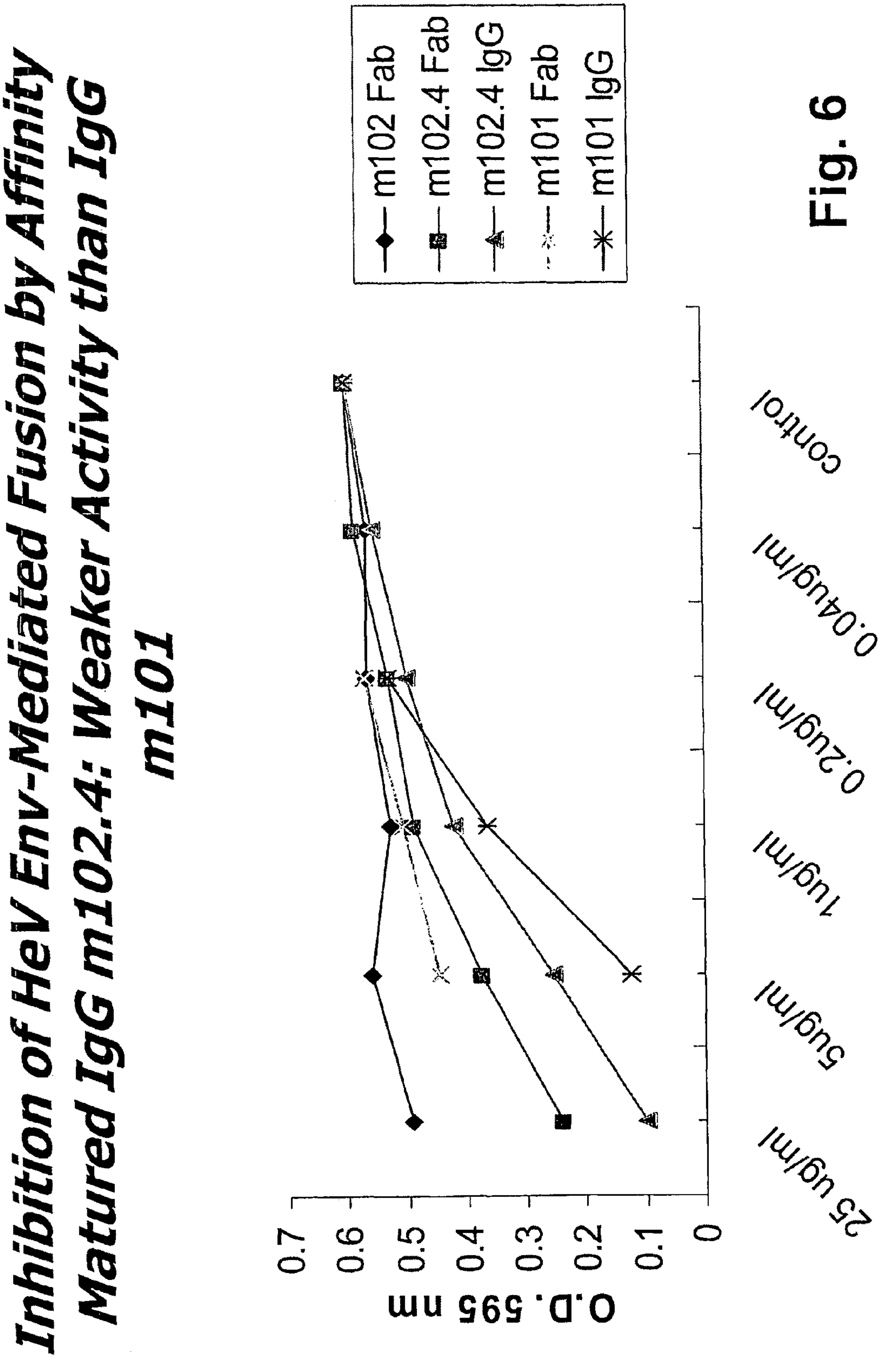
FIG. 6. Comparison of the inhibitory activity of m101, m102.4 Fab and IgG1, and m102 Fab in HeV Env-mediated cell fusion. HeLa-USU cells were infected with *vaccinia* recombinants encoding HeV F and G glycoproteins, and with a *vaccinia* recombinant encoding T7 RNA polymerase (effecter cells). Target cell U373 was infected with the *E. coli* LacZ-encoding reporter *vaccinia* virus vCB21R. Serial diluted antibodies were pre-incubated with effecter cells for 0.5 hr and then mixed with target cells. The cell fusion assay was performed for 2.5 hr at 37° C. Fusion was measured as described in Example 1. Antibodies concentrations were plotted against Beta-Gal assay reading at 595 nm.
Figure 7:
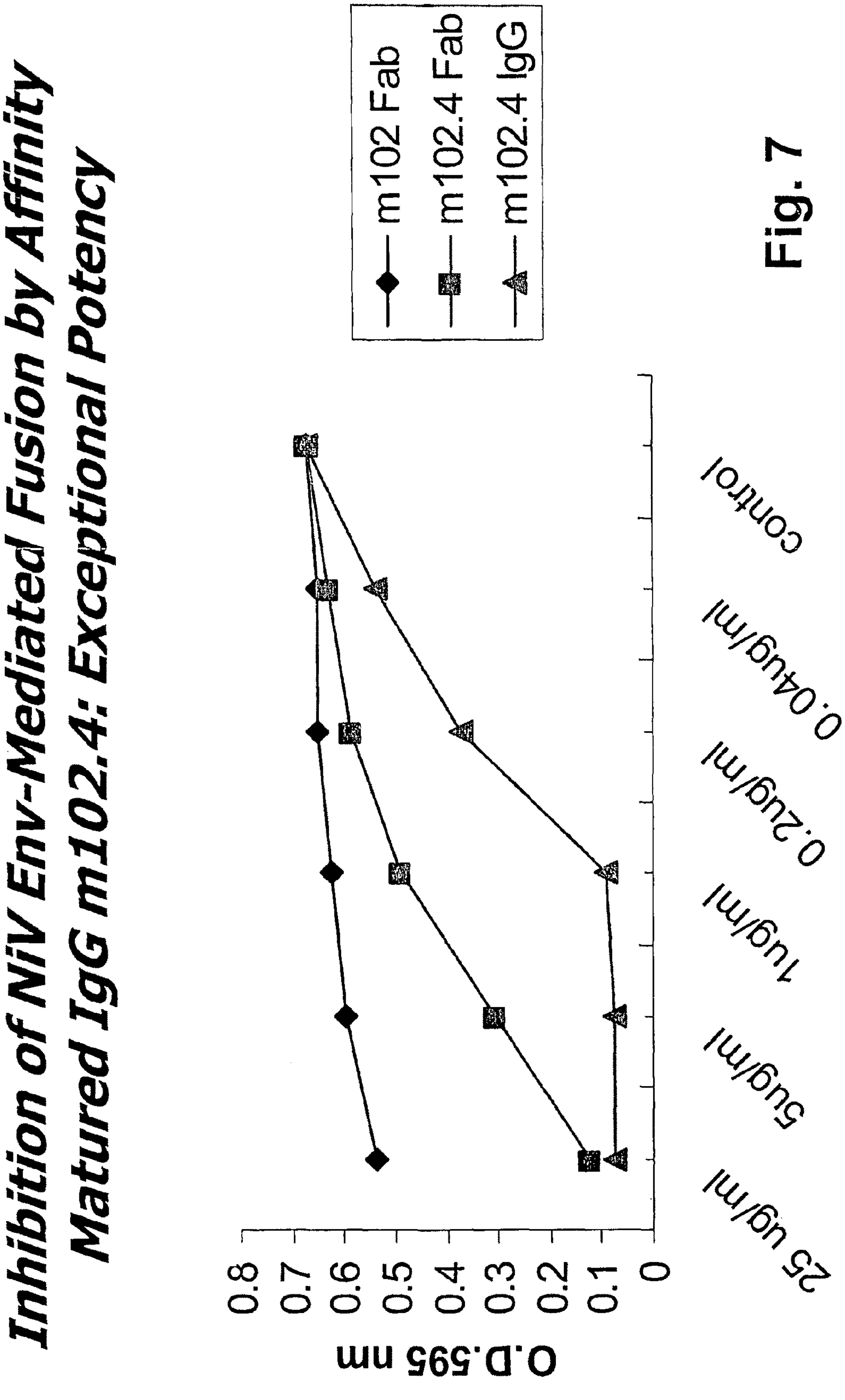
FIG. 7. Significantly higher inhibitory activity of m102.4 Fab and IgG1 than m102 Fab in NiV-Env-mediated cell fusion. HeLa-USU cells were infected with *vaccinia* recombinants encoding NiV F and G glycoproteins, and with a *vaccinia* recombinant encoding T7 RNA polymerase (effecter cells). Target cell U373 was infected with the *E. coli* LacZ-encoding reporter *vaccinia* virus vCB21R. Antibodies were pre-incubated with effecter cells for 0.5 hr and then mixed with target cells. The cell fusion assay was performed for 2.5 hr at 37° C. Fusion was measured as described in Example 1. Antibodies concentrations were plotted against Beta-Gal assay reading at 595 nm.

In an initial attempt to localize the epitopes of m101 and m102 we measured their binding to a panel of 10 G alanine scanning mutants, selected to represent different portions of the protein: G183A, L184A, P185A, (Q191, K192A), S195A, D289A, K324A, (I385, H386A), L517A, N570A, where the two double mutants are in parentheses. Of these mutants only one, G183A, decreases binding of both m101 and m102 to G; this mutant bound strongly to anti-G rabbit polyclonal antibodies and to the receptor ephrin-B2. (FIG. 5). The G183 residue is localized at the base of the globular head of the G protein according to a model structure (Yu M. et al. 1998 *Virology* 251:227-233), and could be a part of the antibody epitope that does not overlap with the receptor binding site on G. Another residue, N570, appears to decrease binding of m102 to G but not the binding of m101 and the receptor (FIG. 5). This residue could be a part of the m102 epitope that does not overlap with the epitope of m101 and the receptor binding site on G.

TABLE 1

Selection of phage clones with unique sequences that exhibit significant binding to sG

| Fab | H3 Sequence | $A_{450}$ |
|---|---|---|
| m101 | D P G G Y S Y G P Y Y Y Y Y G M D V | 1.0 |
| m102 | G W G R E Q L A P H P S Q Y Y Y Y Y Y G M D V | 1.4 |
| m103 | D S R Y H D A F D I | 0.8 |
| m104 | E S S W L D A F D I | 0.7 |
| m105 | V G G I T G T A D A F D I | 0.9 |
| m106 | D Q L A G Y Y Y D S S G Y H Y Y Y Y G M D V | 1.6 |
| m107 | D H V H G P D A F D I | 0.6 |
| m108 | V G G A F D I | 0.5 |
| m109 | G W F R D W Y F D L | 0.0 |
| m110 | E G L P E T D D A F D I | 0.0 |
| m111 | E G A D Y | 0.0 |
| m112 | D G A D Y | 0.4 |
| m113 | Y K L Q S D A F D I | 0.1 |
| m114 | A G P V G A T T G T F D Y | 0.0 |
| m115 | G S Q S Y D H Y Y Y Y | 0.4 |

TABLE 1-continued

Selection of phage clones with unique sequences that exhibit significant binding to sG

| Fab | H3 Sequence | $A_{450}$ |
|---|---|---|
| m116 | D S A G L G A | 0.3 |
| m117 | R E S G P E F F Q H | 0.0 |

Screening of 380 individual phage clones was performed in phage ELISA with sG as described in Example 1. The sequences of the HC CDR3s (H3s) of phage-displayed Fabs that exhibited significant binding to sG in phage ELISA are shown as identified according to the IMGT database (http://imgt.cines.fr). Soluble Fabs were expressed, purified, and tested in ELISA for binding to sG. The solution absorbance at 450 nm ($A_{450}$) is shown as a measure of the strength of binding.

TABLE 2

V-gene families and number of amino acids changed compared to the germ line

| Antibody | VH family | VL family | VH changes | VL changes |
|---|---|---|---|---|
| m101 | VH1 | Vk1 | 2 | 6 |
| m102 | VH1 | Vk3 | 5 | 8 |
| m103 | VH3 | Vk2 | 0 | 0 |
| m104 | VH1 | Vk2 | 0 | 13 |
| m105 | VH3 | Vk1 | 0 | 0 |
| m106 | VH1 | Vk1 | 0 | 0 |
| m107 | VH1 | Vλ1 | 1 | 3 |

Shown are the gene families for the $V_H$ genes, which are IgM specific, and for the $V_L$ genes, which are from all Ig classes, and their variations compared to germline sequences.

TABLE 3

Inhibition of HeV Env-mediated cell fusion by the selected Fabs

| Fab | HeV | NiV |
|---|---|---|
| m101 | +++ | + |
| m102 | ++ | ++ |
| m103 | + | 0 |
| m104 | + | + |
| m105 | 0 | + |
| m106 | + | ++ |
| m107 | 0 | + |
| m108-17 | 0 | 0 |
| X5 | 0 | 0 |

Anti-HeV G Fabs were used for inhibition of fusion as described in Example 1. A summary of four different experiments are shown where each + is a measure of increased inhibitory activity, and 0 means no measurable fusion activity compared to the background. Fab X5 is a control antibody specific for the HIV-1 gp120 (Moulard, M. et al. 2002 Proc Natl Acad Sci USA 99: 6913-6918).

TABLE 4

Neutralization of infectious HeV by IgG1 m101

| Antibody concentration (μg/ml) | Number of foci per well in each replica | | | | Average number of foci (% neutralization) |
|---|---|---|---|---|---|
| 25 | 0 | 0 | 0 | 0 | 0 (100) |
| 12.5 | 0 | 0 | 0 | 0 | 0 (100) |
| 6.2 | 0 | 0 | 1 | 0 | 0.25 (99) |
| 3.1 | 1 | 0 | 1 | 0 | 0.5 (98) |
| 1.6 | 1 | 1 | 0 | 0 | 0.5 (98) |
| 0.8 | 5 | 2 | 2 | 2 | 2.75 (91) |
| 0 | 30 | 37 | 34 | 30 | 33 (0) |

IgG1 m101 was incubated with infectious HeV and the mixture added to plated Vero cells. After the 30 minute incubation, antibody-virus mixtures were removed, cells were washed and fresh EMEM-10 containing fresh antibody was added to the cells and incubated overnight. The average number of foci in the absence of antibody was 33. The percentage of neutralization shown below in parentheses was calculated by subtracting the number of foci in the wells with antibodies from the number of foci without antibodies and dividing the resulting number by the number of foci without antibodies, and multiplying by 100.

TABLE 5

Binding rate constants and affinities of selected Fabs

| Antibody | $k_a$ ($\times 10^4$) $M^{-1} s^{-1}$ | $k_d$ ($\times 10^{-3}$) $s^{-1}$ | $K_d$, nM |
|---|---|---|---|
| m101 | 13 | 3.5 | 28 |
| m102 | 5.7 | 0.068 | 1.2 |
| m103 | * | * | 1800 |
| m104 | 0.3 | 1.6 | 600 |
| m105 | 7.4 | 5.1 | 69 |
| m106 | 6.2 | 3.3 | 54 |
| m107 | 30 | 2.2 | 78 |

Interaction between various Fabs and sG was analyzed at 25° C. by surface plasmon resonance technology. Fabs at different concentrations were injected at flow rate of 30 μl/min, and the association and dissociation phase data were fitted simultaneously to a 1:1 Langmuir global model by using the nonlinear data analysis program BIAevaluation 3.2. Individual association rate constant, $k_a$, dissociation rate constant, $k_d$, and equilibrium dissociation constant, $K_d$, were obtained from at least three separate experiments. The standard deviation was on average about 20%.
* denotes that only steady state affinity was calculated due to fast kinetics.

Discussion

The major finding of this study is the identification of an antibody, m101, with exceptional potency against infectious HeV. Six other antibodies were also identified that are specific for HeV G and two of them significantly cross-reacted with NiV G. To our knowledge these antibodies are the first human monoclonal antibodies (hmAbs) identified against HeV and NiV. Interestingly, the only monoclonal antibody, Synagis (Pollack, P. and Groothuis, J. R. 2002 *J Infect Chemother* 8:201-206) (palivizumab, MEDI-493), approved by FDA for clinical use against a viral disease (Dimitrov, D. S. 2004 *Nat Rev Microbiol* 2:109-122), is also specific for a paramyxovirus, respiratory syncytial virus (RSV); it is a humanized version of a mouse antibody and is used for prevention of RSV infections in neonates and immune-compromised individuals. Synagis inhibits virus entry and cell fusion in vitro very potently, it appears that its efficacy in vivo is correlated to its potency in vitro, and it was proposed that its fusion-inhibiting activity could be a major determinant of its potency in vivo (Johnson, S. et al. 1999 *Infect Dis* 180:35-40). Because RSV and henipaviruses enter cells by the same pathway, fusion at the cell surface and not through endocytosis as most other enveloped viruses do (Dimitrov, D. S. 2004 *Nat Rev Microbiol* 2:109-122), and are members of the same virus family, one predicts that m101 might be equally if not more effective against HeV as palivizumab is against RSV.

Each of the newly identified Fabs were examined in HeV and NiV-mediated cell fusion assays to evaluate their potential in blocking binding and/or the subsequent membrane fusion process. The Fab m101 demonstrated the most potent cell-fusion inhibitory activity, and m102 exhibited cross-reactive activity against both HeV and NiV. The mechanism by which m101 and m-102 inhibit HeV fusion and infection is by blocking the interaction of G with ephrin-B2, which we recently identified as a functional receptor for HeV and NiV (Bonaparte et al. 2005 *Proc Natl Acad Sci USA* 102:10652-10657) (the receptor function of ephrin-B2 for NiV was also independently identified by using a different approach (Negrete O. A. et al. 2005 *Nature* 436:401-405)). However, an alternative possibility is that these antibodies bind to G and can also prevent its required interaction with the F glycoprotein to trigger the fusion process. There was a general correlation between their inhibitory activity and binding affinity of the Fabs to the G glycoprotein especially to the native membrane-associated protein as measured by immunoprecipitation.

Conversion of Fab m101 to IgG1 led to potent neutralization of infectious HeV where it neutralized more than 90% at concentration less than 1 μg/ml. One could speculate that this may be due to increased stability and avidity of the antibody and/or its ability to cross-link the oligomeric G glycoprotein on the surfaces of virus and infected cells. Nonetheless, the extreme potency of IgG1 m101 in infectious HeV neutralization assays suggests that it may be important to convert other Fabs to IgG1 for evaluation as potent neutralizing hmAbs.

There is considerable amino acid homology between the F and G Envs of HeV and NiV (Harcourt, B. H. et al. 2000 *Virology* 271:334-349; Wang, L. et al. 2001 *Microbes Infect* 3:279-287). Previous studies have demonstrated that HeV and NiV antisera do cross neutralize, with each serum being slightly less effective against the heterotypic virus (Crameri, G. et al. 2002 *J Virol Methods* 99:41-51; Tarnin, A. 2002 *Virology* 296:190-200). Further, the HeV and NiV glycoproteins can functionally complement one another in mediating membrane fusion with wild-type efficiency (Bossart, K. N. and Broder, C. C. 2004 *Methods Mol Biol* 269:309-332; Bossart, K. N. et al. 2002 *J Virol* 76:11186-11198). Thus, we anticipated that if antibodies were identified using sG from HeV some should display cross-reactive binding to shared epitopes between HeV and NiV. Indeed, two of the seven Fabs were capable of reacting equally well in immunoprecipitation of recombinant membrane-associated HeV and NiV G. In addition, m102 was capable of inhibiting HeV and NiV-mediated fusion and may reflect a conserved epitope between these viruses that could be important not only for neutralization but also for the entry mechanism. Upon conversion to an IgG1, m102 might be capable of potently neutralizing both HeV and NiV.

Antibody binding competition assays revealed that the panel of Fabs developed here, comprise two distinct groups and Fabs within each group possess overlapping epitopes. Analysis of the anti-G Fabs by Western-blotting revealed no reactivity to G, indicating that the epitopes recognized by these Fabs are likely conformation dependent. The most potent neutralizers, m101 and m102, bound to most of the alanine mutants tested except one which appears to be located at the base of the globular head of G according to a model of its structure (Yu M. et al. 1998 *Virology* 251:227-233). Further studies are needed to precisely localize their epitopes.

Taken together, our results demonstrate new immunotherapeutics against HeV and NiV. These human antibodies are also expected to be useful for diagnosis, as research reagents and serving as the basis for vaccines.

EXAMPLE 1

Cells and Culture Conditions

HeLa-USU cells were provided by Anthony Maurelli, Uniformed Services University (USU). HeLa-ATCC was obtained from the American Tissue Culture Collection (ATCC #CCL 2). Vero cells were provided by Alison O'Brien, USU. The human glioblastoma cell line U373-MG was provided by Adam P. Geballe, Fred Hutchinson Cancer Research Center (Harrington R. D. 1993 *J Virol* 67:5939-5947). The Human head and neck carcinoma PCI 13 cell line was the gift of Ernest Smith, Vaccinex, Inc. HeLa-USU, HeLa-ATCC, and U373 cells were maintained in Dulbecco's modified Eagle's medium (Quality Biologicals, Gaithersburg, Md.) supplemented with 10% cosmic calf serum (CCS) (HyClone, Logan, Utah), and 2 mM L-glutamine (DMEM-10). PCI 13 cells were maintained in DMEM-10 supplemented with 1 mM HEPES (Quality Bio.). Vero cells were maintained in Eagle's minimal essential medium (EMEM) (Quality Bio.) supplemented with 10% cosmic calf serum (CCS) (HyClone), and 2 mM L-glutamine (FMEM-10). All cell cultures were maintained at 37° C. in a humidified 5% CO2 atmosphere.

Alanine G Mutants

Alanine mutations were made at specific residues in myc-tagged HeV G using site-directed mutagenesis (Stratagene). All mutants were sequenced and tested for expression. Plasmids containing either mutant or wild type HeV Gmyc were transfected into HeLa USU monolayers using Fugene (Roche), and incubated overnight. The immunoprecipitation of the mutant G was performed as described below in the section Immunoprecipitation except that 3.0 μg of either m101 or m102 or 5 μL of rabbit polyclonal α-sHeV G sera was incubated with 80 μL lysates overnight at 4° C., followed by precipitation at room temperature with 100 μL 20% Protein G-Sepharose for 45 minutes.

Selection of G-specific Phage-displayed Fabs

A naïve human Fab phage display library (a total of about $10^{10}$ members), constructed from peripheral blood B cells of 10 healthy donors, was used for selection of Fabs against purified, soluble and oligomeric HeV G glycoprotein (sG) (Bossart, K. N. et al. 2005 *J Virol* 79:6690-6702), conjugated to magnetic beads (Dynabeads M-270 Epoxy, DYNAL Inc., New Hyde Park, N.Y.). Amplified libraries of $10^{12}$ phage-displayed Fabs were incubated with 5, 3, 3 and 1 μg of sG in 500 μl volume for 2 hours at room temperature during the 1st, 2nd, 3rd and 4th rounds of biopanning, respectively. After each round of incubation the beads were washed 5 times for the first round and 15 times for the later rounds with PBST (PBS containing 0.05% Tween-20) to remove non-specifically bound phage, the bead-bound phage were mixed with TG1 cells for one hour at 37° C., the phage was amplified from the infected cells and used in the next round of biopanning. After the 4th round of biopanning 380 clones were randomly picked from the infected TG1 cells and each inoculated into 150 μl 2YT medium containing 100 μg/ml carbenicillin and 0.2% glucose in 96-well plates by using the automated BioRobotics BioPick colony picking system (Genomic Solutions, Ann Arbor, Mich.). After the bacterial cultures reached optical density (OD) 0.5 at 600 μm, helper phage M13K07 at 10 M.O.I. and kanamycin at 50 μg/ml final concentration were added to the medium, and the plates were further incubated at 30° C. overnight in a shaker at 250 rpm. The phage supernatants were mixed with 3% nonfat milk in PBS at a 4:1 volume ratio and used for ELISA to identify clones of phage displaying Fabs with high sG-binding affinity. The supernatants were incubated for 2 hours at room temperature with sG protein coated at 50 ng per well in 96-well plates and washed 5 times with PBST. (sG was coated in 50 μl coating buffer (50 mM $NaHCO_3$ pH 9.6); after overnight incubation at 40° C. it was blocked with 3% nonfat milk in PBS and washed 3 times with PBS containing 0.05% Tween-20). Soluble G-bound phage were detected by using horseradish-peroxidase-conjugated goat anti-M13 antibody. After incubation with the antibody, the non-specifically bound antibody was washed, the TMB substrate was added and the solution absorbance at 450 nm ($A_{450}$) was measured. Clones that bound to sG with $A_{450}$>1.0 were selected for further characterization.

Expression and Purification of Selected Soluble Fabs

The $V_H$ and $V_L$ of the selected clones were sequenced, and the Fabs encoded by clones with unique sequences were expressed and purified as described below. Plasmids extracted from these clones were used for transformation of HB2151 cells. A single colony was picked from the plate containing freshly transformed cells, inoculated into 200 ml 2YT medium containing 100 μg/ml ampicillin and 0.2% glucose, and incubated at 37° C. with shaking at 250 rpm. When the culture OD at 600 nm reached 0.90, IPTG at 0.5 mM final concentration was added, and the culture was further incubated overnight at 30° C. Bacterial pellet was collected after centrifugation at 8000 g for 20 minutes and resuspended in PBS buffer containing 0.5 mU Polymixin B (Sigma-Aldrich, St. Louis, Mo.). After 30 min incubation with rotation at 50 rpm at room temperature, it was centrifuged at 25000 g for 25 min at 4° C., and the supernatant used for Fab purification with protein G column (Sigma-Aldrich, St. Louis, Mo.).

Conversion of Fab to IgG1, and IgG1 Expression and Purification

The Fab heavy and light chain were amplified and recloned in the PDR12 vector (provided by D. Burton, the Scripps Research Institute, La Jolla, Calif.) for whole IgG1 expression. The resulting construct was transfected and the IgG1 expressed using the FreeStyle™ 293 Expression Kit following the protocol from the manufacturer (Invitrogen, Carlsbad, Calif.). The IgG1 was purified from the culture medium with protein G column (Sigma-Aldrich, St. Louis, Mo.).

Affinity Determination by Surface Plasmon Resonance

Interactions between various Fabs and G were analyzed by surface plasmon resonance technology using a BIACORE 1000 instrument (Biacore, Pharmacia, Piscataway, N.J.). sG was covalently immobilized onto a sensor chip (CM5) using carbodiimide coupling chemistry. A control reference surface was prepared for nonspecific binding and refractive index changes. For analysis of the kinetics of interactions, varying concentrations of Fabs (300, 100, 33, 11, and 3.7 nM) were injected at flow rate of 30 μl/min using running buffer containing 150 mM NaCl, 3 mM EDTA, and 0.005% P-20 (pH 7.4). The association and dissociation phase data were fitted simultaneously to a 1:1 Langmuir global model by using the nonlinear data analysis program BIAevaluation 3.2. All the experiments were performed at 25° C.

Competition ELISA

The Fabs m101, m102, m103, m106 and m107 were coated at 150, 50, 300, 300 and 100 ng per well, respectively in 50 μl coating buffer as described above for sG, blocked with nonfat milk and washed. C-Myc tagged sG mixed with each of the Fabs in blocking buffer at final concentration 5 μg/ml and 20 μg/ml, respectively, were added to each of the Fab coated wells; sG (5 μg/ml) without antibody was added to each of the coated Fabs as a positive control. Bound c-myc tagged sG protein was detected by an HRP conjugated anti-c-Myc antibody (Roche Diagnostics Corporation, Indianapolis, Ind.); the TMB substrate (Sigma-Aldrich, St. Louis, Mo.) was added and A450 measured.

Immunoprecipitation

HeLa-USU monolayers were infected with wild-type *vaccinia* (WR) or recombinant *vaccinia* expressing myc-tagged HeV G or NiV G at an MOI of 10 for 6 hours, then washed twice, and incubated overnight in methionine and cysteine-free essential medium plus 2.5% dialyzed fetal calf serum (Invitrogen) and 100 μCi of [$^{35}$S] ProMix/ml (Amersham Pharmacia Biotech, Piscataway, N.J.). Cells were lysed in 100 mM Tris-HCl (pH 8.0), 100 mM NaCl, and 1% Triton X-100. Lysates were incubated with each Fab at a concentration of 1 ug per 100 ul of lysate for at least one hour at 4° C., followed by precipitation at room temperature with 100 ul 20% Protein G-Sepharose (Amersham) for 45 minutes. Anti-myc antibody 9E10 (Roche Molecular Biochemicals) was used at a concentration of 2 ug per 100 ul of lysate. Samples were washed twice with lysis buffer followed by one wash with DOC buffer containing 100 mM Tris-HCl (pH 8.0), 100 mM NaCl, 0.1% sodium deoxycholate, and 0.1% SDS.

Samples were boiled in SDS-Polyacrylamide gel electrophoresis (SDS-PAGE) sample buffer with 2-mercaptoethanol and analyzed by SDS-PAGE and autoradiography.

Cell-fusion Assays

Fusion between HeV and NiV F and G envelope glycoprotein-expressing (effector cells) and target cells was measured by two assays: first, a reporter gene assay in which the cytoplasm of one cell population contained *vaccinia* virus-encoded T7 RNA polymerase and the cytoplasm of the other contained the *E. coli* lacZ gene linked to the T7 promoter; β-galactosidase (β-Gal) is synthesized only in fused cells (Bossart, K. N. and Broder, C. C. 2004 *Methods Mol Biol* 269:309-332; Nussbaum, O. et al. 1994 *J Virol* 68:5411-5422), and second, a syncitia assay. Typically, the expression of HeV and NiV F and G is performed in a HeV and NiV fusion and infection negative HeLa cell line derivative (HeLa-USU). Cytogenetic analysis has confirmed that the HeLa-USU cell line resistant to NiV and HeV mediated membrane fusion and live virus infection is derived from the ATCC (CCL-2) HeLa cell line. *vaccinia* virus-encoded proteins (Bossart, K. N. et al. 2001 *Virology* 290:121-135) were produced by infecting cells at a MOI of 10 and incubating infected cells at 31° C. overnight. Cell-fusion reactions were conducted with the various cell mixtures in 96-well plates at 37° C. Typically, the ratio of envelope glycoprotein-expressing cells to target cells was 1:1 ($2\times10^5$ total cells per well, 0.2-ml total volume). Cytosine arabinoside (40 μg/ml) was added to the fusion reaction mixture to reduce nonspecific β-Gal production. For quantitative analyses, Nonidet P-40 was added (0.5% final) at 2.5 h and aliquots of the lysates were assayed for β-Gal at ambient temperature with the substrate chlorophenol red-D-galactopyranoside (CPRG; Roche Diagnostics Corp., Indianapolis, Ind.). For inhibition by antibodies, serial antibody dilutions were made and added to effector cell populations 30 min prior to the addition of target cell populations. All assays were performed in duplicate and fusion data were calculated and expressed as rates of P-Gal activity (change in OD at 570 nm per minute×1,000) (Nussbaum, O. et al. 1994 *J Virol* 68:5411-5422). They were normalized with respect to cell fusion in the absence of antibodies, and plotted as function of the antibody concentration.

The syncytia assay was performed in 48-well plates. Target PCI-13 cells were plated to reach 80% confluency at the time of the experiment. Effector cells, HeLa USU, which are non-permissive to HeV Env and NiV Env mediated fusion, were infected with recombinant *vaccinia* virus to express HeV G and F proteins. Three wells of a six-well plate 80% confluent HeLa-USU were incubated with both recombinant *vaccinia* viruses, encoding HeV G and HeV F, MOI of 10 for each virus at 37° C. for 3 h in DMEM-10 containing 2.5% cosmic calf serum, 1 ml per well, then washed once and dissociated from the plates by using 0.5 ml per well enzyme-free PBS-based cell dissociation buffer (Invitrogen Corp., Carlsbad, Calif.). The cells were gathered into 50 ml sterile centrifuge tube (Corning Inc., Corning, N.Y.) and 20 ml DMEM-10 was added. The suspension was incubated 16 hours at 31° C. in a humidified 5% $CO_2$ atmosphere. Before the experiment, the cells were centrifuged at 1200 rpm for 5 min and the pellet was re-suspended in DMEM-10. The cells were counted, centrifuged again and re-suspended at a concentration of $2\times10^6$ cells/ml. Cytosine arabinoside was added to a concentration of 80 μg/ml. One-hundred-microliters of this cell suspension was mixed with the same amount DMEM-10 containing the antibody and incubated for 20 min at room temperature. The mixtures were added to the freshly washed (with DMEM-10) PCI-13 target cells in the 48-well plate and incubated for 3 h at 37° C. in a humidified 5% $CO_2$ atmosphere. Photographs were taken by using phase contrast mode of an Olympus IX81 microscope with a 10× objective lens then electronically amplified whenever needed.

HeV and NiV Neutralization Assays

All live virus experiments were conducted under strict bio-containment procedures in a BSL4 laboratory. $2\times10^4$ Vero cells were added to wells in 150 μl EMEM-10 in a 96-well plate and incubated at 37° C. overnight in a humidified 5% $CO_2$ atmosphere. Antibodies were diluted in EMEM-10 by doubling dilution and an equal volume of either HeV or NiV was added to each dilution and incubated at 37° C. for 30 min. The titer of HeV was $1.0\times10^8$ $TCID_{50}$/ml and NiV was $3.0\times10^7$ $TCID_{50}$/ml. Virus dilutions were done in EMEM-10 and chosen to generate 50 plaques following adsorption of virus for 30 min at 37° C. to Vero cell monolayers ($1.5\times10^3$ $TCID_{50}$/ml for HeV and $7.5\times10^2$ $TCID_{50}$/ml for NiV). Antibody-virus mixtures were added to Vero cell monolayers in quadruplicate and incubated for 30 minutes at 37° C. in a humidified 5% $CO_2$ atmosphere. After 30 minute incubation, antibody-virus mixtures were removed and cells were washed 3 times with $Ca^{++}/Mg^{++}$-free PBS. Two different variations of this assay were conducted. In the first, EMEM-10 was added to Vero cells after washing and incubated overnight. In the second, the same antibody dilution as both the pre-incubation and virus incubation was added to the respective wells and incubated overnight. For both assays, the culture medium was discarded the next day, and plates immersed in ice-cold absolute methanol for 20 min prior to air-drying outside the biohazard level 4 facility. Fixed chamber slides were either stored overnight at 4° C. or immunolabeled immediately with anti-phosphoprotein (P) monospecific antiserum (Michalski, W. P. et al. 2000 *Virus Res* 69:83-93). Wells were washed in 0.01 M PBS, pH 7.2 containing 1% BSA for 5 min. 40 μl of anti-P antiserum (1:200 in PBS-BSA) was applied to each well and incubated at 37° C. for 30 min. Slides were rinsed with PBS containing 0.05% Tween 20 (PBS-T) and washed for 5 min in PBS-BSA. 40 μl of FITC labeled goat anti-rabbit antiserum (ICN Pharmaceuticals, Costa Mesa, USA) diluted 1:200 in PBS-BSA containing DAPI (10 μg/ml) was then applied to each well and incubated at 37° C. for 30 min. Wells were rinsed again with PBS containing 0.05% Tween 20 (PBS-T) and washed for 5 min in PBS-BSA. Wells were overlaid with 100 μl Glycerol/PBS (9:1) containing DABCO (25 μg/ml) and stored in the dark prior to imaging. FITC immunofluorescence was visualized using an Olympus IX71 inverted microscope (Olympus Australia, Mt. Waverley, Australia). Percentage neutralization at a given antibody concentration was calculated as the ratio of the average number of foci per well due to cytopathic effect (CPE) to the same number for the positive control multiplied by 100.

Neutralization of HeV and NiV by Fabs was performed as follows. Fabs were diluted in EMEM-10 by doubling dilution and an equal volume of EMEM-10 containing 200 $TCID_{50}$ of either HeV or NiV was added to each dilution and incubated at 37° C. for 30 min. The titer of HeV was $1.0\times10^8$ $TCID_{50}$/ml and NiV was $3.0\times10^7$ $TCID_{50}$/ml. $2\times10^4$ Vero cells were added to each Fab-virus mixture in six replicate wells and incubated for 5 days. Fab neutralization was determined by the level of cytopathic effect (CPE) in replicate wells at each Fab concentration.

EXAMPLE 2

Affinity Maturation of m102

The original human Fab phage display library from which the antibodies m101-m107 were identified was used as the source of the VL repertoire in the shuffled library. The phagemid preparation from the original library was first digested with Nco I and Spe I and followed by electrophoresis on an agarose gel to separate the VH and CH1 gene fragments from the antibody light chain-containing backbone vector to delete the entire VH repertoire. The gene encoding the VH domain of clone m102 was amplified by error-prone PCR kit from Stratagene to introduce random mutations and then fused with CH1 gene fragment by SOE PCR. The fused fragment was digested with NcoI and Spe I and purified from gel and was then ligated into the purified backbone vector to create the VL-shuffled Fab repertoire. *E. coli* TG1 cells were transformed with the ligation mixtures via electroporation. The transformed TG1 cells were plated on 2YT agar plates containing 100 μg/ml ampicillin and 2% glucose. After incubation overnight at 37° C., all of the colonies grown on the plates were scraped into 5 ml of 2YTAG medium, mixed with 1.2 ml of 50% glycerol (final concentration 10%), aliquoted, and stored at −70° C. as the library stock.

The library stock (100 μl) was grown to log phase in 20 ml of 2YT medium, rescued with M13K07 helper phage, and amplified overnight in 2YT medium (2YT containing 100 μg/ml of ampicillin and 50 μg/ml of kanamycin) at 30° C. The phage preparation was precipitated in 4% PEG, 0.5 M NaCl, resuspended in 1 ml of PBS as phage library stock. Two round of biopanning were performed on Hendra G conjugated magnetic beads as described in the original library panning. 9 clones were identified as affinity maturated antibodies and m102.4 was selected for further characterization.

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

What is claimed is:

1. An isolated antibody selectively binding a Hendra or Nipah G glycoprotein epitope wherein said antibody includes a heavy chain CDR1 region comprising the amino acid sequence of SEQ ID NO: 307, CDR2 region comprising the amino acid sequence of SEQ ID NO: 309, and CDR3 region comprising the amino acid sequence of SEQ ID NO: 311, and a light chain CDR1 region comprising the amino acid sequence of SEQ ID NO: 315, CDR2 region comprising SEQ ID NO: 317 and CDR3 region comprising the amino acid sequence of SEQ ID NO: 319.

2. The isolated antibody of claim 1 wherein said antibody comprises an Fd fragment.

3. The isolated antibody of claim 1 wherein said antibody comprises an Fab fragment.

4. The isolated antibody of claim 1 wherein said antibody includes a heavy chain Fd region comprising the amino acid sequence of SEQ ID NO: 305.

5. The isolated antibody of claim 1 wherein said antibody includes a light chain region comprising the amino acid sequence of SEQ ID NO: 313.

6. The isolated antibody of claim 1 wherein said antibody includes a $V_H$ comprising the amino acid sequence of SEQ ID NO: 305 and the $V_L$ region comprising the amino acid sequence of SEQ ID NO: 313.

7. The isolated antibody of claim 1 wherein said antibody includes a heavy chain with one or more amino acid sequences selected from the group consisting of:

a) FR1 region comprising SEQ ID NO: 306,
b) FR2 region comprising SEQ ID NO: 308,
c) FR3 region comprising SEQ ID NO: 310, and
d) FR4 region comprising SEQ ID NO: 312.

8. The isolated antibody of claim 1 wherein said antibody includes a light chain with one or more amino acid sequences selected from the group consisting of:

a) FR1 region comprising SEQ ID NO: 314,
b) FR2 region comprising SEQ ID NO: 316,
c) FR3 region comprising SEQ ID NO: 318, and
d) FR4 region comprising SEQ ID NO: 320.

9. The isolated antibody of claim 1 wherein said antibody includes a heavy chain with one or more amino acid sequences selected from the group consisting of:

a) FR1 region comprising SEQ ID NO: 306,
b) FR2 region comprising SEQ ID NO: 308,
c) FR3 region comprising SEQ ID NO: 310, and
d) FR4 region comprising SEQ ID NO: 312; and said antibody includes a light chain with one or more amino acid sequences selected from the group consisting of:
a) FR1 region comprising SEQ ID NO: 314,
b) FR2 region comprising SEQ ID NO: 316,
c) FR3 region comprising SEQ ID NO: 318, and
d) FR4 region comprising SEQ ID NO: 320.

10. An isolated humanized antibody selectively binding a Hendra or Nipah G glycoprotein epitope, wherein said antibody includes:

a) Heavy chain $V_H$ region comprising the amino acid sequence of SEQ ID NO: 305,
b) Heavy chain FR1 region comprising the amino acid sequence of SEQ ID NO: 306,
c) Heavy chain CDR1 region comprising the amino acid sequence of SEQ ID NO: 307,
d) Heavy chain FR2 region comprising the amino acid sequence of SEQ ID NO: 308,
e) Heavy chain CDR2 region comprising the amino acid sequence of SEQ ID NO: 309,
f) Heavy chain FR3 region comprising the amino acid sequence of SEQ ID NO: 310,
g) Heavy chain CDR3 region comprising the amino acid sequence of SEQ ID NO: 311,
h) Heavy chain FR4 region comprising the amino acid sequence of SEQ ID NO: 312,
i) Light chain $V_L$ region comprising the amino acid sequence of SEQ ID NO: 313, b) Light chain FR1 region comprising the amino acid sequence of SEQ ID NO: 314, c) Light y chain CDR1 region comprising the amino acid sequence of SEQ ID NO: 315, d) Light y chain FR2 region comprising the amino acid sequence of SEQ ID NO: 316, e) Light chain CDR2 region comprising the amino acid sequence of SEQ ID NO: 317, f) Light chain FR3 region comprising the amino acid sequence of SEQ ID NO: 318, g) Light chain CDR3 region comprising the amino acid sequence of SEQ ID NO: 319, and h) Light chain FR4 region comprising the amino acid sequence of SEQ ID NO: 320.

11. The isolated antibody of claim 10 wherein the antibody is Fab m102.4.

12. The isolated humanized antibody of claim 10, wherein said antibody comprises an Fd fragment.

13. The isolated humanized antibody of claim 10, wherein said antibody comprises an Fab fragment.

14. The antibody of claim 1, wherein the antibody is monoclonal.

15. A pharmaceutical composition comprising a pharmaceutically acceptable carrier and an isolated antibody selected from any of claims 1, 2, 3, 4, 5, 6, 7, 8, 9 or 10.

16. A diagnostic preparation comprising a pharmaceutically acceptable carrier and an isolated antibody selected from any of claims 1, 2, 3, 4, 5, 6, 7, 8, 9 or 10.

* * * * *

UNITED STATES PATENT AND TRADEMARK OFFICE

CERTIFICATE OF CORRECTION

PATENT NO. : 7,988,971 B2
APPLICATION NO. : 11/886307
DATED : August 2, 2011
INVENTOR(S) : Dimiter S. Dimitrov et al.

It is certified that error appears in the above-identified patent and that said Letters Patent is hereby corrected as shown below:

Title Page, Item (75) Inventors: the second Inventor, please correct to --Zhongyu Zhu--

Signed and Sealed this
Eighth Day of November, 2011

David J. Kappos
*Director of the United States Patent and Trademark Office*